US012290641B2

(12) United States Patent
McMenamin et al.

(10) Patent No.: US 12,290,641 B2
(45) Date of Patent: *May 6, 2025

(54) MEDICAL DEVICE PACKAGE WITH FLIP CAP HAVING A SNAP FIT

(71) Applicant: Hollister Incorporated, Libertyville, IL (US)

(72) Inventors: Martin McMenamin, Lifford (IE); Daniel E. O'Brien, Calry (IE); Vincent Naughton, Sligo (IE); Joseph N. Hanley, Sligo (IE); David A. Knauz, Riverwoods, IL (US); Martin P. Creaven, Ballina (IE); Stephen Collum, Castlebar (IE); Jeanne E. Lee, Libertyville, IL (US); Siobhan Duffy, Westport (IE); Marine Veronique Germaine Richard, Carrieres sur Seine (FR); Eugene Canavan, Bray (IE); Scott J. Pupino, Lakewood, IL (US); Kieran J. McFadden, Letterkenny (IE); Claire O'Grady, Castlebar (IE); Daniel A. March, Lake Villa, IL (US)

(73) Assignee: Hollister Incorporated, Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/497,493

(22) Filed: Oct. 30, 2023

(65) Prior Publication Data
US 2024/0058569 A1 Feb. 22, 2024

Related U.S. Application Data

(60) Continuation of application No. 17/379,652, filed on Jul. 19, 2021, now Pat. No. 11,833,312, which is a
(Continued)

(51) Int. Cl.
*A61M 25/00* (2006.01)
*B65D 43/16* (2006.01)
*B65D 83/08* (2006.01)

(52) U.S. Cl.
CPC ......... *A61M 25/002* (2013.01); *B65D 43/162* (2013.01); *A61M 25/0017* (2013.01); *B65D 83/0835* (2013.01)

(58) Field of Classification Search
CPC .............. A61M 25/00; A61M 25/0017; A61M 25/002; B65D 43/16; B65D 43/162; B65D 51/24; B65D 83/08; B65D 83/0835
(Continued)

(56) References Cited

U.S. PATENT DOCUMENTS

D137,496 S 3/1944 Lustig
D139,383 S 11/1944 Lampl
(Continued)

FOREIGN PATENT DOCUMENTS

AT 369994 B 2/1983
CN 2078634 U 6/1991
(Continued)

OTHER PUBLICATIONS

International Search Report and Written Opinion for International Application No. PCT/US2017/028979 Dated Aug. 25, 2017.
(Continued)

*Primary Examiner* — Bryon P Gehman
(74) *Attorney, Agent, or Firm* — Cook Alex Ltd.

(57) ABSTRACT

A package for a medical device such as an intermittent catheter has a case which is closed at one end and open at the other end. A cap is connected to the case by a hinge to permit selectable movement of the cap between an open position, wherein access is provided to the open end of the case, and a closed position, wherein the cap prevents access
(Continued)

to the open end of the case. A seal is connected to one of the cap and case. The seal is engageable with the other of the cap and case when the cap is closed to form a barrier that maintains a sterile environment inside the package. The seal can be repeatedly made and broken whenever the user closes or opens the cap, respectively. The case includes a pair of slots at the open end. A pair of latches are formed in the cap. The latches fit into the slots to prevent lateral forces from distorting the cap when the cap is closed.

20 Claims, 41 Drawing Sheets

Related U.S. Application Data division of application No. 16/094,937, filed as application No. PCT/US2017/028979 on Apr. 21, 2017, now Pat. No. 11,103,676.

(60) Provisional application No. 62/461,635, filed on Feb. 21, 2017, provisional application No. 62/448,748, filed on Jan. 20, 2017, provisional application No. 62/431,856, filed on Dec. 9, 2016, provisional application No. 62/326,322, filed on Apr. 22, 2016.

(58) Field of Classification Search
USPC .................................................. 206/364, 365
See application file for complete search history.

(56) References Cited

U.S. PATENT DOCUMENTS

| | | |
|---|---|---|
| 3,114,455 A | 12/1963 | Claisse et al. |
| 3,203,545 A | 8/1965 | Grossman |
| 3,369,542 A | 2/1968 | Thaidigsman |
| 3,794,042 A | 2/1974 | De Klotz et al. |
| 3,854,483 A | 12/1974 | Powers |
| 3,867,945 A | 2/1975 | Long |
| 3,894,540 A | 7/1975 | Bonner, Jr. |
| 3,920,023 A | 11/1975 | Dye et al. |
| 3,934,722 A | 1/1976 | Goldberg |
| 4,043,345 A | 8/1977 | Kramann et al. |
| 4,109,659 A | 8/1978 | Sheridan |
| 4,248,214 A | 2/1981 | Hannah et al. |
| 4,432,758 A | 2/1984 | Finegold |
| 4,553,959 A | 11/1985 | Hickey et al. |
| 4,684,369 A | 8/1987 | Wildemeersch |
| 4,773,901 A | 9/1988 | Norton |
| 4,898,586 A | 2/1990 | McDonough |
| 4,935,017 A | 6/1990 | Sylvanowicz |
| 4,956,298 A | 9/1990 | Diekmann |
| 5,012,940 A | 5/1991 | Koehn |
| 5,084,036 A | 1/1992 | Rosenbaum |
| D327,327 S | 6/1992 | Deguchi et al. |
| 5,149,326 A | 9/1992 | Woodgrift et al. |
| 5,217,114 A | 6/1993 | Gadberry et al. |
| 5,225,165 A | 7/1993 | Perlman |
| 5,380,270 A | 1/1995 | Ahmadzadeh |
| 5,413,561 A | 5/1995 | Fischell et al. |
| 5,417,326 A | 5/1995 | Winer |
| 5,582,599 A | 12/1996 | Daneshvar |
| D381,422 S | 7/1997 | Erskine et al. |
| D383,538 S | 9/1997 | Erskine et al. |
| 5,868,265 A | 2/1999 | Kobayashi |
| 5,881,774 A | 3/1999 | Utterberg |
| 5,919,170 A | 7/1999 | Woessner |
| 6,059,107 A * | 5/2000 | Nosted et al. ..... A61M 25/0111 206/364 |
| 6,186,325 B1 | 2/2001 | Schmidt et al. |
| 6,258,078 B1 | 7/2001 | Thilly |
| D449,104 S | 10/2001 | Baker et al. |
| 6,328,355 B1 | 12/2001 | Bortz |
| 6,439,410 B1 | 8/2002 | Dubach |
| 6,460,712 B2 | 10/2002 | Smith et al. |
| 6,460,726 B1 | 10/2002 | Hierzer et al. |
| 6,585,721 B2 | 7/2003 | Fiore |
| 6,634,498 B2 | 10/2003 | Kayerod et al. |
| D488,863 S | 4/2004 | Quinn |
| 6,726,649 B2 | 4/2004 | Swenson et al. |
| 6,822,253 B1 | 11/2004 | Martin et al. |
| 6,871,753 B2 | 3/2005 | McHutchinson |
| 6,908,013 B2 | 6/2005 | Thomson et al. |
| 6,908,113 B2 | 6/2005 | Chaduc et al. |
| 6,926,708 B1 | 8/2005 | Franks-Farah et al. |
| D509,352 S | 9/2005 | Raven et al. |
| 6,964,336 B2 | 11/2005 | Harrold |
| 7,120,487 B2 | 10/2006 | Nelson |
| 7,134,575 B2 | 11/2006 | Vogel et al. |
| 7,306,128 B2 | 12/2007 | Eimer |
| 7,311,698 B2 | 12/2007 | Tanghoj et al. |
| 7,353,969 B2 | 4/2008 | McHutchinson |
| D577,813 S | 9/2008 | Seki et al. |
| D577,814 S | 9/2008 | Seki et al. |
| 7,438,704 B1 | 10/2008 | Kawashima et al. |
| D584,408 S | 1/2009 | Castellani |
| D584,409 S | 1/2009 | Miller et al. |
| D584,410 S | 1/2009 | Miller et al. |
| D588,797 S | 3/2009 | Tanghoej et al. |
| 7,546,931 B2 | 6/2009 | Giusti |
| D595,847 S | 7/2009 | Miller et al. |
| 7,571,804 B2 | 8/2009 | Kjellmann Bruun et al. |
| 7,614,514 B2 | 11/2009 | Fuchs |
| 7,624,868 B2 | 12/2009 | Booker et al. |
| 7,655,063 B2 | 2/2010 | Wang et al. |
| 7,682,353 B2 | 3/2010 | Tanghoj et al. |
| D614,396 S | 4/2010 | Tanghoej et al. |
| 7,699,168 B2 | 4/2010 | Ryan et al. |
| 7,717,284 B2 | 5/2010 | Giusti |
| 7,748,550 B2 | 7/2010 | Cho |
| 7,766,163 B2 | 8/2010 | Tanghoej |
| 7,770,726 B2 | 8/2010 | Murray et al. |
| D630,733 S | 1/2011 | Ahlgren |
| 7,867,220 B2 | 1/2011 | Tanghoj |
| 7,886,907 B2 | 2/2011 | Murray et al. |
| 7,967,744 B2 | 6/2011 | Kaye et al. |
| 7,992,737 B2 | 8/2011 | Salice |
| 8,069,980 B2 | 12/2011 | Stopek et al. |
| 8,137,309 B2 | 3/2012 | Nishtala et al. |
| 8,172,101 B2 | 5/2012 | Giusti |
| 8,181,778 B1 | 5/2012 | van Groningen et al. |
| 8,230,993 B2 | 7/2012 | Tanghoej |
| 8,282,624 B2 | 10/2012 | Tanghoej et al. |
| 8,292,110 B2 | 10/2012 | Rutter et al. |
| D673,264 S | 12/2012 | Kunze |
| 8,361,057 B2 | 1/2013 | Tanghoej et al. |
| 8,381,925 B2 | 2/2013 | Skillin et al. |
| 8,398,615 B2 | 3/2013 | Torstensen et al. |
| 8,434,639 B2 | 5/2013 | Markert |
| 8,439,213 B2 | 5/2013 | Goria et al. |
| 8,448,798 B2 | 5/2013 | Groubert et al. |
| 8,491,568 B2 | 7/2013 | Schertiger et al. |
| 8,511,472 B2 | 8/2013 | Dupuis et al. |
| 8,523,843 B2 | 9/2013 | Kavanagh et al. |
| 8,529,549 B2 | 9/2013 | Tanghoj et al. |
| D691,365 S | 10/2013 | Cote |
| 8,579,115 B2 | 11/2013 | Murphy et al. |
| 8,597,245 B2 | 12/2013 | Jeter et al. |
| 8,616,406 B1 | 12/2013 | Sawicki |
| 8,616,407 B2 | 12/2013 | Sawicki |
| D705,925 S | 5/2014 | Murray et al. |
| 8,721,676 B1 | 5/2014 | Janardhan et al. |
| 8,733,566 B2 | 5/2014 | Druitt et al. |
| D707,351 S | 6/2014 | Kunze |
| 8,740,863 B2 | 6/2014 | Nestenborg et al. |
| 8,752,722 B2 | 6/2014 | Kuhn et al. |
| 8,863,968 B2 | 10/2014 | Giusti |
| D724,199 S | 3/2015 | Bambot et al. |
| 9,033,149 B2 | 5/2015 | Terry |
| 9,090,386 B2 | 7/2015 | van Alfen et al. |
| D738,973 S | 9/2015 | Dingman |
| D739,932 S | 9/2015 | Ratjen et al. |
| 9,220,866 B2 | 12/2015 | Van Groningen et al. |

(56) References Cited

U.S. PATENT DOCUMENTS

| | | | |
|---|---|---|---|
| D747,184 S | 1/2016 | Murray et al. |
| 9,277,966 B2 | 3/2016 | Seitz, III |
| 9,334,097 B2 | 5/2016 | Skillin et al. |
| 9,352,318 B2 | 5/2016 | Giusti |
| D760,490 S | 7/2016 | Johnson |
| 9,415,909 B2 | 8/2016 | Druitt et al. |
| 9,422,089 B2 | 8/2016 | Wheeler |
| 9,501,958 B2 | 11/2016 | Pietarinen et al. |
| 9,511,906 B2 | 12/2016 | van Alfen et al. |
| 9,669,187 B2 | 6/2017 | Tjassens et al. |
| 9,687,629 B1 | 6/2017 | Palmer |
| 9,701,451 B2 | 7/2017 | Skillin et al. |
| D796,025 S | 8/2017 | Lo |
| 10,561,817 B2 | 2/2020 | Hannon et al. |
| 10,857,068 B2 | 12/2020 | Davis et al. |
| 2001/0001443 A1 | 5/2001 | Kayerod et al. |
| 2001/0037954 A1 | 11/2001 | Schmidt et al. |
| 2003/0004496 A1 | 1/2003 | Tanghoj |
| 2003/0060807 A1 | 3/2003 | Tanghoj et al. |
| 2003/0141210 A1 | 7/2003 | Yanke et al. |
| 2004/0016714 A1 | 1/2004 | Wood et al. |
| 2004/0150221 A1 | 8/2004 | Brown |
| 2004/0158231 A1 | 8/2004 | Tanghoj et al. |
| 2004/0256264 A1* | 12/2004 | Israelsson ........... B65D 85/24 206/364 |
| 2005/0043715 A1 | 2/2005 | Nestenborg et al. |
| 2005/0067366 A1 | 3/2005 | Dubach |
| 2005/0106339 A1 | 5/2005 | Baker |
| 2005/0106340 A1 | 5/2005 | Baker |
| 2005/0274687 A1 | 12/2005 | McCutchan |
| 2006/0091670 A1 | 5/2006 | Gaynor |
| 2006/0116661 A1 | 6/2006 | Tanghoej |
| 2006/0142737 A1 | 6/2006 | Tanghoj |
| 2006/0180585 A1 | 8/2006 | Cunningham et al. |
| 2007/0034537 A1 | 2/2007 | Fago et al. |
| 2007/0068977 A1 | 3/2007 | Vogel et al. |
| 2008/0033371 A1 | 2/2008 | Updegraff et al. |
| 2008/0183181 A1 | 7/2008 | Treacy et al. |
| 2008/0264961 A1 | 10/2008 | Sawyer |
| 2008/0289984 A1 | 11/2008 | Raven et al. |
| 2008/0319423 A1 | 12/2008 | Tanghoj et al. |
| 2009/0008279 A1 | 1/2009 | Tanghoej |
| 2009/0050253 A1 | 2/2009 | Thomas et al. |
| 2009/0054876 A1 | 2/2009 | Borodulin et al. |
| 2009/0131917 A1 | 5/2009 | Kavanagh et al. |
| 2009/0166361 A1 | 7/2009 | Lourenco |
| 2009/0299334 A1 | 12/2009 | Nishtala et al. |
| 2010/0106236 A1 | 4/2010 | Nelson |
| 2010/0211050 A1 | 8/2010 | Luther |
| 2010/0224643 A1 | 9/2010 | Daggett |
| 2010/0256580 A1 | 10/2010 | Faber |
| 2010/0324540 A1 | 12/2010 | Paulen et al. |
| 2011/0060317 A1 | 3/2011 | Frojd |
| 2011/0224653 A1 | 9/2011 | Torstensen |
| 2012/0016318 A1 | 1/2012 | Hoang et al. |
| 2012/0051967 A1 | 3/2012 | Murphy et al. |
| 2012/0165791 A1 | 6/2012 | Lovmar et al. |
| 2012/0168324 A1 | 7/2012 | Carleo |
| 2012/0179144 A1 | 7/2012 | Carleo |
| 2012/0271281 A1 | 10/2012 | Schertiger |
| 2013/0068767 A1 | 3/2013 | Fraser et al. |
| 2013/0134123 A1 | 5/2013 | Fraser et al. |
| 2013/0150828 A1 | 6/2013 | Conway |
| 2013/0161344 A1 | 6/2013 | Park et al. |
| 2013/0186791 A1 | 7/2013 | Triquigneaux |
| 2013/0218136 A1 | 8/2013 | Tanghoej et al. |
| 2013/0240393 A1 | 9/2013 | Bode et al. |
| 2013/0261608 A1 | 10/2013 | Tanghoj |
| 2013/0289537 A1 | 10/2013 | Schertiger et al. |
| 2013/0292286 A1 | 11/2013 | Van Groningen et al. |
| 2013/0299516 A1 | 11/2013 | Dupuis et al. |
| 2013/0327664 A1 | 12/2013 | Tanghoj |
| 2014/0262860 A1 | 9/2014 | Hagel |
| 2014/0262903 A1 | 9/2014 | Mitten et al. |
| 2014/0263436 A1 | 9/2014 | Gelov et al. |
| 2014/0360896 A1 | 12/2014 | Torstensen |
| 2015/0018803 A1 | 1/2015 | Tjassens et al. |
| 2015/0352321 A1 | 12/2015 | Hannon et al. |
| 2016/0016703 A1 | 1/2016 | Muhlemann |
| 2016/0023816 A1 | 1/2016 | Giraud |
| 2016/0023818 A1 | 1/2016 | Gelov et al. |
| 2016/0038717 A1 | 2/2016 | Murray et al. |
| 2016/0059999 A1 | 3/2016 | Fraser et al. |
| 2016/0172742 A1 | 6/2016 | Forster |
| 2016/0193447 A1 | 7/2016 | Matthiassen |
| 2016/0228872 A1 | 8/2016 | Giusti |
| 2016/0325895 A1 | 11/2016 | Browning, Jr. |
| 2016/0332789 A1 | 11/2016 | Yerecic |
| 2017/0014597 A1 | 1/2017 | Hagel |
| 2017/0080177 A1 | 3/2017 | Tanghoej et al. |
| 2017/0107365 A1 | 4/2017 | Rycroft et al. |
| 2017/0166369 A1 | 6/2017 | Mitten et al. |
| 2017/0173300 A1 | 6/2017 | Hannon et al. |
| 2017/0175428 A1 | 6/2017 | Quinn et al. |
| 2017/0326334 A1 | 11/2017 | Terry |

FOREIGN PATENT DOCUMENTS

| | | |
|---|---|---|
| CN | 2340720 Y | 9/1999 |
| DE | 20117438 | 3/2002 |
| DE | 10213411 | 10/2003 |
| DE | 20317135 | 1/2004 |
| DE | 202005008071 | 7/2005 |
| DE | 102004013712 | 8/2005 |
| DE | 202005009946 | 9/2005 |
| DE | 202006013663 | 11/2006 |
| DE | 202010006267 | 11/2010 |
| DE | 202010007433 | 6/2011 |
| DE | 202011107025 | 1/2013 |
| DE | 202011107059 | 1/2013 |
| DE | 102013014483 | 6/2014 |
| DE | 202017101126 | 3/2017 |
| DE | 102016205834 | 5/2017 |
| DK | 173714 | 7/2001 |
| EP | 0041487 | 12/1981 |
| EP | 0134630 | 3/1985 |
| EP | 0781572 | 7/1997 |
| EP | 0812287 | 12/1997 |
| EP | 0861639 | 9/1998 |
| EP | 0910425 | 4/1999 |
| EP | 0923398 | 6/1999 |
| EP | 0933304 | 8/1999 |
| EP | 0996542 | 5/2000 |
| EP | 1023882 | 8/2000 |
| EP | 1086024 | 3/2001 |
| EP | 1278679 | 1/2003 |
| EP | 1317382 | 6/2003 |
| EP | 1334039 | 8/2003 |
| EP | 1392575 | 3/2004 |
| EP | 1409369 | 4/2004 |
| EP | 1466645 | 10/2004 |
| EP | 1487712 | 12/2004 |
| EP | 1593710 | 11/2005 |
| EP | 1607344 | 12/2005 |
| EP | 1615960 | 1/2006 |
| EP | 1634554 | 3/2006 |
| EP | 1638856 | 3/2006 |
| EP | 1671663 | 6/2006 |
| EP | 1696990 | 9/2006 |
| EP | 1720772 | 11/2006 |
| EP | 1799574 | 6/2007 |
| EP | 1858575 | 11/2007 |
| EP | 1863719 | 12/2007 |
| EP | 1878461 | 1/2008 |
| EP | 1897579 | 3/2008 |
| EP | 1897580 | 3/2008 |
| EP | 1963195 | 9/2008 |
| EP | 1966058 | 9/2008 |
| EP | 1979032 | 10/2008 |
| EP | 1982741 | 10/2008 |
| EP | 1986921 | 11/2008 |
| EP | 2035292 | 3/2009 |
| EP | 2042211 | 4/2009 |
| EP | 2044963 | 4/2009 |

(56) References Cited

FOREIGN PATENT DOCUMENTS

| | | |
|---|---|---|
| EP | 2060296 | 5/2009 |
| EP | 2072075 | 6/2009 |
| EP | 2106821 | 10/2009 |
| EP | 2242696 | 10/2010 |
| EP | 2250102 | 11/2010 |
| EP | 2251454 | 11/2010 |
| EP | 2292294 | 3/2011 |
| EP | 2295108 | 3/2011 |
| EP | 2308543 | 4/2011 |
| EP | 2325100 | 5/2011 |
| EP | 2450076 | 5/2012 |
| EP | 2468319 | 6/2012 |
| EP | 2504054 | 10/2012 |
| EP | 2515985 | 10/2012 |
| EP | 2576374 | 4/2013 |
| EP | 2596831 | 5/2013 |
| EP | 2605977 | 6/2013 |
| EP | 2617316 | 7/2013 |
| EP | 2638927 | 9/2013 |
| EP | 2682069 | 1/2014 |
| EP | 2686054 | 1/2014 |
| EP | 2750748 | 7/2014 |
| EP | 2774648 | 9/2014 |
| EP | 2782842 | 10/2014 |
| EP | 2785409 | 10/2014 |
| EP | 2823845 | 1/2015 |
| EP | 3033279 | 6/2016 |
| EP | 3038075 | 6/2016 |
| EP | 3113922 | 1/2017 |
| EP | 3210909 | 8/2017 |
| EP | 3248620 | 11/2017 |
| FR | 2717676 | 9/1995 |
| FR | 2801567 | 6/2001 |
| GB | 2031735 | 4/1980 |
| GB | 2033231 | 5/1980 |
| GB | 2322079 | 8/1998 |
| JP | 2001025473 | 1/2001 |
| KR | 20110101674 | 9/2011 |
| PT | 2216064 | 9/2016 |
| SE | 514121 | 1/2001 |
| WO | WO9608219 | 3/1996 |
| WO | WO9726937 | 7/1997 |
| WO | WO9741811 | 11/1997 |
| WO | WO9811932 | 3/1998 |
| WO | WO9819729 | 5/1998 |
| WO | WO9930761 | 6/1999 |
| WO | WO9942155 | 8/1999 |
| WO | WO0016843 | 3/2000 |
| WO | WO0030575 | 6/2000 |
| WO | WO0047494 | 8/2000 |
| WO | WO0143807 | 6/2001 |
| WO | WO0160255 | 8/2001 |
| WO | WO02060361 | 8/2002 |
| WO | WO02080843 | 10/2002 |
| WO | WO03001994 | 1/2003 |
| WO | WO03008028 | 1/2003 |
| WO | WO03008029 | 1/2003 |
| WO | WO03022561 | 3/2003 |
| WO | WO03045487 | 6/2003 |
| WO | WO03061732 | 7/2003 |
| WO | WO03092779 | 11/2003 |
| WO | WO03097237 | 11/2003 |
| WO | WO2004021890 | 3/2004 |
| WO | WO2004032750 | 4/2004 |
| WO | WO2004035123 | 4/2004 |
| WO | WO2004050155 | 6/2004 |
| WO | WO2004054446 | 7/2004 |
| WO | WO2004054653 | 7/2004 |
| WO | WO2004056414 | 7/2004 |
| WO | WO2004089454 | 10/2004 |
| WO | WO2004103153 | 12/2004 |
| WO | WO2005014055 | 2/2005 |
| WO | WO2005056414 | 6/2005 |
| WO | WO2005092418 | 10/2005 |
| WO | WO2006005349 | 1/2006 |
| WO | WO2006017439 | 2/2006 |
| WO | WO2006044249 | 4/2006 |
| WO | WO2006044621 | 4/2006 |
| WO | WO2006045809 | 5/2006 |
| WO | WO2006092150 | 9/2006 |
| WO | WO2006121183 | 11/2006 |
| WO | WO2007005851 | 1/2007 |
| WO | WO2007022223 | 2/2007 |
| WO | WO2007038988 | 4/2007 |
| WO | WO2007050685 | 5/2007 |
| WO | WO2007081264 | 7/2007 |
| WO | WO2007082540 | 7/2007 |
| WO | WO2007106356 | 9/2007 |
| WO | WO2007106431 | 9/2007 |
| WO | WO2007111891 | 10/2007 |
| WO | WO2007121137 | 10/2007 |
| WO | WO2008024136 | 2/2008 |
| WO | WO2008030999 | 3/2008 |
| WO | WO2008039910 | 4/2008 |
| WO | WO2008089081 | 7/2008 |
| WO | WO2008090551 | 7/2008 |
| WO | WO2008137353 | 11/2008 |
| WO | WO2009010975 | 1/2009 |
| WO | WO2009017541 | 2/2009 |
| WO | WO2009068043 | 6/2009 |
| WO | WO2009139878 | 11/2009 |
| WO | WO2010006620 | 1/2010 |
| WO | WO2010130261 | 11/2010 |
| WO | WO2011011023 | 1/2011 |
| WO | WO2011019359 | 2/2011 |
| WO | WO2011026929 | 3/2011 |
| WO | WO2011034911 | 3/2011 |
| WO | WO2011079129 | 6/2011 |
| WO | WO2011109393 | 9/2011 |
| WO | WO2011147803 | 12/2011 |
| WO | WO2012006629 | 1/2012 |
| WO | WO2012013662 | 2/2012 |
| WO | WO2012016179 | 2/2012 |
| WO | WO2012016570 | 2/2012 |
| WO | WO2012016571 | 2/2012 |
| WO | WO2012060699 | 5/2012 |
| WO | WO2012079590 | 6/2012 |
| WO | WO2012085107 | 6/2012 |
| WO | WO2012110755 | 8/2012 |
| WO | WO2012134804 | 10/2012 |
| WO | WO2012154946 | 11/2012 |
| WO | WO2012156478 | 11/2012 |
| WO | WO2012166045 | 12/2012 |
| WO | WO2012166967 | 12/2012 |
| WO | WO2013029620 | 3/2013 |
| WO | WO2013029621 | 3/2013 |
| WO | WO2013029622 | 3/2013 |
| WO | WO2013075725 | 5/2013 |
| WO | WO2013083137 | 6/2013 |
| WO | WO2013098190 | 7/2013 |
| WO | WO2013105091 | 7/2013 |
| WO | WO2014062223 | 4/2014 |
| WO | WO2014062225 | 4/2014 |
| WO | WO2014063711 | 5/2014 |
| WO | WO2014074141 | 5/2014 |
| WO | WO2014074147 | 5/2014 |
| WO | WO2014081859 | 5/2014 |
| WO | WO2014085597 | 6/2014 |
| WO | WO2014093056 | 6/2014 |
| WO | WO2014139767 | 9/2014 |
| WO | WO2014140328 | 9/2014 |
| WO | WO2014142895 | 9/2014 |
| WO | WO2014142917 | 9/2014 |
| WO | WO2014142923 | 9/2014 |
| WO | WO2014142930 | 9/2014 |
| WO | WO2014144714 | 9/2014 |
| WO | WO2014145211 | 9/2014 |
| WO | WO2014147620 | 9/2014 |
| WO | WO2014149276 | 9/2014 |
| WO | WO2014159869 | 10/2014 |
| WO | WO2014165046 | 10/2014 |
| WO | WO2014176486 | 10/2014 |
| WO | WO2014176867 | 11/2014 |
| WO | WO2015065725 | 5/2015 |

(56) References Cited

FOREIGN PATENT DOCUMENTS

| WO | WO2015066673 | 5/2015 |
|----|--------------|--------|
| WO | WO2015075841 | 5/2015 |
| WO | WO2015120119 | 8/2015 |
| WO | WO2015184365 | 12/2015 |
| WO | WO2016044379 | 3/2016 |
| WO | WO2016094606 | 6/2016 |
| WO | WO2017024106 | 2/2017 |
| WO | WO2017174715 | 10/2017 |
| WO | WO2017185029 | 10/2017 |
| WO | WO2017185052 | 10/2017 |

OTHER PUBLICATIONS

International Search Report and Written Opinion for International Application No. PCT/US2018/018965 dated Sep. 24, 2018.
International Search Report and Written Opinion for International Application No. PCT/US2015/033344 dated Mar. 12, 2015.
International Search Report dated Feb. 24, 2015, for International Application No. PCT/US2014/053573.
"Total Body Relief and Hygiene for Travel, Home bath, and life's less comfortable moments," http://www.biorelief.com/blog/self-cath-fits-in-your-pocket/ dated Apr. 19, 2014.
Urinary Incontinence Applicance, Aids and Equipment, R.N.P. Carroll, retrieved on Apr. 3, 2014 from http://link.springer.com/chapter/10.1007/978-1-4471-1461-1_6# dated Dec. 31,.

\* cited by examiner

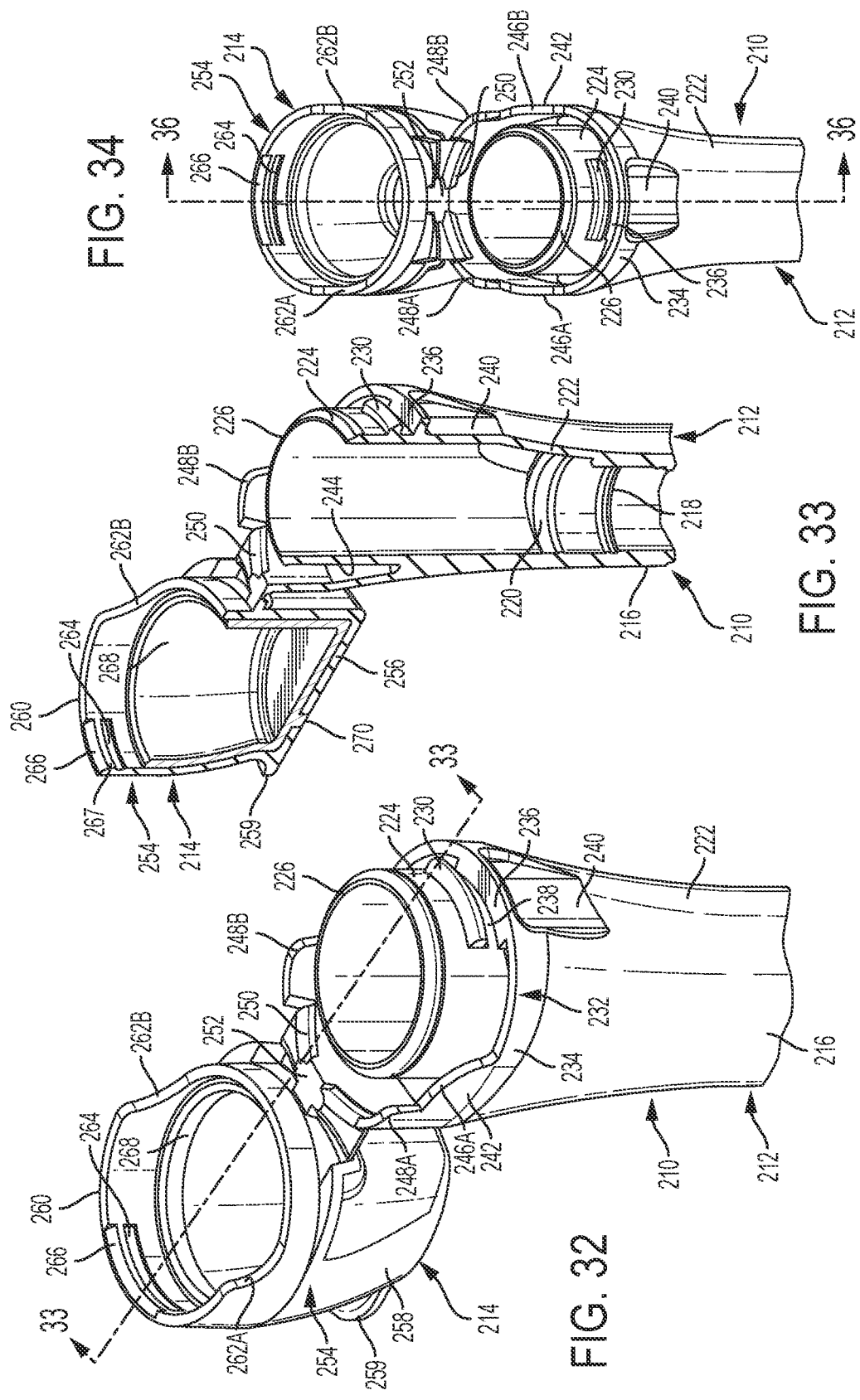

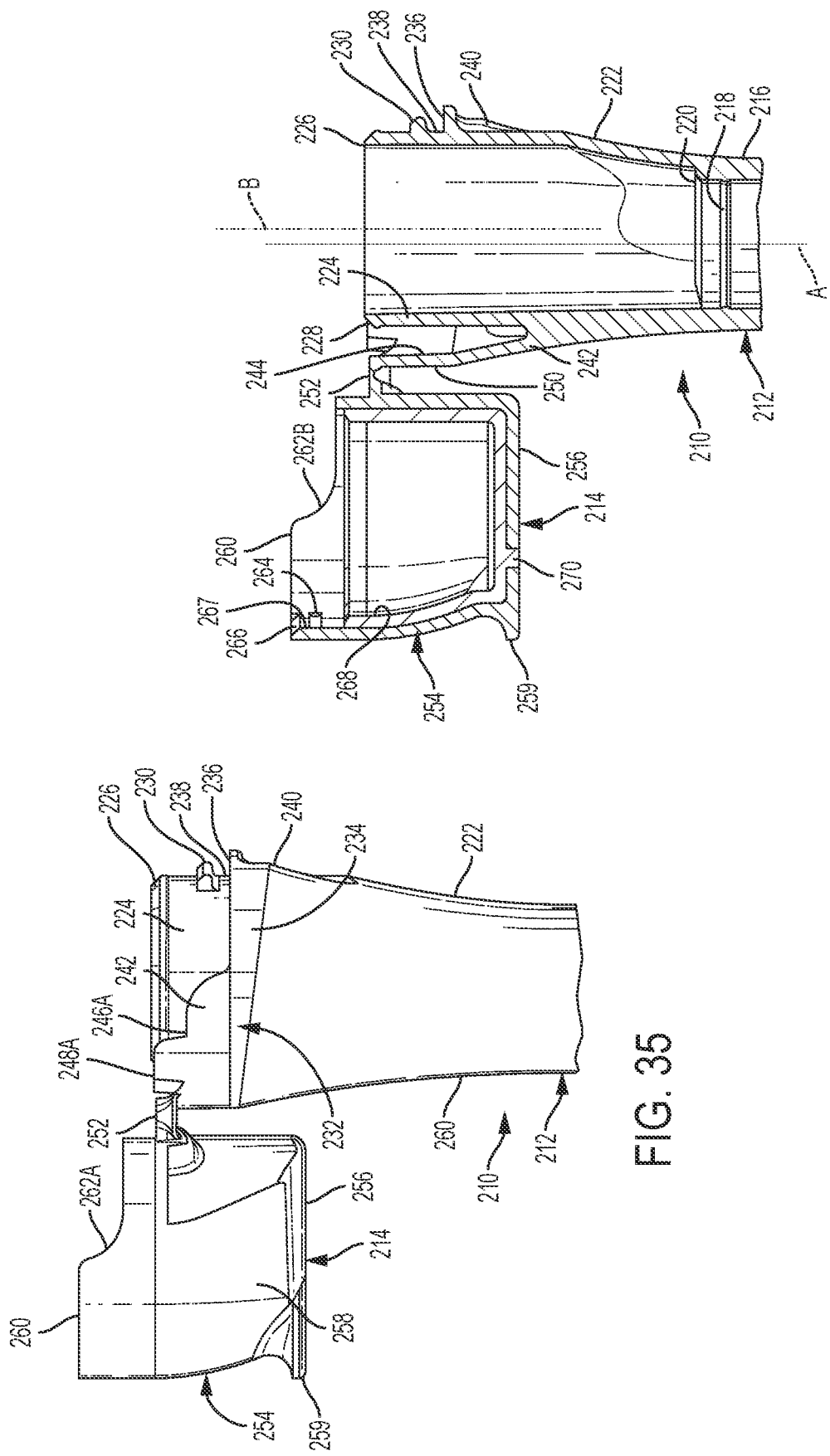

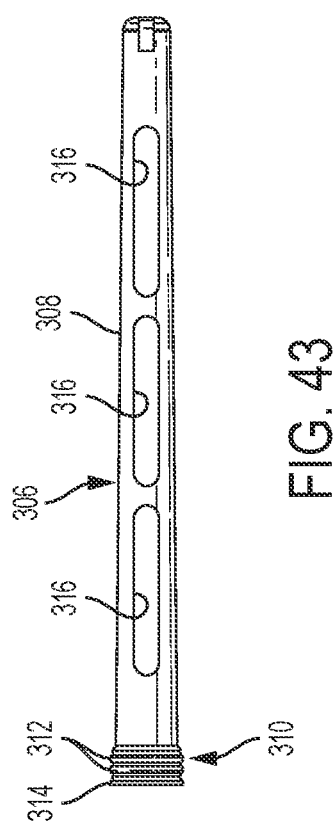
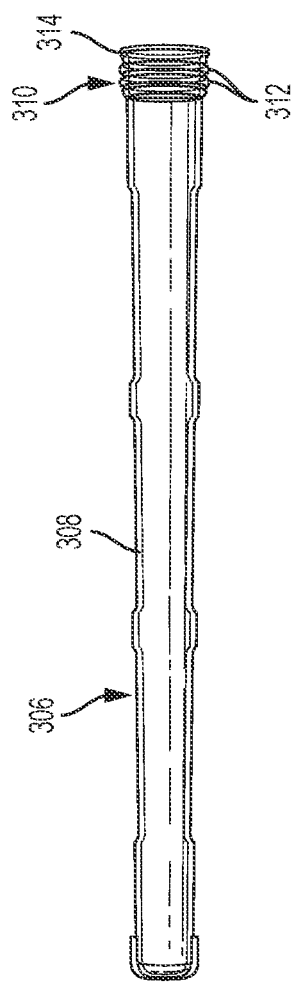
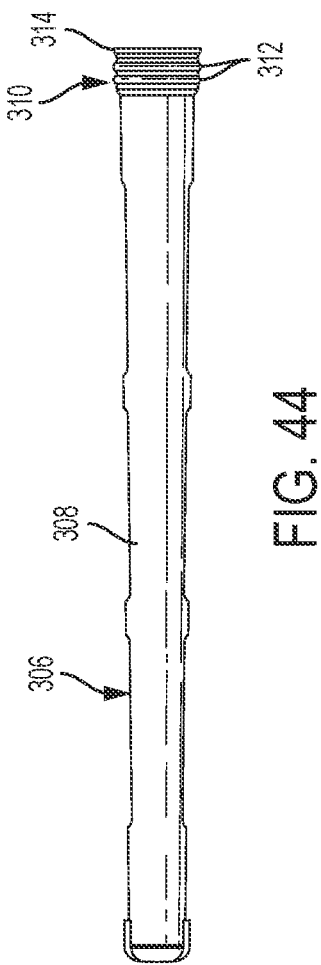
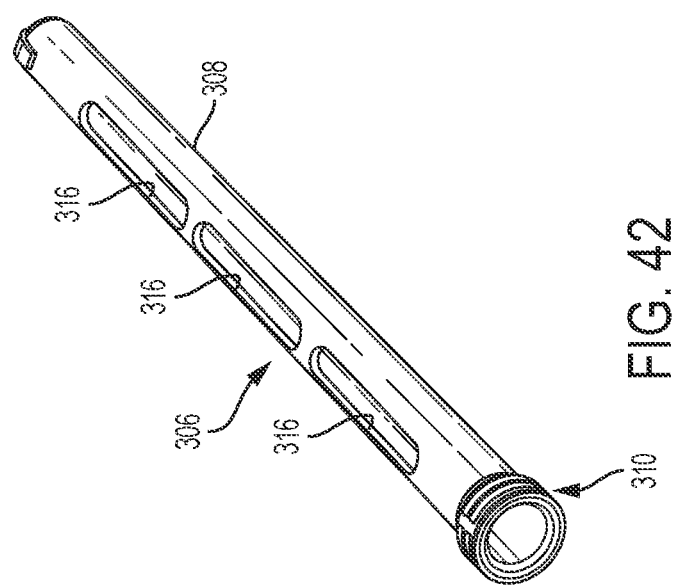
FIG. 42
FIG. 43
FIG. 44
FIG. 45

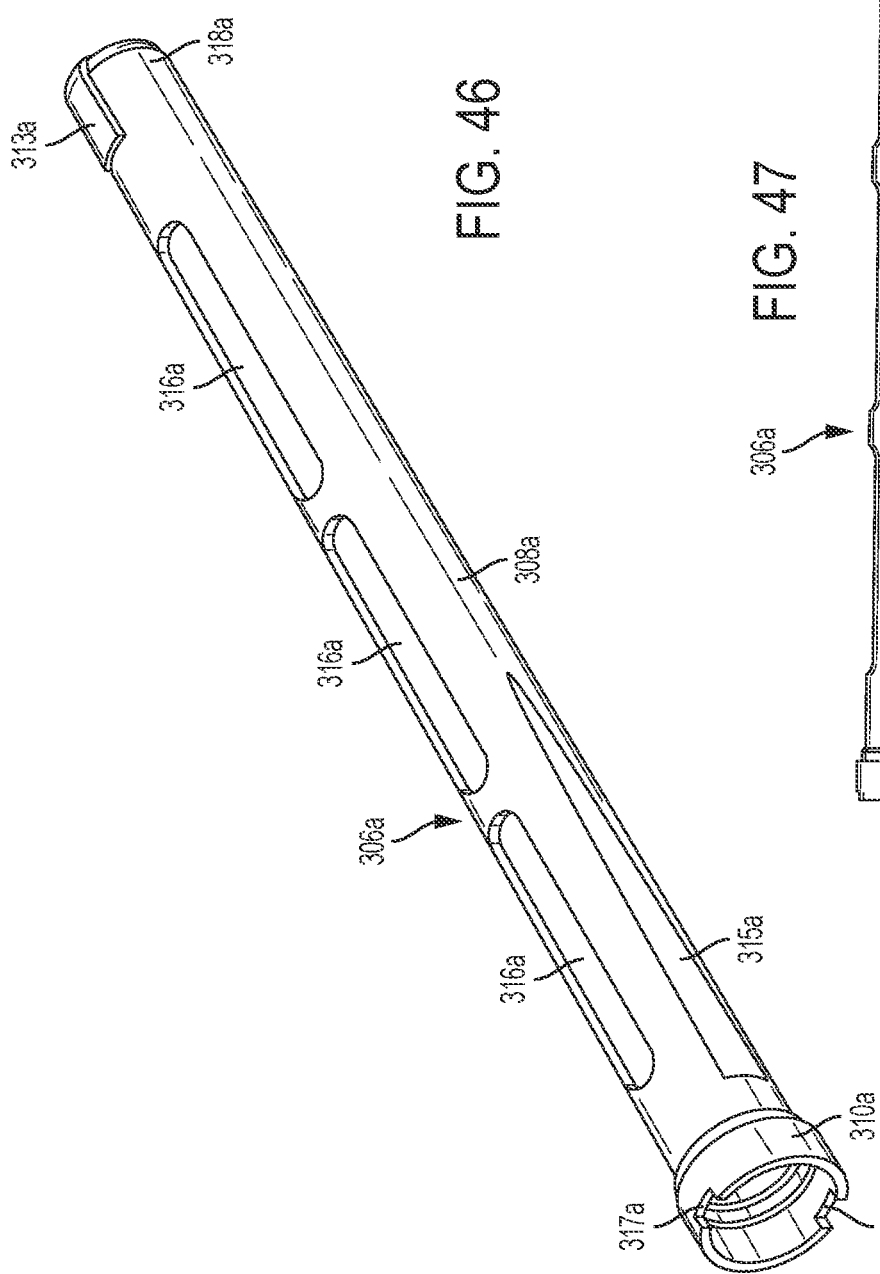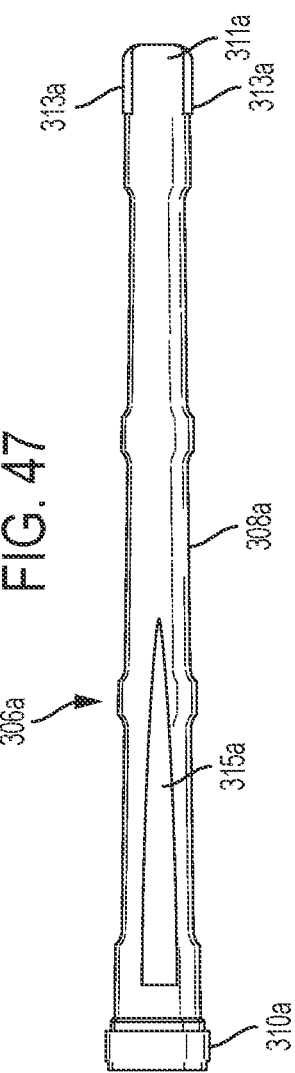

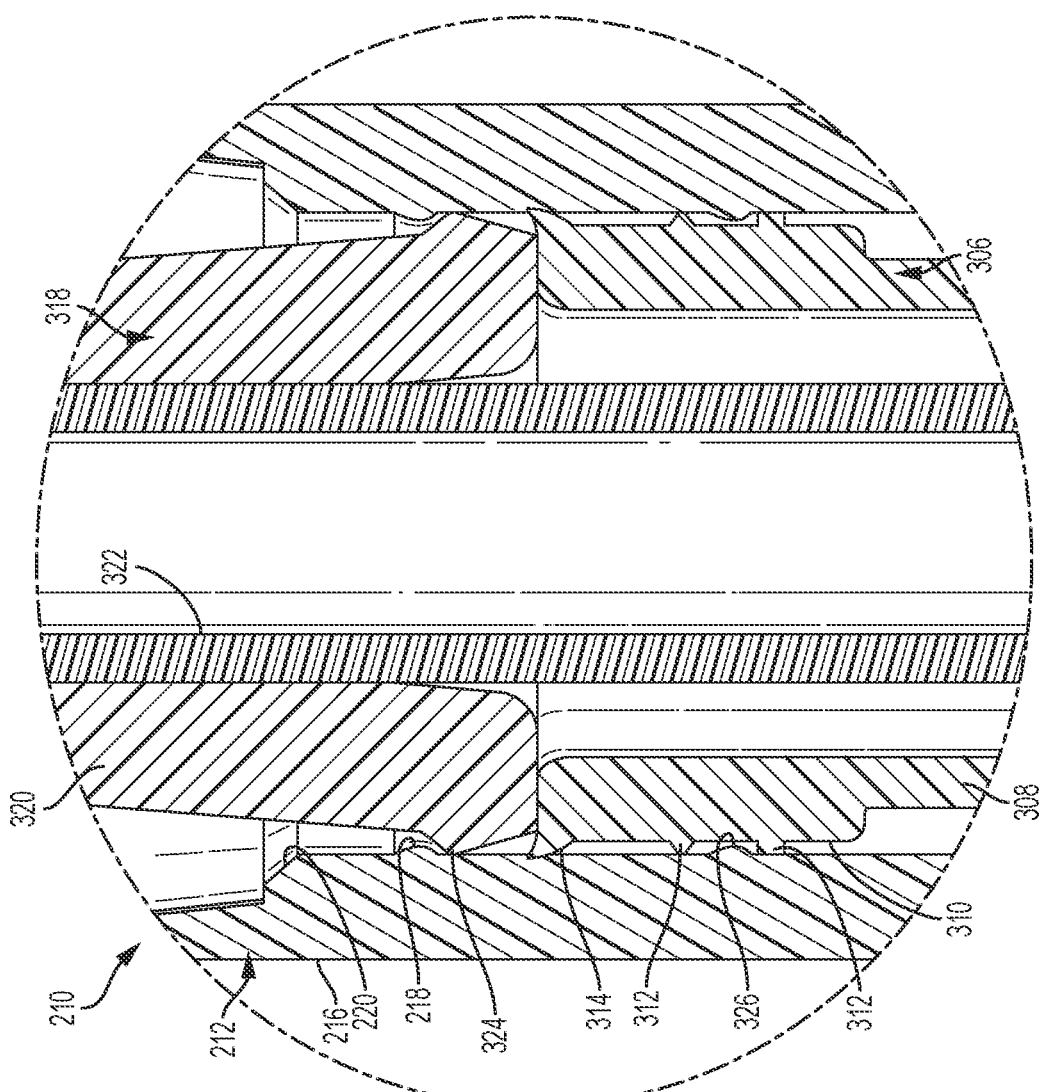
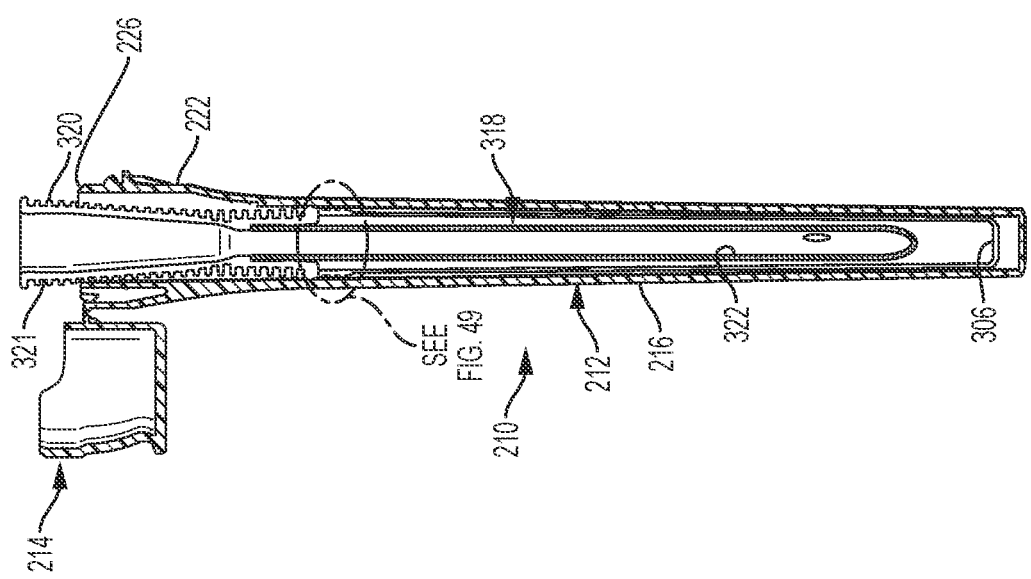
FIG. 49
FIG. 48

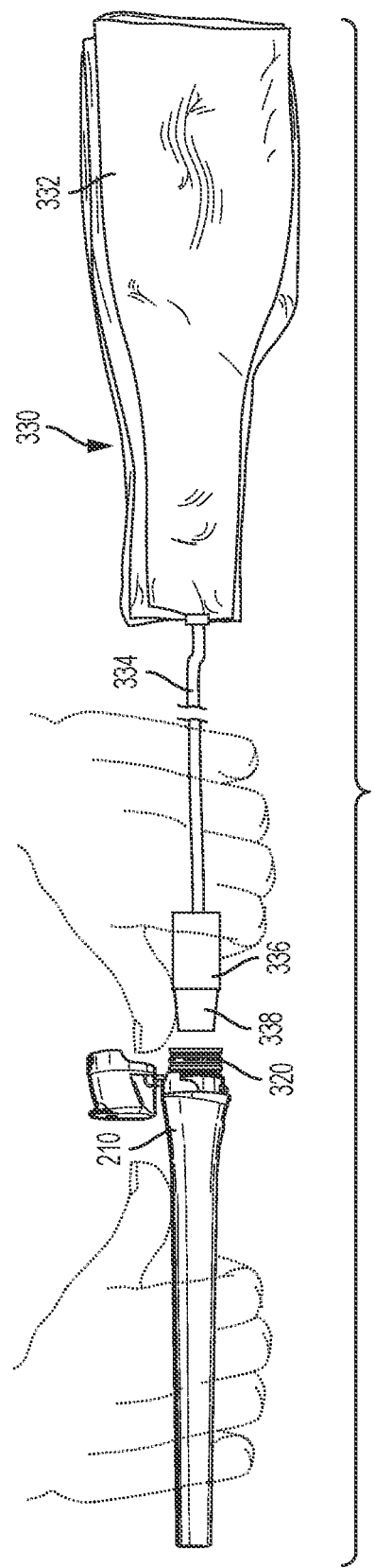
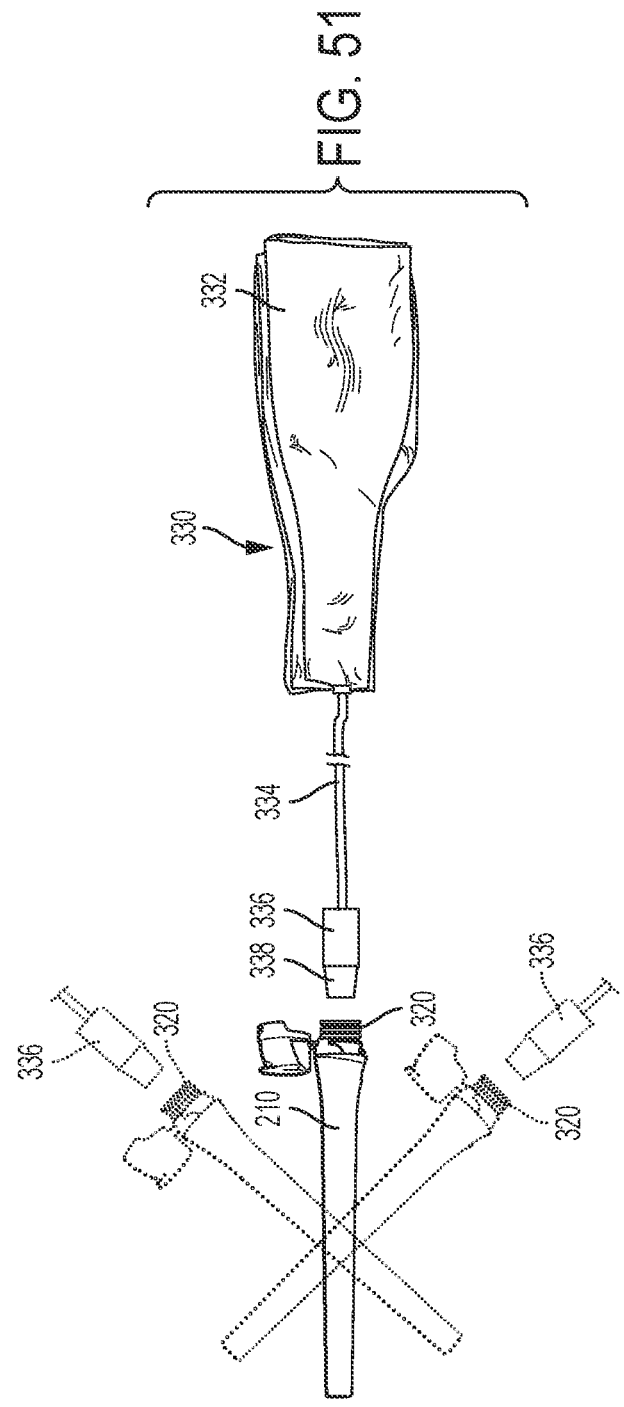
FIG. 50
FIG. 51

MEDICAL DEVICE PACKAGE WITH FLIP CAP HAVING A SNAP FIT

CROSS-REFERENCE TO RELATED APPLICATIONS

The present application is a continuation of U.S. Nonprovisional application Ser. No. 17/379,652, filed Jul. 19, 2021, which is a divisional of U.S. Nonprovisional application Ser. No. 16/094,937, filed Oct. 19, 2018, which is a National Stage of PCT International Application No. PCT/US2017/028979, filed Apr. 21, 2017 which claims the benefit of and priority to: U.S. Provisional Patent Application No. 62/326,322, filed Apr. 22, 2016; U.S. Provisional Patent Application No. 62/431,856, filed Dec. 9, 2016; U.S. Provisional Patent Application No. 62/448,748, filed Jan. 20, 2017; and U.S. Provisional Patent Application No. 62/461,635, filed Feb. 21, 2017, the disclosures of all of which are hereby incorporated herein by reference.

FIELD OF THE DISCLOSURE

This disclosure relates generally to packaging for medical devices such as urinary catheters. More particularly, this disclosure relates to compact catheters, such as urinary catheters, and the packaging, storing and hydrating/lubricating of such catheters.

BACKGROUND

Intermittent catheterization is a good option for many users who suffer from a neurogenic bladder, that is, an atonic or unstable bladder associated with a neurological condition, such as diabetes, stroke, or spinal cord injury. Very often a neurogenic bladder is caused by conditions which may also result in diminished dexterity of the user.

Commonly, in intermittent catheterization single use, individually packaged, sterile catheters are used. Catheters often include a surface treatment that reduces friction to allow for easier and less traumatic insertion into and through the user's urethra.

Regardless of whether a surface treatment is used or what type of surface treatment is used, some type of package for the catheter is required. In the past various kinds of packages have been used, including molded containers of assorted sizes and shapes, bags and pouches made of plastic or metal foil, and similar kinds of devices While these prior art packages generally accomplish the objective of protecting the catheter during transport, storage and preparation for use, they suffer from disadvantages that range from fundamental—the packages may break open prematurely; to economic—the package designs are wasteful of material and labor; to the annoying—the packages confuse users as to how to open them or are difficult for a user of low dexterity to easily access the catheter, or the packages tend to spill the hydrating medium upon opening.

Accordingly, what is needed is a catheter package that is economical to manufacture and fill, reliable throughout its useful life, and simple and intuitive to use. It is also desirable to have a compact package which is can be discreetly carried by the user in a purse or pouch; discrete to dispose of in a waste bin; and intuitive and easy to open, particularly by a user with low dexterity. Additional desirable features of the package include easy removal of the catheter from the case; easy reclosing of the case after use; hygienic use; and it should be discreet and clean to carry after use.

Because users often carry intermittent catheters with them in containers such as purses, handbags, shoulder bags, backpacks and the like, the sealed catheter package should be capable of withstanding compression and other forces to which such containers are typically subjected. More particularly, the catheter package should remain sealed even when subjected to such forces so as to, among other things, maintain the sterility of the catheter within the package.

Furthermore, users will often prefer to return a used catheter to their purse or bag for subsequent disposal. Accordingly, the catheter package should be capable of receiving a used catheter back in the package and then being reclosed in a sealed and secured manner. Thus, a catheter package with a reliably reclosable cap would also be desired. Convenience may be further enhanced if the reclosable cap is attached to the remainder of the package so the cap does not become misplaced during use of the catheter.

As described above, many users of intermittent catheters have limited manual dexterity that can make it difficult for them to open a package and extract a catheter from the package. Thus, while reliable and secure capping and re-capping are a desired aspect of a compact catheter, also desired is the ability to easily open the package, access and extract the catheter. Accordingly, it would be desirable to provide a catheter and catheter package wherein extraction of the catheter is made easier by presenting at least a portion of the catheter (that is not inserted into the urethra of the user, such as the funnel) beyond an open end of the package when the cap is removed. Thus, the end of the funnel is presented for easy extraction and/or for easy and hygienic attachment of a urine collection bag, if desired.

Of course, having at least a portion of catheter or the funnel extending beyond the open end of the package may make the above-described sterile sealing, capping and recapping operations more difficult to achieve. For example, providing a cap hinge that is unobtrusive but affords an arc of motion for the cap that allows the cap to clear the funnel during opening and closing movements and attain the aforementioned sealing (capping) and re-sealing (e.g., "dynamic sealing") presents one challenge. Still another challenge is providing a cap that can be configured to achieve reliable sealing over an extending portion of the catheter (e.g., funnel) while withstanding the forces and loads to which it may be subjected while being carried in a handbag, purse or other receptacle which can compromise the seal. Side loads, i.e., radial or tangential loads on the cap can be a particular problem, especially on the portion of the cap opposite the hinge location. The catheter packages described herein address these concerns.

SUMMARY

In one aspect, the present disclosure is directed to a catheter package, including a case having a hollow tube which is closed at one end and open at the other end, and a cap. The package may include a hinge having one end connected to the cap and a second end connected to said other end of the hollow tube. The hinge permits selectable movement of the cap between an open position, wherein access is provided to the open end of the hollow tube, and a closed position, wherein the cap prevents access to the open end of the hollow tube. A seal is connected to at least one of the cap and case. The seal is engageable with the other of the cap and case when the cap is in the closed position to form a barrier between the cap and case that maintains a sterile environment inside the case and cap.

In another aspect, the present disclosure is directed to a catheter package including a case having a hollow tube which is closed at one end and open at the other end and a cap. The package may include a hinge having one end connected to the cap and a second end connected to the other end of the hollow tube. The hinge permits selectable movement of the cap between an open position, wherein access is provided to the open end of the hollow tube, and a closed position, wherein the cap prevents access to the open end of the hollow tube. A seal connected to at least one of the cap and case is provided. The seal is engageable with the other of the cap and case when the cap is in the closed position to form a seal between the cap and case that can be repeatedly made and broken whenever the user closes or opens the cap, respectively.

In one more particular aspect, the present disclosure includes a hard plastic packaging that holds a short, hydrophilic coated catheter. The catheter may have a length of, by way of example only, about 91 mm of exposed length. A funnel is attached to the catheter. The funnel may be, for example, about 40 mm long. The hard packaging enables the properties of vapor hydration through a hydration liner that separates a water chamber from the hydrophilic coated catheter.

In another more particular aspect, the present disclosure is directed to a hard plastic packaging that holds a short, hydrophilic coated catheter. The catheter tubing may have a length of, by way of example only, about 91 mm of exposed length. A funnel is attached to the catheter tubing. The funnel may be, for example, about 40 mm long. The hard packaging enables the properties of vapor hydration through a hydration liner that separates a water chamber from the hydrophilic coated catheter.

In a further aspect, the present disclosure is directed to a package that has a hollow plastic case for receiving the catheter. The case has a generally tubular wall closed at one end by a bottom wall. The opposite end of the case is open and has a cap attached to it by a hinge. The cap is selectably movable between open and closed positions in which the cap uncovers or covers the open end of the case, respectively. The cap has a pair of latches on the bottom edge thereof. A pair of slots are formed on the top of the case and define a detent between them. When the cap is placed in the closed position the latches fit into the slots and engage the detent to retain the cap in the closed position by releasably resisting vertical lifting forces on the cap. Engagement of the detent by the latches also prevents lateral forces on the closed cap from dislodging the cap or impairing its seal.

A case insert has a lower, collet portion engaging the internal surface of the case's tubular wall just below the open end thereof. An upper, projection portion of the case insert extends axially upwardly from the collet and protrudes beyond the open end of the case's tubular wall. An O-ring is seated in a groove on the outer surface of the projection. The O-ring is engageable with the interior surface of the cap when the cap is in the closed position. The cap is configured to fit around and clear the upstanding funnel and the projection of the case insert during opening and closing motions of the cap. The case insert may be made of a relatively rigid material to support the O-ring in sealing engagement with the cap even after repeated closing and opening sequences of the cap. The case insert also helps resist distortion of the location of the closed cap on the case due to side loading of the cap, i.e., tangential or circumferential forces on the cap that may be encountered during storage and transport of the package.

The lower end of the collet portion of the case insert may have a radially inwardly extending foot that engages a flange on the lower end of the funnel to limit the extent to which the catheter can be inserted into the case. The foot is located such that the upper portion of the funnel extends above the open end of the case when the catheter is stored in the package. Alternately, the inwardly extending foot could be located on the case. In this configuration the funnel interacts with the case, not the case insert.

In a further aspect, the present disclosure is directed to a case insert that has a shortened collet portion with ribs formed around its internal surface. The bottom edge of the collet is supported in the tubular wall of the case by a ledge.

In a still further aspect, the present disclosure is directed to a package that has a hollow plastic tube for receiving the catheter. The tube has a generally cylindrical wall closed at one end by a bottom wall. The opposite end of the cylindrical wall has a cylindrical ferrule which is open at its end and defines a rim. At least partially surrounding the ferrule is a collar. At least a portion of the collar is separated from the ferrule, leaving a gap between the ferrule and the collar. Thus, the entirety of the rim is devoid of any features that would interfere with a tight fit between the ferrule and a cap. The cap is attached by a hinge to the collar. The cap is selectably movable between open and closed positions in which the cap uncovers or covers the open end of the ferrule, respectively. The cap may have a skirt which engages with a mating portion of the collar to cover the ferrule completely. A tongue on the ferrule is engageable with a groove on the interior of the cap to retain the cap in the closed position when the cap is pivoted onto the top of the ferrule.

In another aspect, the present disclosure is directed to a package that has a hollow plastic tube for receiving the catheter. The tube has a wall of generally rectangular cross section and is closed at one end by a bottom wall. The opposite end of the tube's wall flares outwardly to an enlarged shoulder, the top land of which defines a sealing surface. A cap is attached to the tube by a hinge which allows the cap to move selectably between open and closed positons on the tube. The bottom of the cap has a sealing surface that engages that of the shoulder when the cap is closed to seal the interior of the package. The cap has mounted thereon a novel operating lever. The lever has a fulcrum attached to the cap and both an opening mechanism and a locking mechanism. The operating lever allows easy opening and closing of the packaging containing the catheter as well as easy access to the catheter. The package is opened by actuating a finger-sized flexible operating lever which is part of the cap. When the opening mechanism of the operating lever is depressed, it disengages the locking mechanism by pulling it away from the case body due to the intrinsic stiffness and elasticity of the plastic and the geometry of the pivot point. Actuation of the locking mechanism will also break a tamper evident feature placed between the locking mechanism on the cap and the case. The cap and the case may be molded as two separate components or one component.

Once the cap and the opening mechanism are actuated, the sterile seal between the cap and the case is breached. This seal may be overmolded or inserted into the case. It will possibly be made out of a thermoplastic or a thermoset or a combination of both.

In another aspect, the present disclosure is directed to a package that has a three-part container for receiving the catheter and a cap for closing the container. The three parts of the container include a hydration liner, a case, and a sleeve. Each of these three parts is basically an elongated, hollow tube, closed at one end and open at the other end, with the open end being selectably openable and closable by the cap. The hydration liner fits within the case which in turn fits within the sleeve. The hydration liner has window openings that permit hydration of a catheter stored in the liner. The cap may be either a flip cap that is removably attached to the case by a hinge, or it may be a twist-off cap that is removably attached to the case by threads. With either type of cap the sleeve and cap meet one another at a joint where the outer contours of the cap and sleeve match one another. In other words, the outer perimeters of the outer surfaces of the sleeve and cap match one another. Thus, the mechanical components such as threads, flanges, lips, grooves, seals and the like are hidden under one or both of the sleeve and cap. The matching outer contours of the sleeve and cap provide a smooth joint between the sleeve and cap and provide an aesthetically pleasing exterior appearance for the package.

In an alternate aspect, the present disclosure is directed to a package that has a two-part container that utilizes the case to provide the function of the hydration liner. The two parts of the container include a case and a sleeve. Once again each of the two parts is an elongated, hollow tube, closed at one end and open at the other end, with the open end being selectably openable and closable by the cap. The case fits within the sleeve. The case may have window openings that permit hydration of a catheter stored in the case. The cap may be either a flip cap or a twist-off cap. The sleeve and cap meet one another at a joint where the outer contours of the outer surfaces of the sleeve and cap match one another to provide an aesthetically pleasing exterior appearance for the package.

The package(s) of the present disclosure permit a user to retrieve the catheter from the case and re-capture it if they so wish. Once the cap is locked back into its closed position the package retains its original sealing qualities (meaning it will not leak), with a feature, such as a label that breaks upon opening, indicating that the product has been used. Another potential indication of use could be stress marks created in the hinge when the user first opens the product.

BRIEF DESCRIPTION OF THE DRAWINGS

FIG. 32 is a perspective view of an first alternate embodiment of the disclosure, showing the upper portion of the package tube, with the cap in an open position.

FIG. 33 is a longitudinal section taken along line 33-33 of FIG. 32.

FIG. 34 is a perspective view of the package of FIG. 32 from a different angle, with the open cap and ferrule aligned.

FIG. 35 is a side elevation view of the upper portion of the package of FIG. 32.

FIG. 36 is a vertical section taken along line 36-36 of FIG. 34.

FIG. 42 is a perspective view of a hydration liner that can be used in either of the packages of the present disclosure.

FIG. 43 is a top plan view of the hydration liner of FIG. 42.

FIG. 44 is a side elevation view of the hydration liner of FIG. 42.

FIG. 45 is a longitudinal section through the hydration liner of FIG. 42.

FIG. 46 is a perspective view of another embodiment of a hydration liner that can be used with the packages and assemblies of the present disclosure.

FIG. 47 is a side elevation view of the hydration liner of FIG. 46.

FIG. 48 is a longitudinal section through an assembly of the embodiment of the package shown in FIGS. 32-36 of the present disclosure, including a hydration liner and catheter therein.

FIG. 49 is an enlarged section of the package assembly, including the portion indicated by the circle labeled FIG. 49 in FIG. 48.

FIG. 50 is a perspective view showing a user connecting a urine collection bag to the catheter assembly.

FIG. 51 is a perspective view illustrating that the package assembly may be positioned in different orientations during connection to the urine collection bag.

DETAILED DESCRIPTION OF THE EMBODIMENTS

Figure 1:
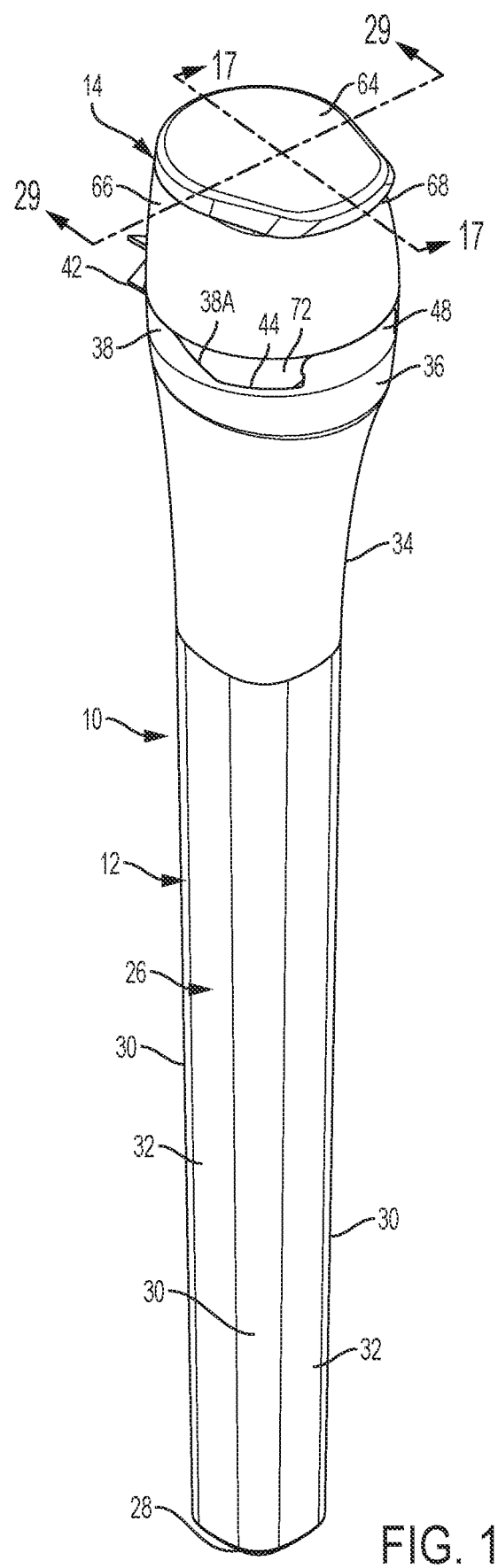
FIG. 1 is a perspective view of a first embodiment of the package of the present disclosure, with the cap in the closed position.
Figure 2:
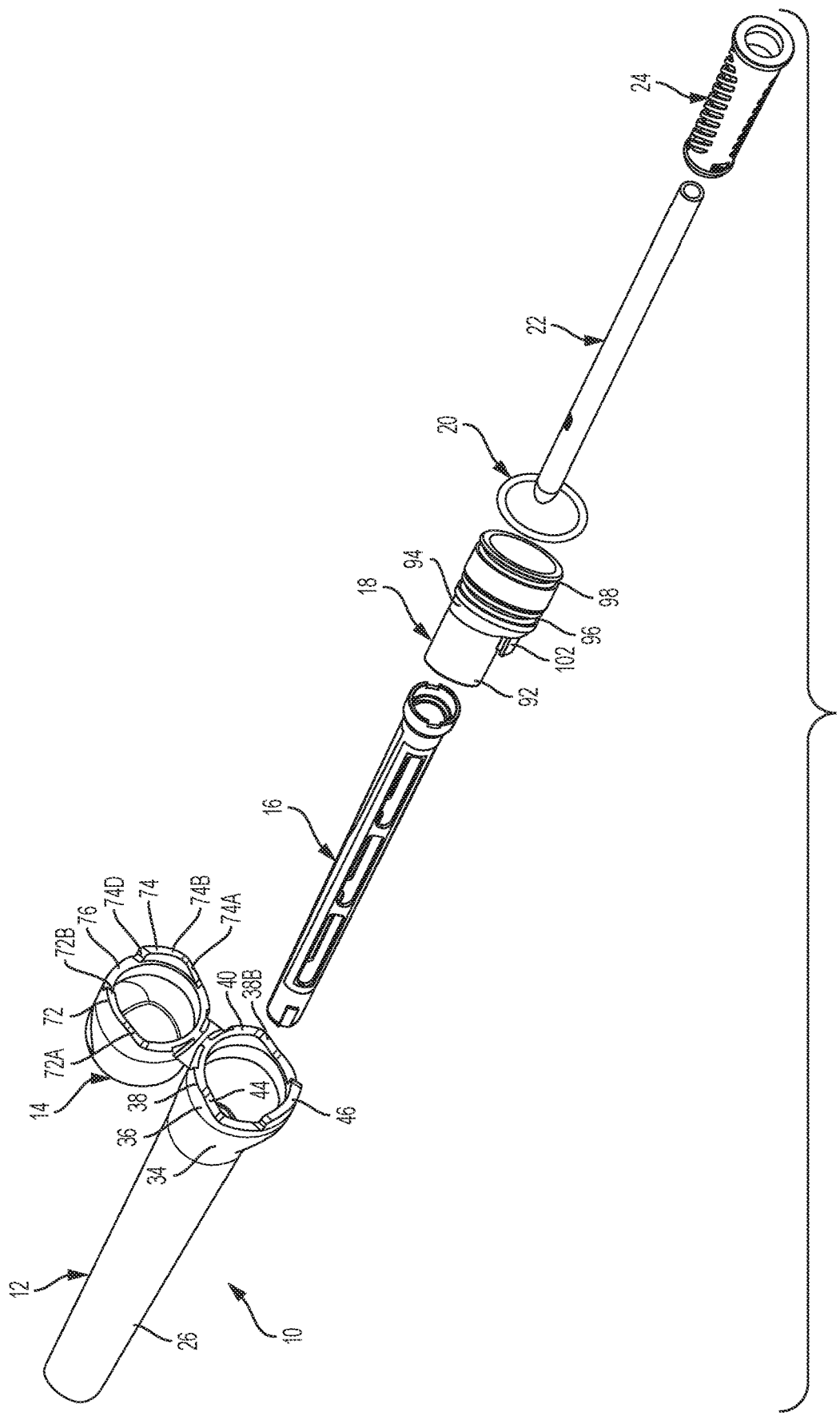
FIG. 2 is an exploded perspective view of the package of FIG. 1 from a different angle, with the cap shown in the open position on the case and the liner, case insert, O-ring, catheter tube and funnel removed from the case.
Figure 3:
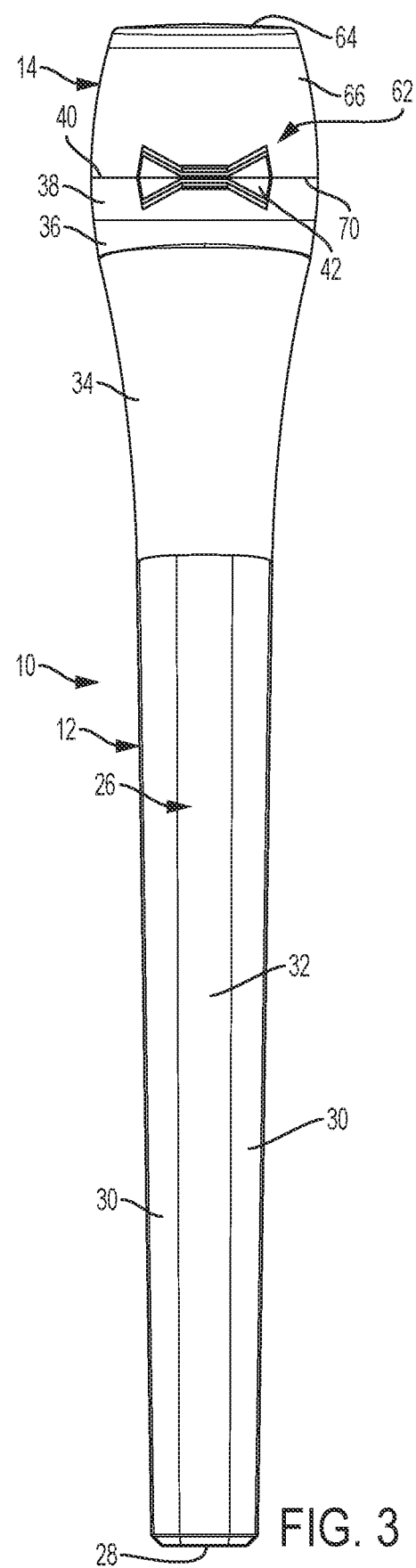
FIG. 3 is a rear elevation view of the package looking at the hinge joining the cap to the case.
Figure 4:
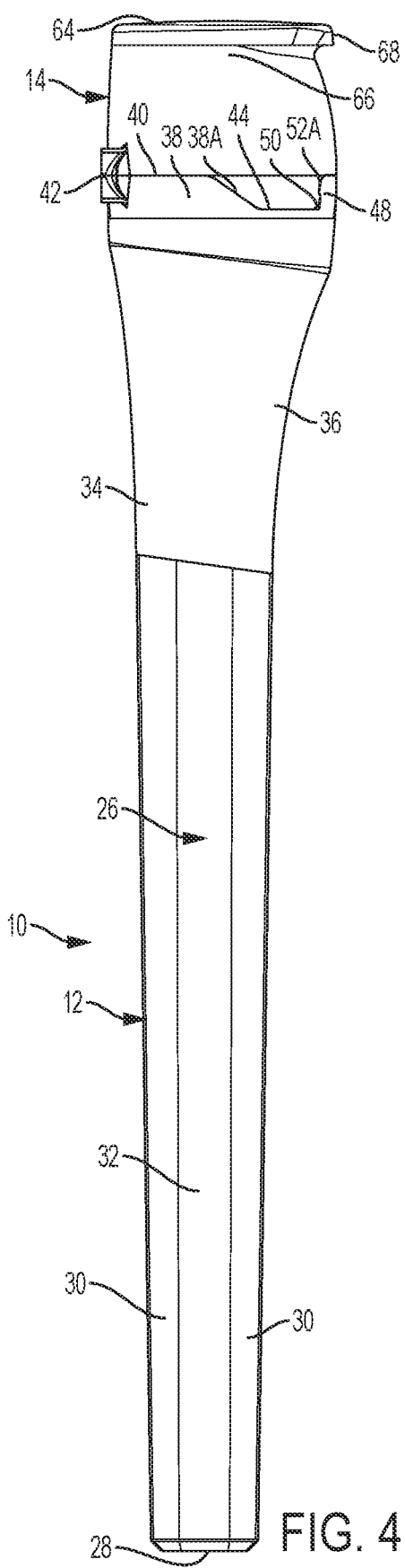
FIG. 4 is a left side elevation view of the package of FIG. 1.
Figure 5:
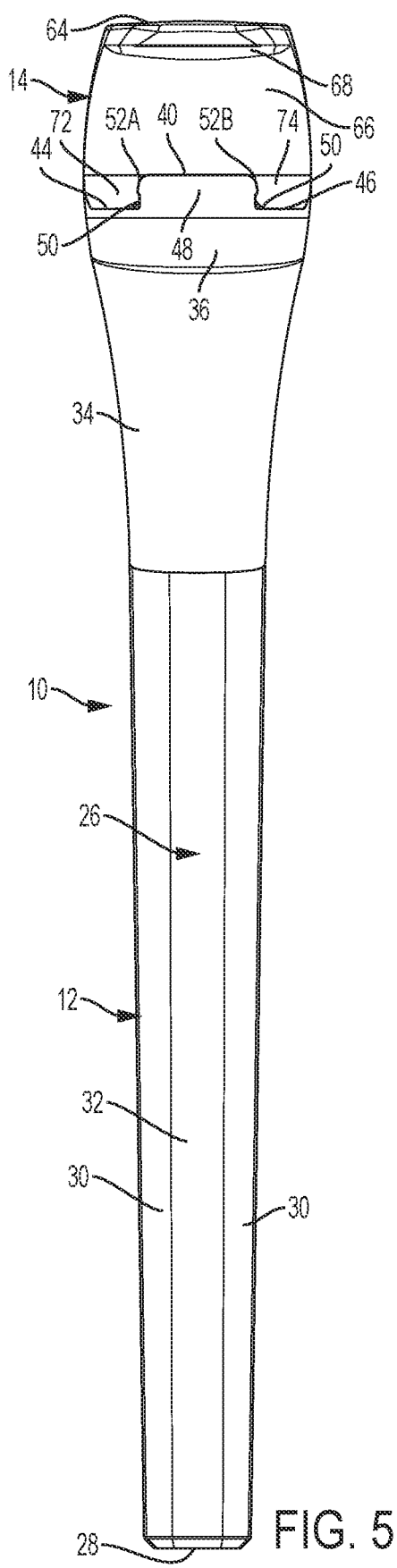
FIG. 5 is a front elevation view of the package of FIG. 1.
Figure 6:
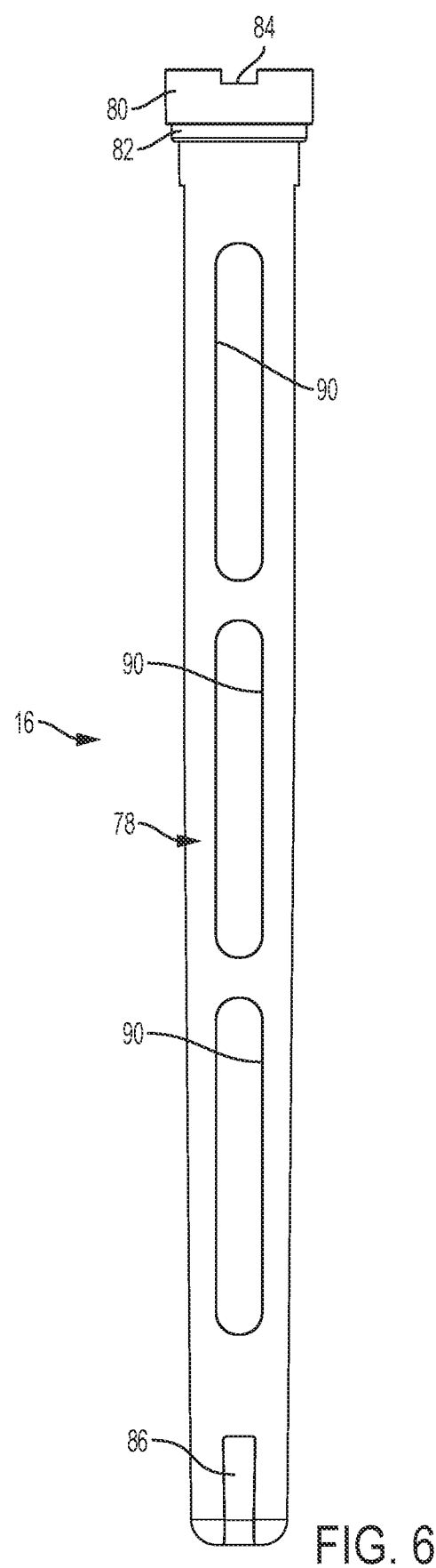
FIG. 6 is a front elevation view of the liner.
Figure 7:
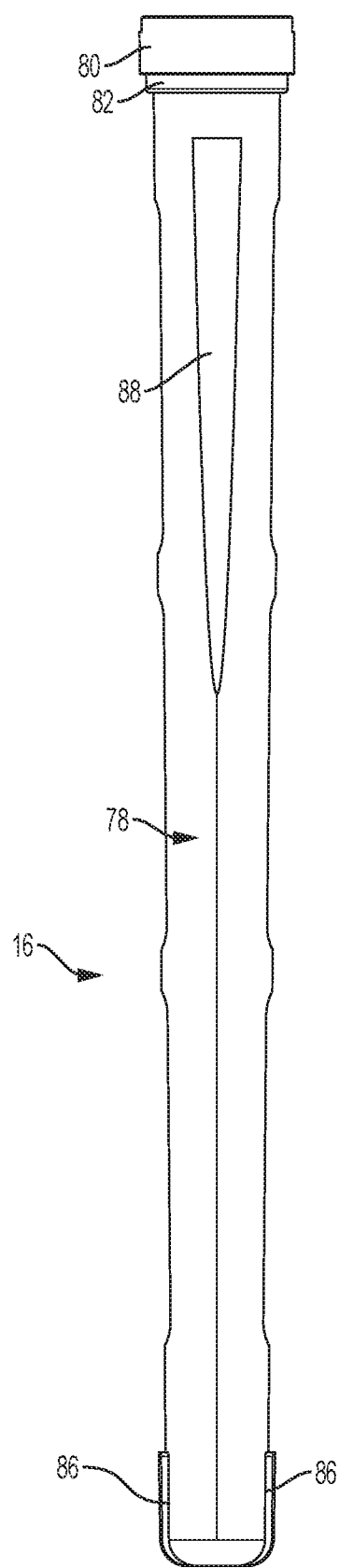
FIG. 7 is a side elevation view of the liner.
Figure 8:
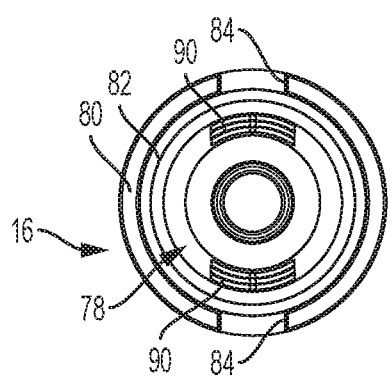
FIG. 8 is a top plan view of the liner.
Figure 9:
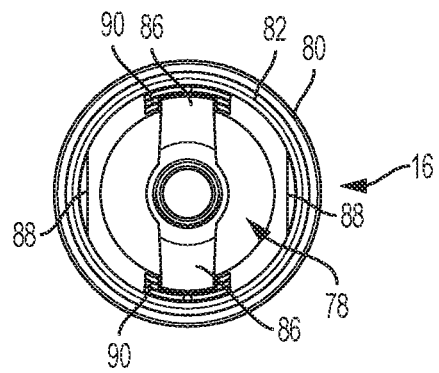
FIG. 9 is a bottom plan view of the liner.
Figure 10:
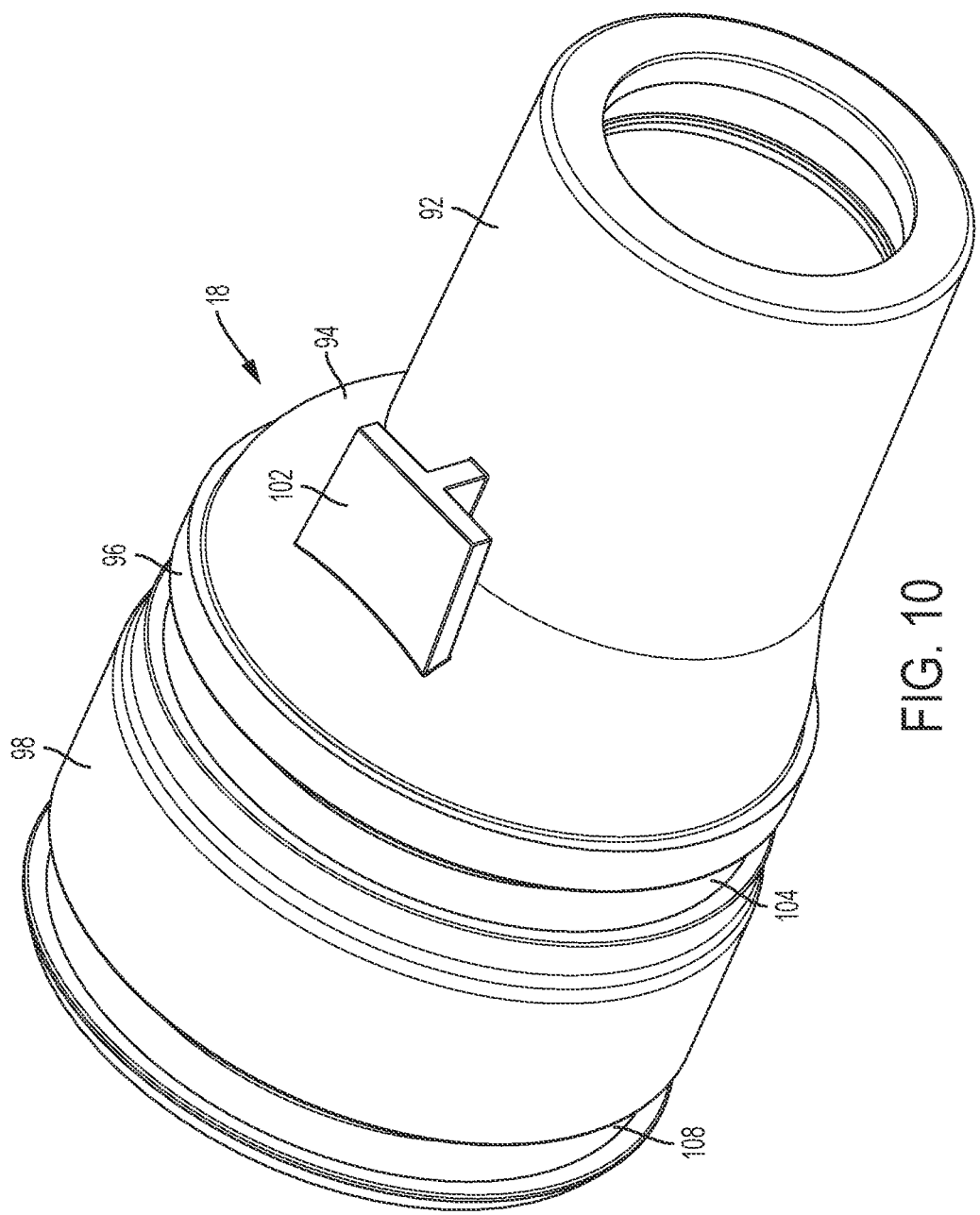
FIG. 10 is a perspective on an enlarged scale of a first embodiment of the case insert.
Figure 11:
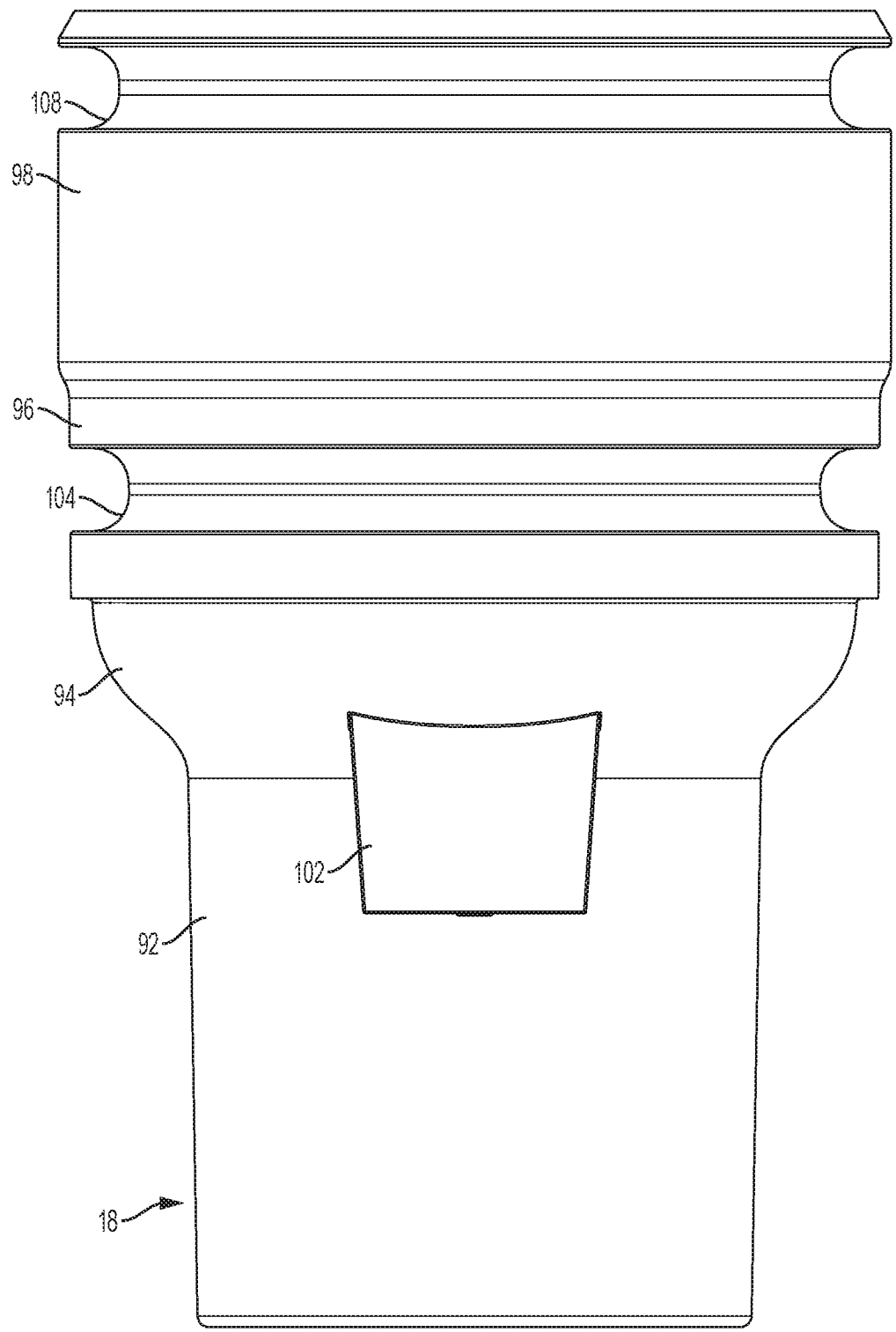
FIG. 11 is a front elevation view of the case insert of FIG. 10.
Figure 12:
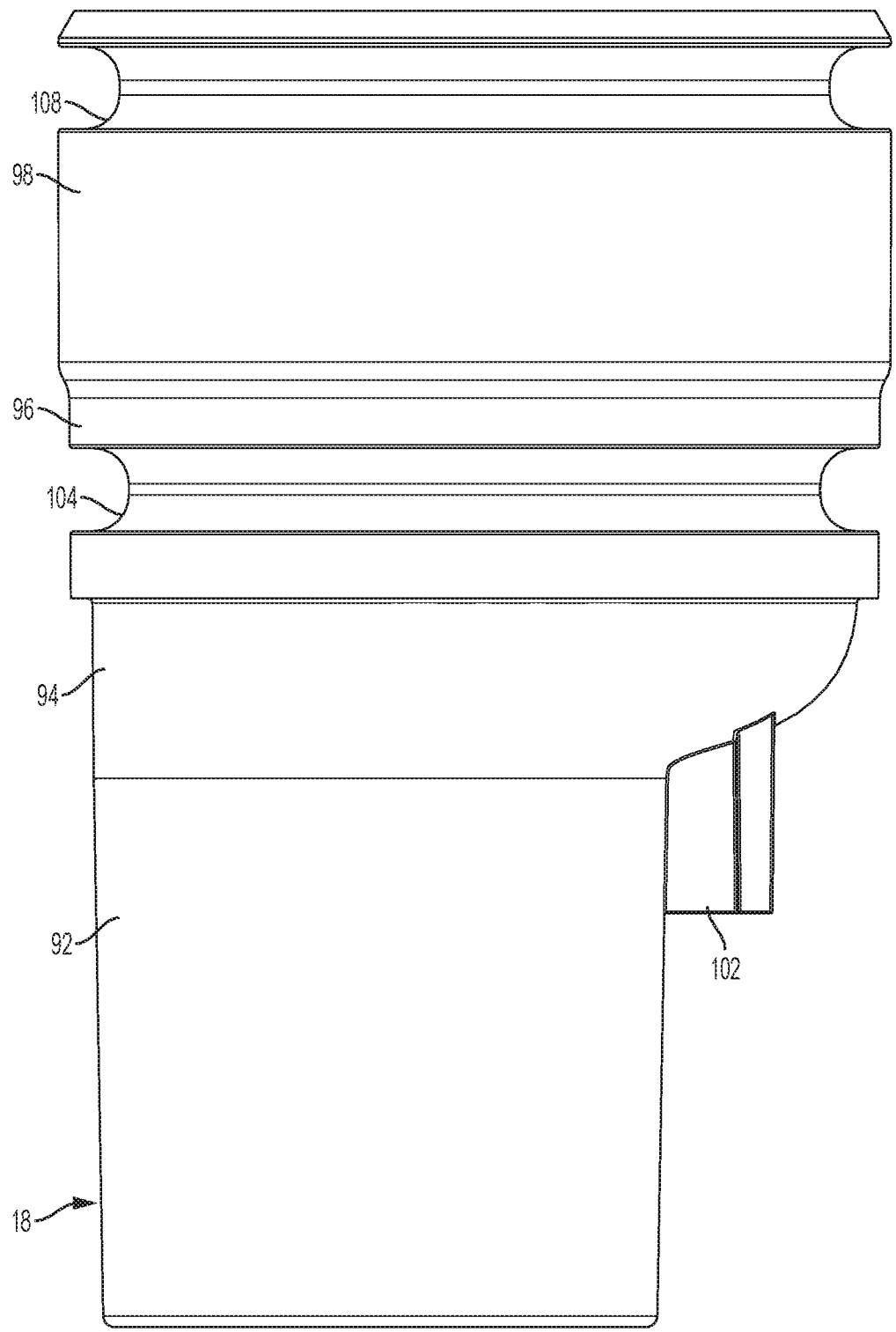
FIG. 12 is a left side elevation view of the case insert of FIG. 10.
Figure 13:
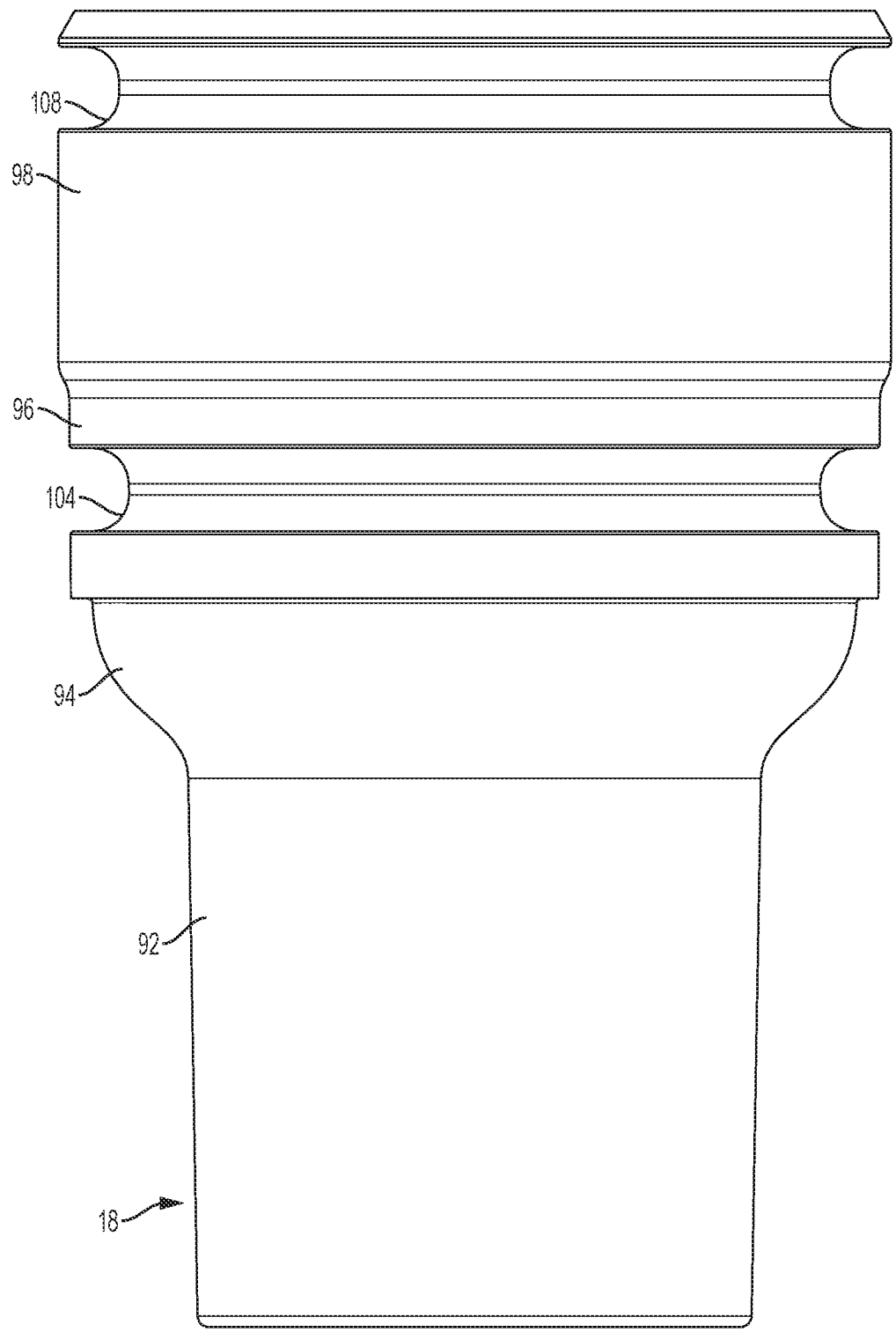
FIG. 13 is a rear elevation view of the case insert of FIG. 10.
Figure 14:
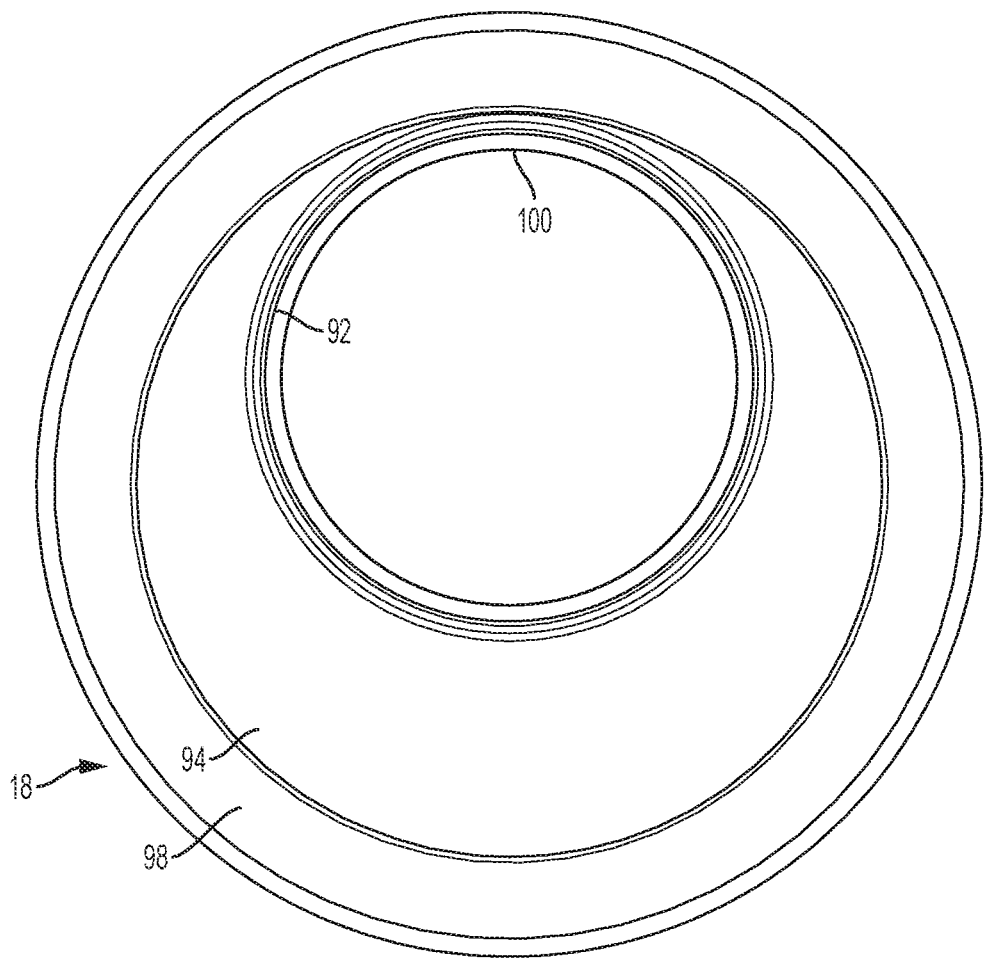
FIG. 14 is a top plan view of the case insert of FIG. 10.
Figure 15:
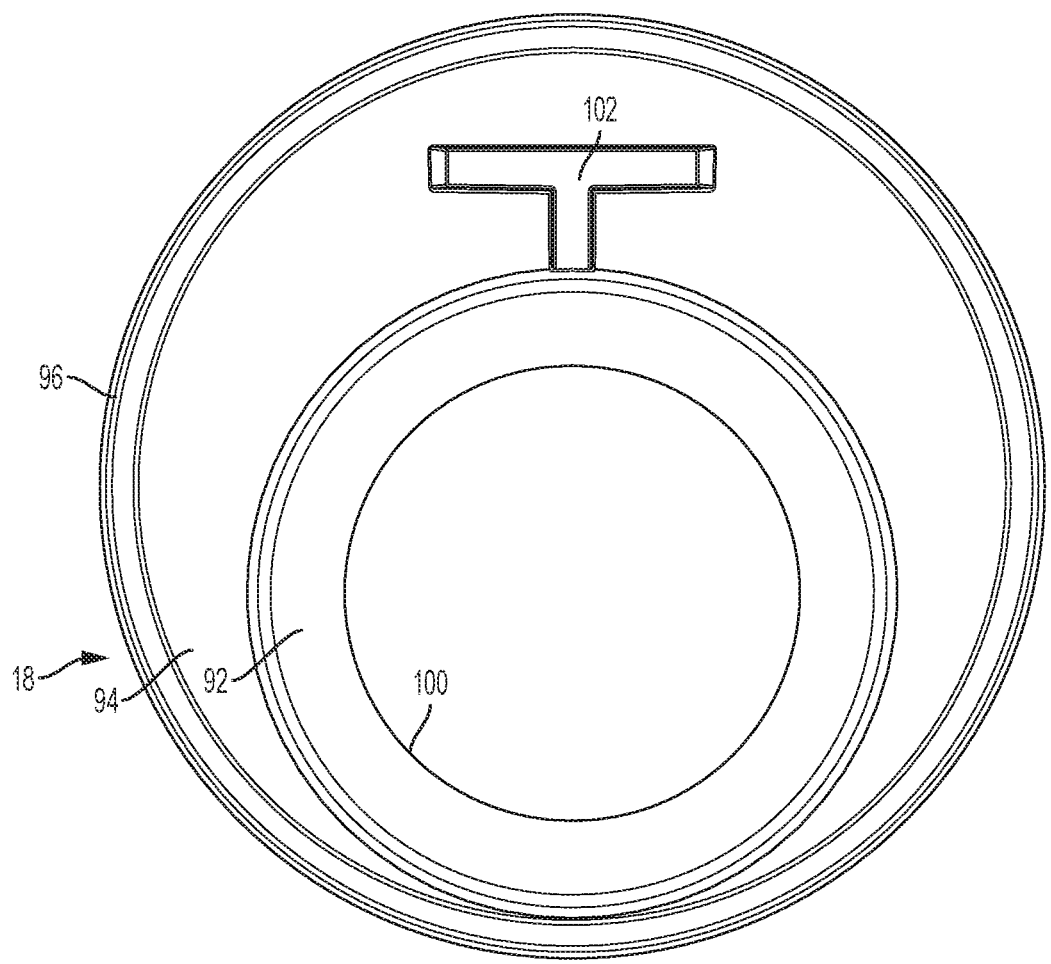
FIG. 15 is a bottom plan view of the case insert of FIG. 10.

The present disclosure is directed to packages for medical devices such as intermittent urinary catheters. Such a package is shown generally at 10 in FIG. 1. FIG. 2 shows the major components of the package including: a case 12, a cap 14, a hydration liner 16, a case insert 18, and an O-ring 20. FIG. 2 also illustrates the product contained within the package 10, namely, a urinary catheter which includes catheter tubing 22 and a funnel 24 attached to one end of the tubing 22.

Figure 19:
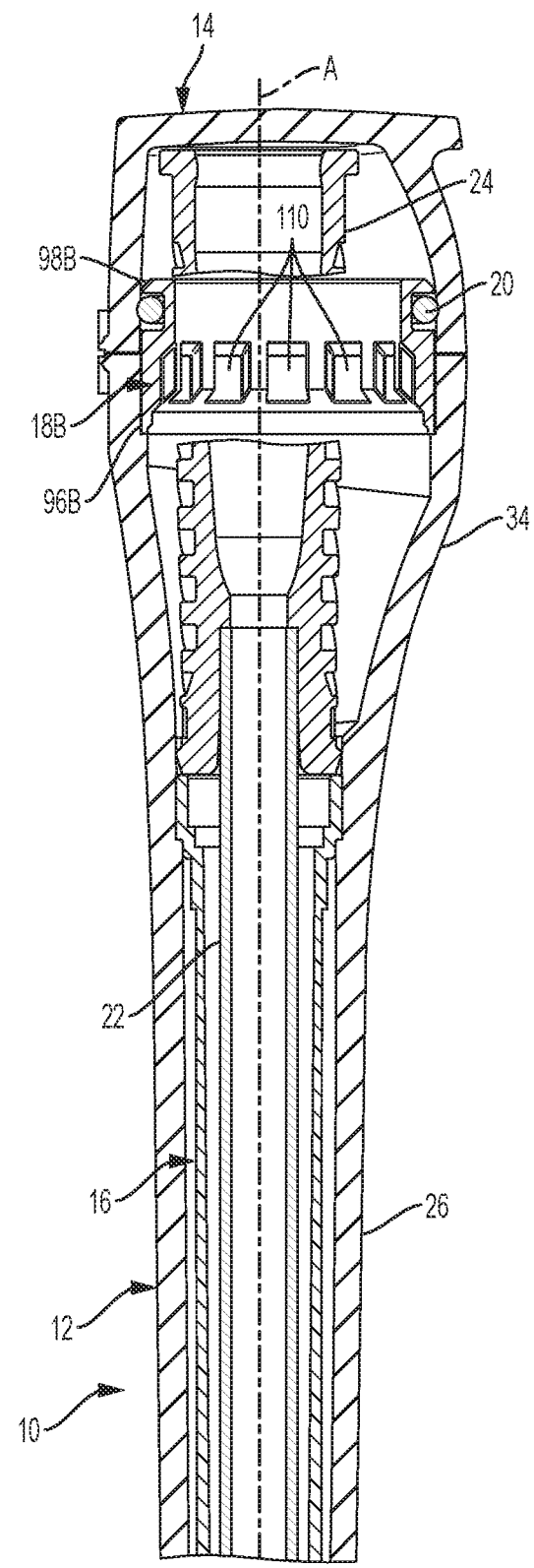
FIG. 19 is an enlarged section, similar to FIG. 17 but with a portion of the funnel broken away to show a further alternate embodiment of the case insert.

Details of the case 12 will now be described. The case is preferably molded from a suitable plastic material, such as polypropylene, although other materials could be used. The case includes a hollow tubular wall 26 which defines an axis A as seen in FIG. 19. The tubular wall 26 terminates at an end wall 28 that closes the bottom of the tubular wall. The interior surface of the tubular wall may be generally cylindrical. The exterior surface of the tubular wall 26 may have either a cylindrical or rectangular cross-sectional shape or the cross-section could be otherwise. As shown in FIG. 1, most of the exterior surface of the tubular wall 26 has a generally rectangular cross-section with large-radiused corners 30 joining four sides 32, although as shown even the sides 32 are not perfectly flat as they have a slight curvature on their outer surfaces. Above this rectangular portion the tubular wall 26 flares outwardly somewhat at a neck portion 34 to increase the diameter of the tube. The top of the neck 34 joins a cylindrical collar 36. The collar terminates at an open end of the tubular wall 26.

Figure 16:
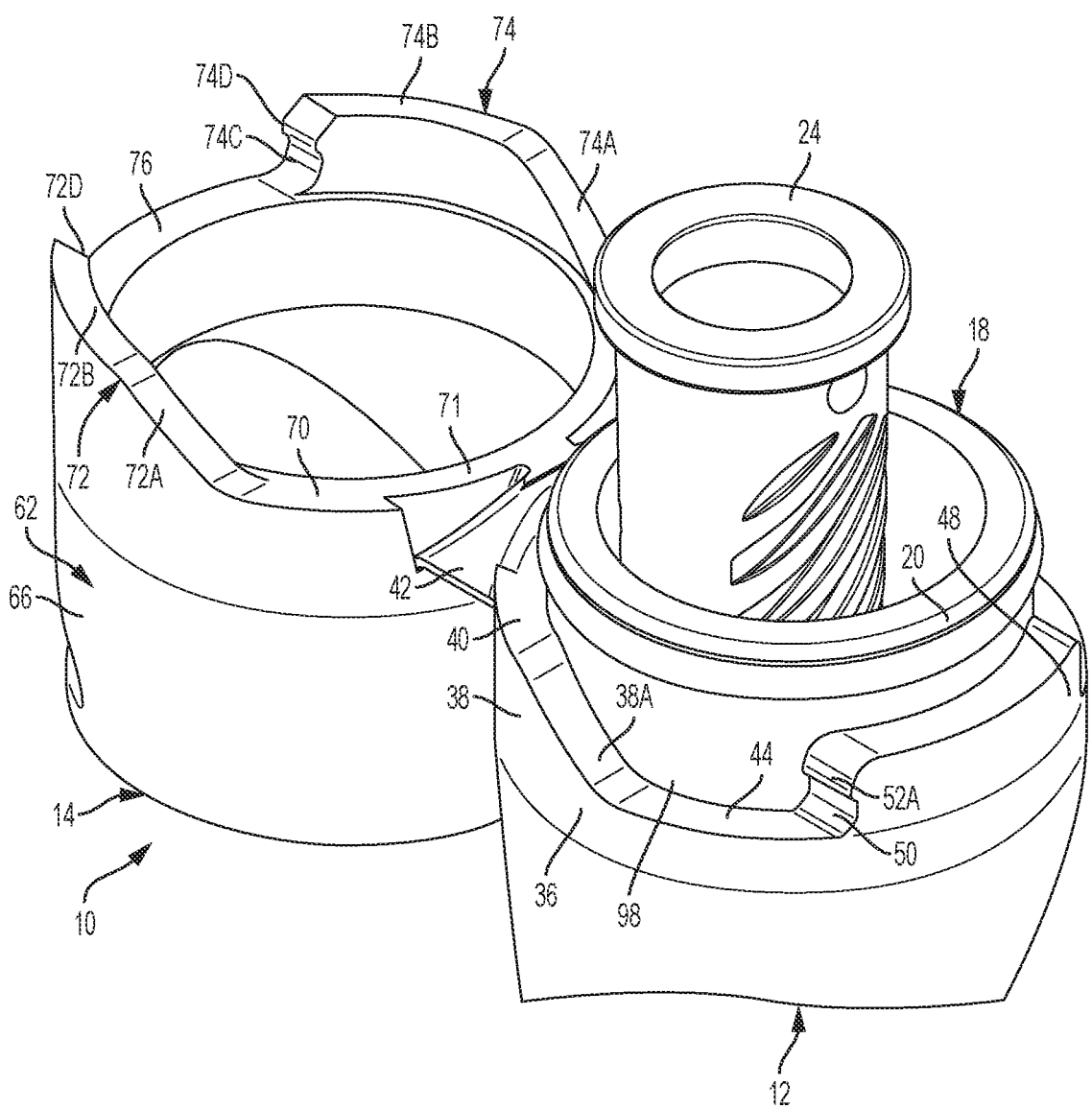
FIG. 16 is an enlarged perspective view of the upper portion of the package assembly with the cap in the open position, showing the catheter funnel protruding above the case insert.

Further details of the structure of the collar 36 are best seen in FIG. 16. The open end of the collar is cylindrical in shape and thus has circular internal and external edges. Thus, the external shape in this embodiment is circular and the external dimension would be an outside diameter. However, other external shapes could be used and the external dimension of a non-circular collar would not technically be a diameter. The thickness of the wall 26 creates a radial surface or top land 40 on the open end of the collar 36. The top land 40 is the radial surface at the greatest axial extent of the collar 36. In the orientation of the drawings, it is the highest or topmost radial surface. The collar 36 includes several features of varying axial extent. These include a shoulder 38, sloping portions 38A, 38B of the shoulder that define a pair of slots 44 and 46 and a detent 48 between the slots. The shoulder 38 extends arcuately about 180° and is centered near the mid-point of a hinge 42. The top land 40 at the shoulder 38 extends circumferentially in two directions from the mid-point of the hinge 42 and merges with gradually downwardly sloping portions 38A, 38B that join slots 44 and 46. The slots 44 and 46 terminate at a detent 48. The detent has a pair of undercuts 50 on its lateral edges that define ears 52A and 52B. The surfaces of the undercuts 50 and ears 52A, 52B, while not solely axial, include an axial component. The top land 40 at the detent 48 has the same height or axial location as the top land at the shoulder 38.

The hinge 42 as shown is a living hinge, but other hinge arrangements could be used. The hinge connects to the collar 36 and the cap 14 to permit selectable movement of the cap between open and closed positions.

Figure 17:
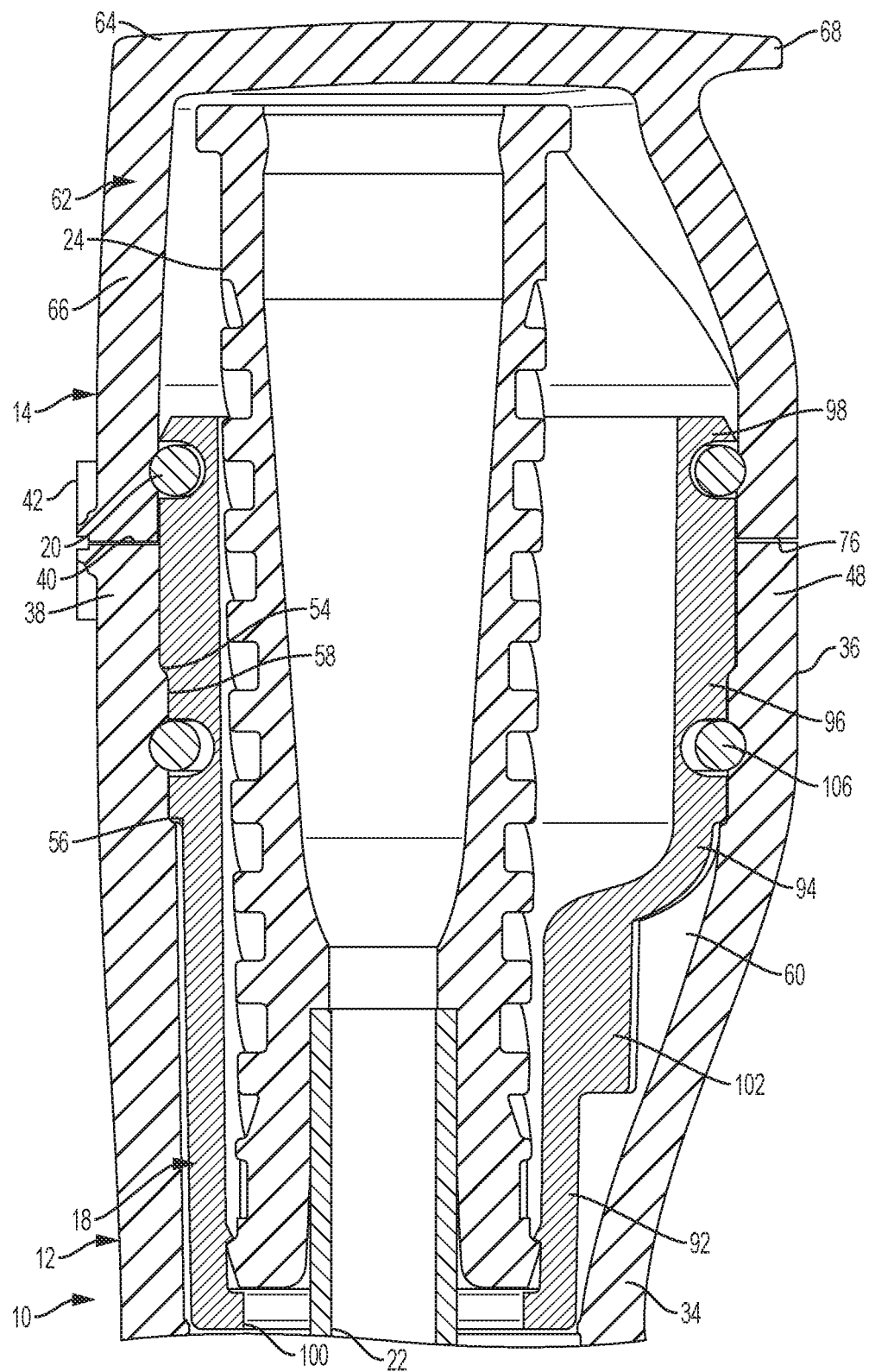
FIG. 17 is an enlarged section through the upper portion of the package, taken along the line 17-17 of FIG. 1.

Internal features of the case 12 are shown in FIG. 17 and include upper and lower radial beads 54 and 56. Between the beads the internal surface of the neck defines a sealing surface 58. Below the lower bead 56 there is an inwardly extending spacer 60 of limited arcuate extent on the interior of the neck 34 at the front only.

Details of the cap 14 will now be described. They are best seen in FIG. 16. The cap is hinged to the case 12 by hinge 42 and is selectably movable by a user between a closed position and an open position. FIG. 16 shows the cap in the open position. The cap 14 includes a generally cup-shaped shell 62 having a top wall 64 joined to a generally cylindrical side wall 66. The top wall 64 and side wall 66 may merge on one side of the cap to form a lip 68 that makes it easy for a user to engage the cap with a finger or thumb. Alternately, the lip 68 can be used to assist in opening the cap by placing the lip 68 in engagement with the edge of a table or similar surface and pulling the case downwardly. The hinge 42 is attached to the side wall 66. The side wall terminates at a bottom land 70. The bottom land is the radial surface that mates with the top land 40 of the collar 36. It is the portion of the open end of the side wall 66 having the least axial separation from the top wall 64. Like the top land 40, the bottom land 70 is cylindrical. Two latches 72, 74 extend from the bottom land 70 axially away from the top wall 64 of the cap. When the cap is in the closed position the latches extend or project downwardly from the bottom land 70 of the cap. Each latch has a sloping edge 72A, 74A that extends from a sill portion 71 of the bottom land 70 to a crest surface 72B, 74B of the latch. The facing edges of the latches 72, 74 have undercuts 72C, 74C that form tabs 72D, 74D and define a gap 76 in the cap between the latches. Similarly to the undercuts 50 and ears 52A, 52B, the undercuts 72C, 74C and tabs 72D, 74D include an axial component.

When the cap is closed the bottom land 70 of the cap 14 mates with the top land 40 of the collar 36. That is, the sill 71 engages the shoulder 38, and the gap surface 76 engages the top land 40 on the detent 48. Also, the sloping edges 72A, 74A engage the sloping portions 38A, 38B, and the crests 72B, 74B engage the slots 44 and 46. Finally, as the cap closes the tabs 72D, 74D of the cap snap past the ears 52A, 52B of the detent 48 to allow the detent to end up disposed in the gap 76. That is, ears 52A, 52B of the detent end up disposed in the undercuts 72C, 74C of the latches 72, 74. Similarly, the tabs 72D, 74D end up disposed in the undercuts 50A, 50B of the detent 48. During closing or opening movement of the cap the tabs 72D, 74D and ears 52A, 52B interfere with one another but flex slightly to allow these parts to slide past one another in either an opening or closing direction. Thus, when the cap is closed the cap and collar present a smooth, but interlocking external surface on the top of the package. Furthermore, when the cap is closed the axial components of the latches 72, 74 and detent 48 end up adjacent one another which will prevent any lateral forces on the cap from dislodging the cap or degrading the seal between the cap and O-ring, as will be explained below. By lateral forces it is meant forces in a plane roughly parallel to that defined by the mating top and bottom lands 40 and 70 of the case and closed cap. This would include forces tangential to the cap or forces acting on the cap in a circumferential direction. That is, the rear portion of the cap is held fixed against lateral loads by the hinge 42. The front portion of the cap is held fixed against lateral loads by engagement of the detent 48 with the latches 72 and 74.

Turning now to FIGS. 6-9, a hydration liner is shown generally at 16. The hydration liner is sized to fit within the case 12. The liner 16 rests within the tubular wall of the case with the catheter's tubing 22 (but not the funnel 24) within the liner 16. The liner defines a space between the liner's exterior surface and the case's interior surface within which a hydration mechanism, such as liquid water may reside. This permits hydration of the surface treatment on the catheter tubing.

The liner 16 may be a relatively rigid plastic such as LDPE or HDPE or other relevant materials. The liner has a generally hollow tube 78 which is open at the top and closed at the bottom. At its upper end the tube 78 has a seat of slightly increased outside diameter compared to the remainder of the tube 78. The seat is sized to engage the internal wall of the package case. The seat includes an upper portion 80 of maximum outside diameter and a lower portion 82 which has a stepped down outside diameter compared to the upper portion. The upper portion may engage a radially extending ledge on the inside surface of the case to hold the liner in place. A keyway or slot 84 is formed in the upper portion 80 of the seat. There are locating pads 86 at the bottom of the tube 78 which are engageable with the internal walls of the case to fix the bottom end of the tube. A pair of flats 88 are formed on opposite side of the exterior of the tube 78. The keyway 84, locating pads 86 and flats 88 help orient the liner in place during the assembly process. The walls of the liner tube 78 have formed therein one or more passages or windows 90. The windows will be covered with a patch (not shown) of liquid impermeable/vapor permeable material such as, but not limited to, calcium carbonate. The patches will allow passage of water vapor (for hydration of the catheter) but will block passage of liquid water droplets. The patch might be heat sealed around the perimeter of the windows 90.

Turning to FIGS. 10-15, details of the case insert 18 will now be described. This embodiment of the case insert has four portions or regions, a sleeve 92, a transition section 94, a collet 96 and a projection 98. The lowest of these is the cylindrical sleeve 92. It has a radially inwardly directed foot or flange 100 at the bottom thereof. The sleeve at its upper end joins the transition section 94. The transition section flares out prominently toward the front of the insert and less so to the rear. The flaring of the transition section 94 results in the top of the transition section and the collet 96 having an increased outside diameter compared to the sleeve. At the junction of the exterior surfaces of the sleeve 92 and the transition section 94 and at the front thereof is a T-shaped bumper 102. The bumper is engageable with the spacer 60 in the neck 34 of the case 12 to fix the sleeve 92 and transition section 94 in the case 12 in a radial direction.

The top of the transition section 94 joins the collet 96. The collet is cylindrical and fits inside the collar 36 of the case's tubular wall 26. In this embodiment the collet has a circumferential groove 104 on its exterior surface. The groove receives an O-ring 106 (FIG. 17). The O-ring 106 engages the sealing surface 58 in the collar 36 to prevent any leakage of a hydrating medium, e.g., liquid water, from the lower portion of the case 12.

The top of the collet 96 joins the projection 98. The projection is that portion of the case insert 18 that protrudes above the top land 40 of the collar 36. Like the collet 96, the projection 98 is cylindrical and it has essentially the same inside and outside diameters as the collet. Near the top edge of the projection 98 there is a circumferential groove 108 on its exterior surface. This groove receives the O-ring 20. As seen in FIG. 17, the O-ring 20 engages the internal surface of the cap's side wall 66 to prevent any leakage of liquids from the interior of the case insert 18. The O-ring 20 provides a dynamic seal in that the cap can be opened and closed numerous times and each time the cap is closed the O-ring 20 will again prevent any escape of moisture from the package.

One of the advantages of the case insert is that it provides the option of making it from a different material than that of the case. If desired, the case can be made to be very stiff because the case insert material is not limited by the needs of the case and cap material. The latter must be soft enough to produce a good living hinge. But with an entirely separate case insert, it can be made quite robust and therefore it provides a good base for the O-ring 20. For example, the case insert could be made of a stiff HDPE or a grade of polypropylene that is harder than the polypropylene of the case. Alternately, the case and case insert could be made of the same type of polypropylene. Mounting the O-ring on the case insert also eliminates any need to place a seal or sealing material in the cap. Furthermore, greater dimensional tolerance can be held since the case insert is a single component, as opposed to being part of the case, which itself is already a complex mold.

There are several alternative methods for assembling the case 12 and case insert 18. A first method is to mold the case as an overmold on the case insert. This would be a two shot process. The case insert itself is molded in shot one. Then the case is overmolded around the case insert in shot two. A second method is a one shot assembly. This would be a one shot process. The case and case insert are both made in one shot. A third method is a separate component assembly process. In this process the case and case insert are individually molded as separate components and then assembled together. That is, the case insert would be inserted into the case during the assembly process.

FIG. 17 illustrates the interactions among the parts at the top of the case 12. The bottom the case insert's collet 96 sits on the lower bead 56 in the neck 34 of the case. The T-shaped bumper 102 engages the spacer 60 in the neck 34. The lower O-ring 106 engages the sealing surface 58. The upper O-ring 20 engages the interior of the cap 14. The catheter tubing 22 is supported in the bottom of the funnel 24. The bottom of the funnel is supported by the foot 100 of the case insert's sleeve 92.

Figure 18:
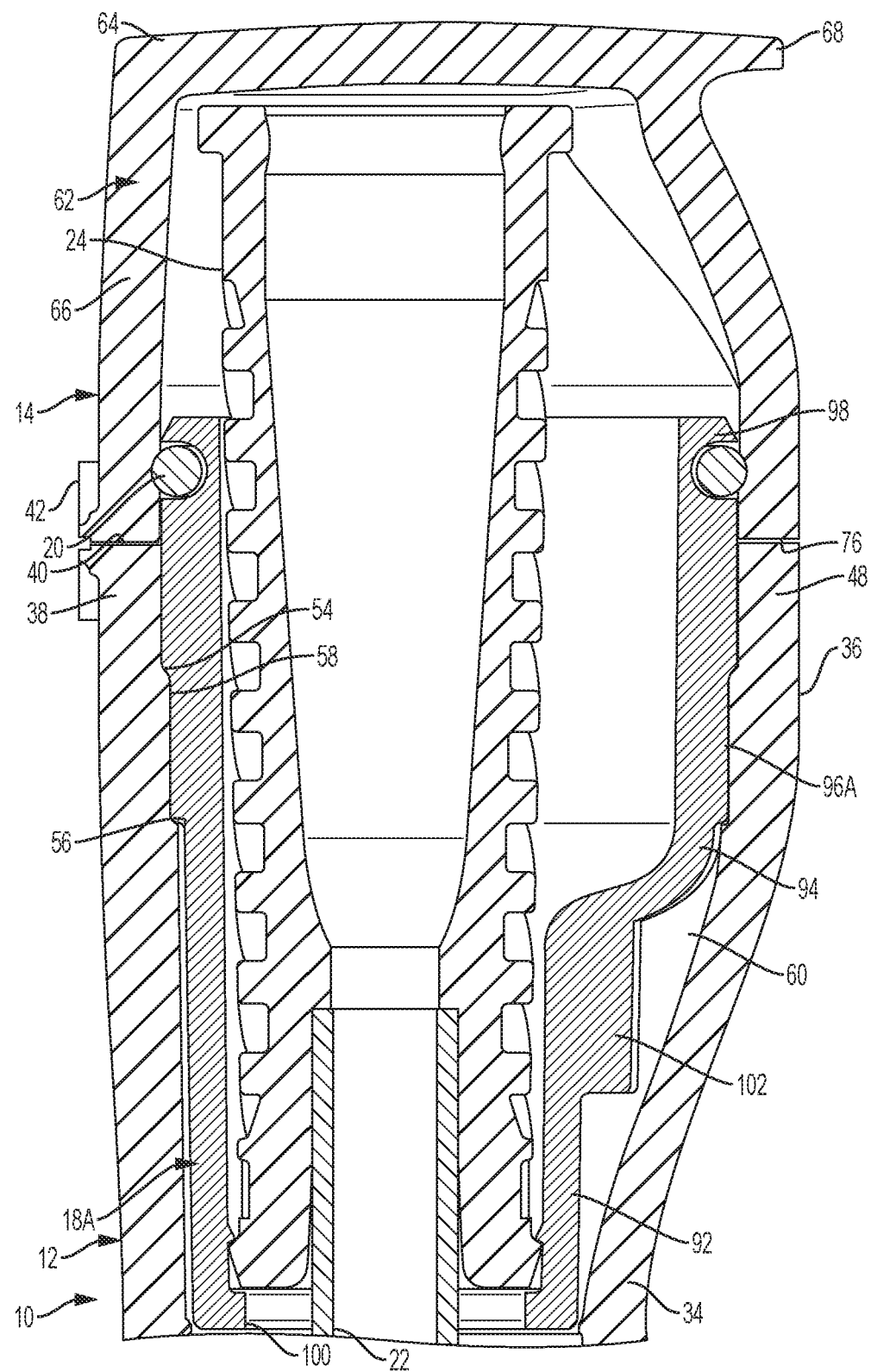
FIG. 18 is an enlarged section, similar to FIG. 17 but showing an alternate embodiment of the case insert.

FIG. 18 illustrates an alternate embodiment of the case insert at 18A. This embodiment deletes the lower O-ring and the groove on the collet 96A therefor. Instead of the insert-to-case seal being made by an O-ring, it is made by an interference fit between the outer surface of the collet 96A and the sealing surface 58 of the collar 36. The interference fit may be enhanced by ultrasonically welding the case insert 18A to the case 12.

FIG. 19 shows another alternate embodiment for a case insert 18B. In this embodiment both the sleeve and transition section of the previous case inserts have been deleted. Case insert 18B has just a collet 96B and a projection 98B. The projection 98B and the O-ring 20 therein are similar in structure and function to the previously described embodiment. The collet 96B is axially shorter than the collets 96 and 96A. Collet 96B extends only as far as, and rests on, the upper radial bead 56 in the neck 34. Also, a series of indentations are cut on the internal surface of the collet 96B to define a series of axially-extending ribs 110. The indentations reduce portions of the wall thickness which makes the part easier to mold.

Figure 20:
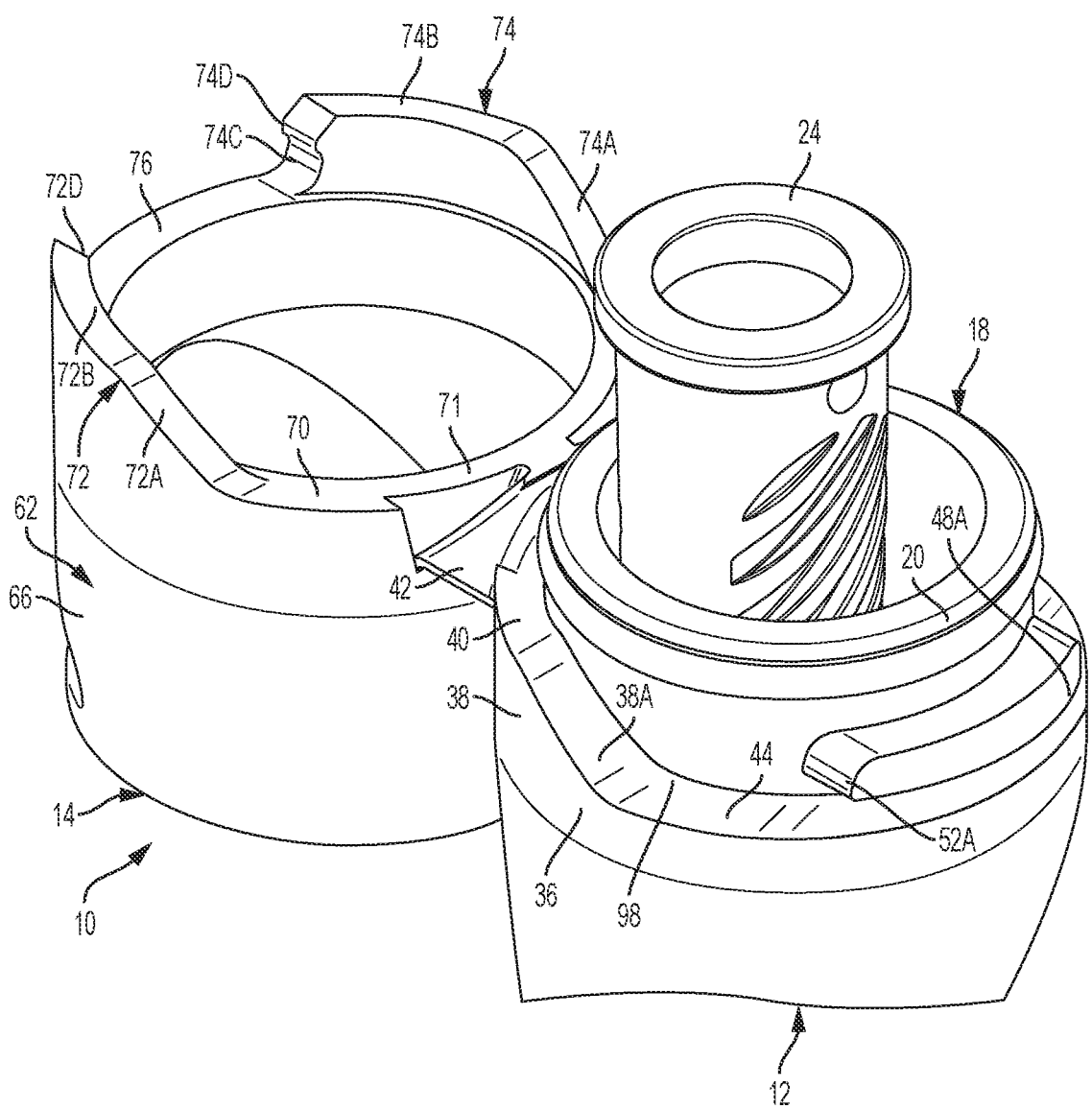
FIG. 20 is a perspective view similar to FIG. 16 but showing an alternate embodiment of the detent wherein the detent is attached to the case insert instead of to the case.

FIG. 20 illustrates an alternate arrangement for a detent 48A. This detent is similar to detent 48 in that it has a pair of ears, one of which is seen at 52A, that are located so as to flexibly engage the tabs 72D, 74D of the cap's latches 72, 74 when the cap 14 moves between its open and closed positions. But instead of the detent 48A being formed on the case and extending axially, the detent 48A is attached to the external surface of the case insert 18A and extends radially outwardly therefrom. There is open space underneath the detent 48A and thus the detent is separated from the top land 40 of the case 12. The outer circumference of the detent 48A still has the same outside diameter as the top of the collar 36 and the bottom of the cap side wall 66. Accordingly, when the cap 14 is closed the mating detent and cap surfaces present a smooth, continuous outer surface. When the cap is closed the latches 72, 74 snap around the detent 48A with the tabs 72D, 74D ending up tucked under the ears 52A, 52B so that the ears resist unintentional opening forces and retain the cap closed. However, the ears and tabs will flex upon application of an intentional opening force to allow the cap to move from the closed position to the open position. Also, while the detent 48A is shown as a single piece, it could be formed as two separate pieces with an intermediate hiatus, so long as the positions of the ears 52A, 52B remain the same. Making the detent 48A as two pieces may make each individual piece more flexible for purposes of snapping past the moving tabs of the cap.

Figure 21:
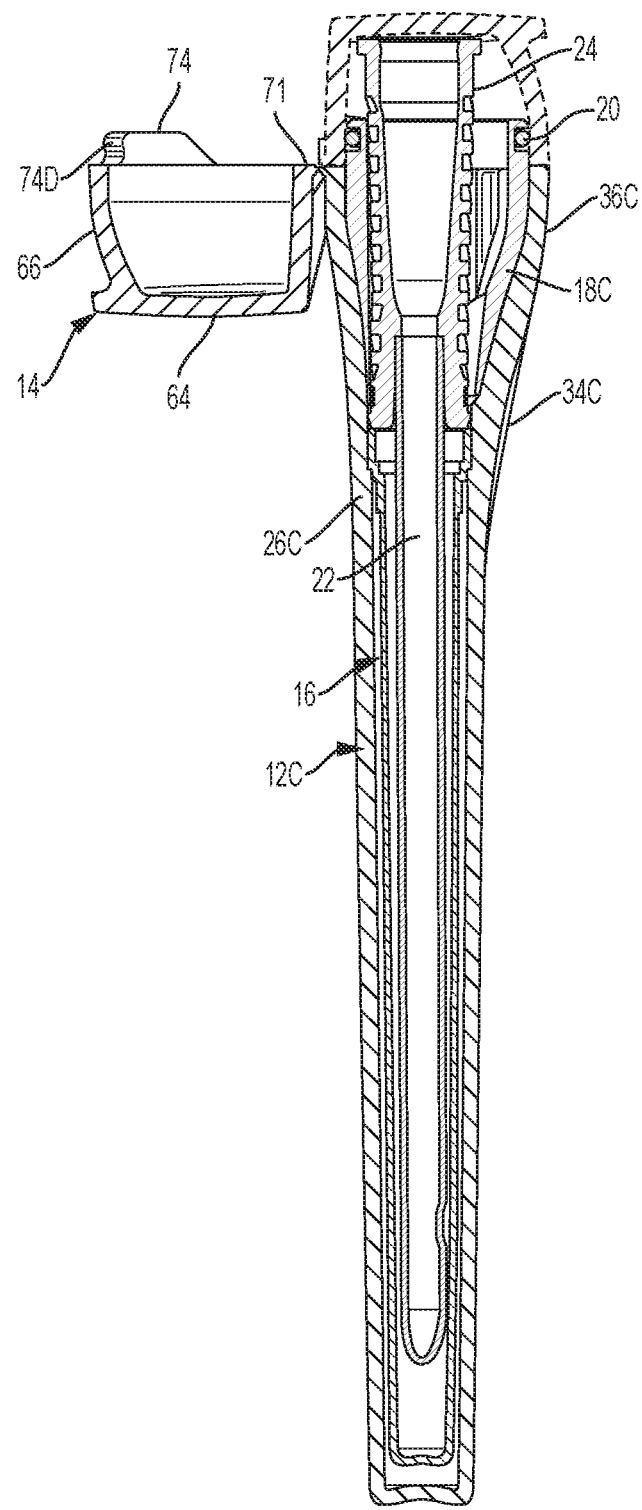
FIG. 21 is an enlarged section through the package, taken along line 17-17 of FIG. 1 and showing an alternate embodiment of the case insert.
Figure 22:
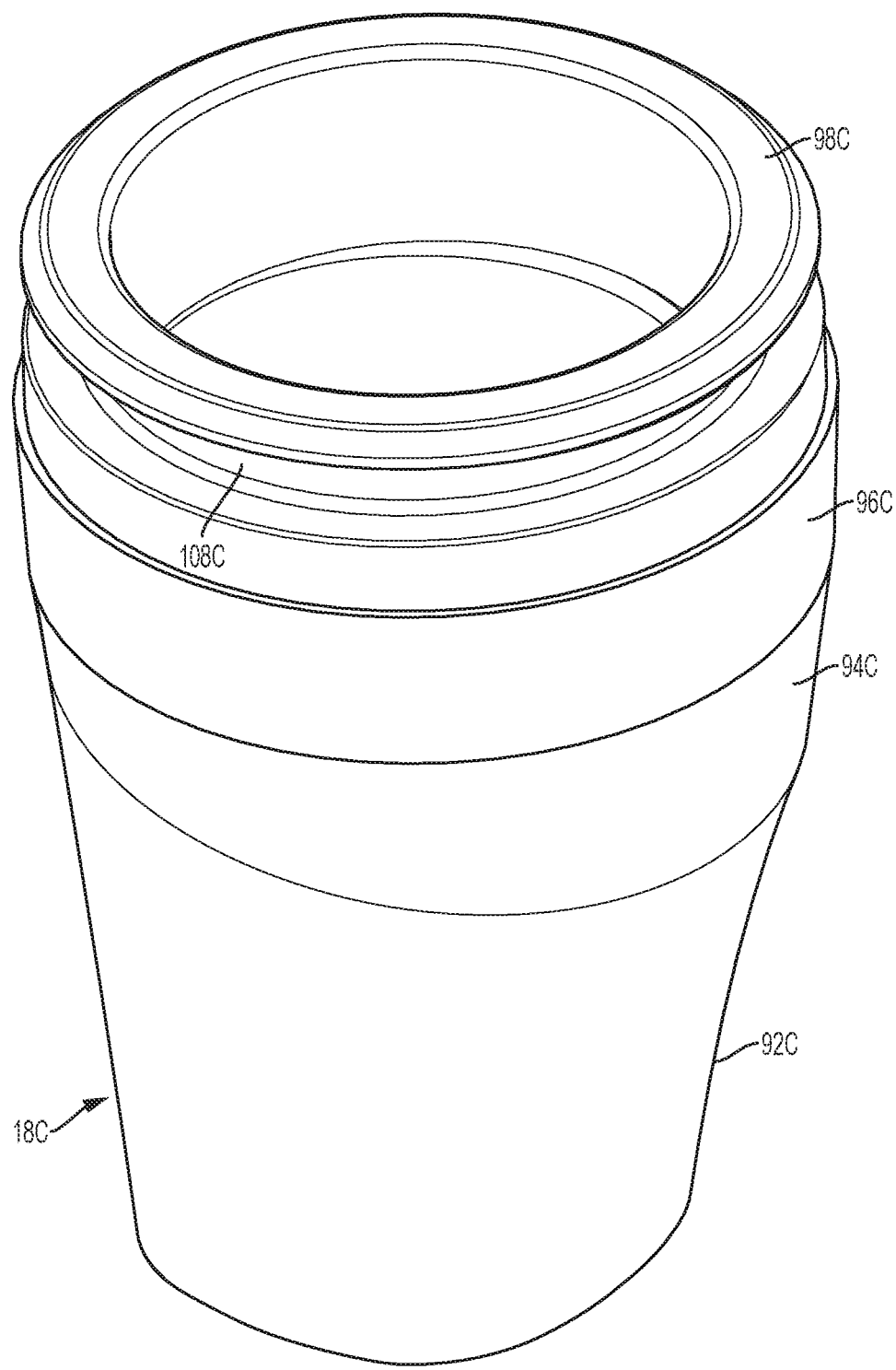
FIG. 22 is a perspective view of the case insert of FIG. 21.

FIGS. 21 and 22 show another alternate embodiment for a case insert 18C. The case insert 18C lends itself to the possibility of manufacturing it and the case 12C in a one-shot molding process. However, case insert 18C can also be manufactured in a two-shot molding process. Or it could be made entirely separately from the case and then the separate case and case insert 18C are assembled together. Thus, the design of case insert 18C affords complete flexibility in the choice of its manufacturing process. Case insert 18C is generally similar to the case insert 18A of FIG. 18 in that it has a sleeve 92C, a transition section 94C, a collet 96C and a projection 98C, with a groove 108 on the external surface of the projection for receiving a single O-ring 20. Case insert 18C differs from case insert 18A in that the external surface of the transition section 94C and the collet 96C closely adhere to the internal surface of the case's tubular wall 26C, particularly at the neck 34C and collar 36C. Thus, case insert 18C does not have a piece like the bumper 102 and the case 12C does not have a piece like the spacer 60 on the interior of the neck.

Figure 24:
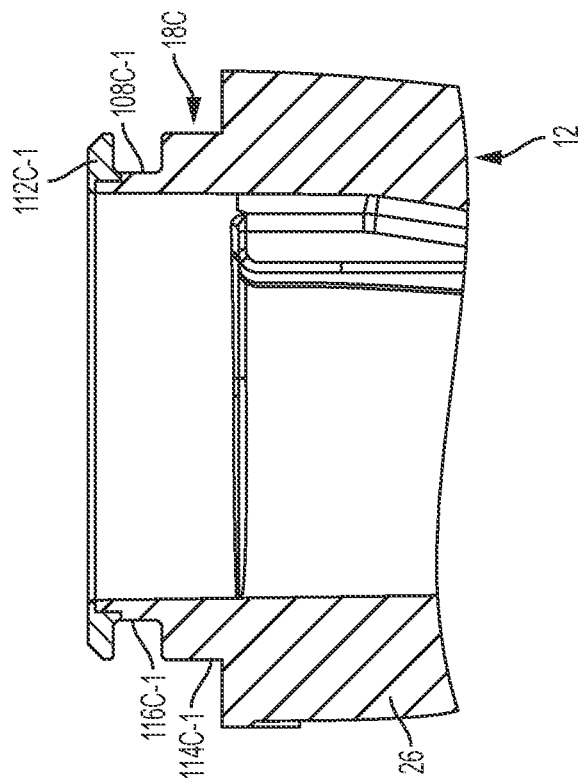
FIG. 24 is a section taken generally along line 24-24 of FIG. 23.
Figure 23:
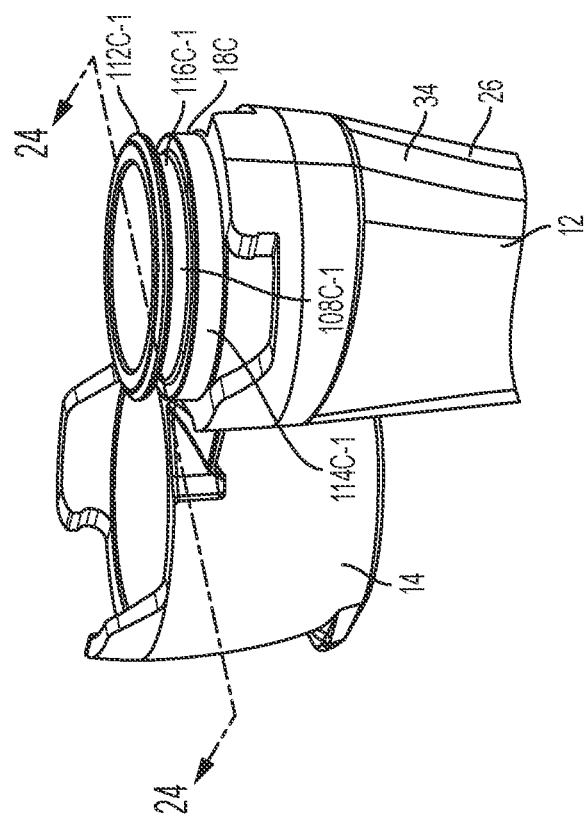
FIG. 23 is a perspective view of the upper portion of the package assembly with the cap in the open position, showing an alternate embodiment of the case insert.

FIGS. 23 and 24 illustrate a first variation of the case insert 18C. In the embodiment of FIGS. 23 and 24 a case insert 18C-1 differs from case insert 18C only in that the O-ring groove 108C-1 is formed from two separate components. The O-ring groove is defined by upper and lower flanges 112C-1 and 114C-1, respectively. The upper and lower flanges join a root 116C-1 of the groove. In this embodiment the root 116C-1 and the lower flange 114C-1 are integrally formed during a molding operation. But the upper flange 112C-1 is made as a separate part and attached to the root portion 116C-1 at a later step in the assembly process. It may be attached by ultrasonic welding, for example, although other methods could be used.

Figure 25:
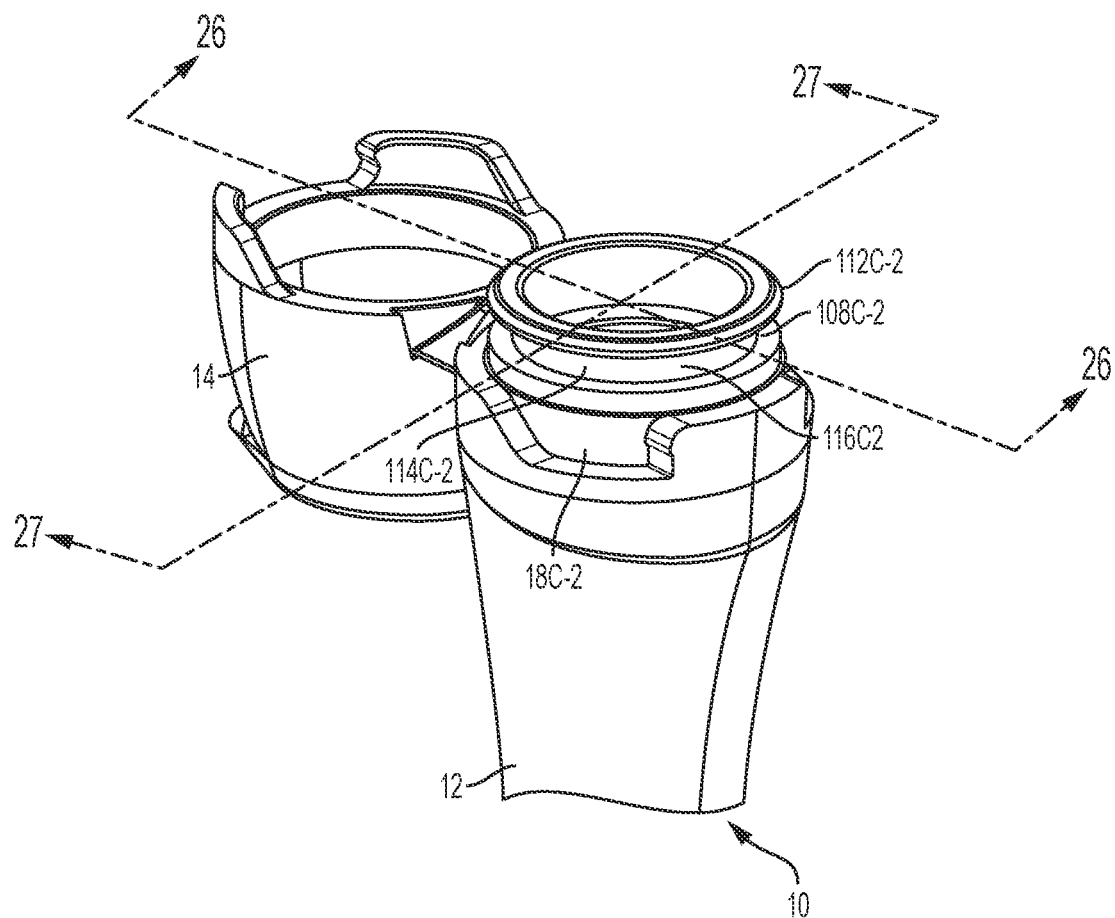
FIG. 25 is a perspective view of the upper portion of the package assembly with the cap in the open position, showing a further alternate embodiment of the case insert.
Figure 27:
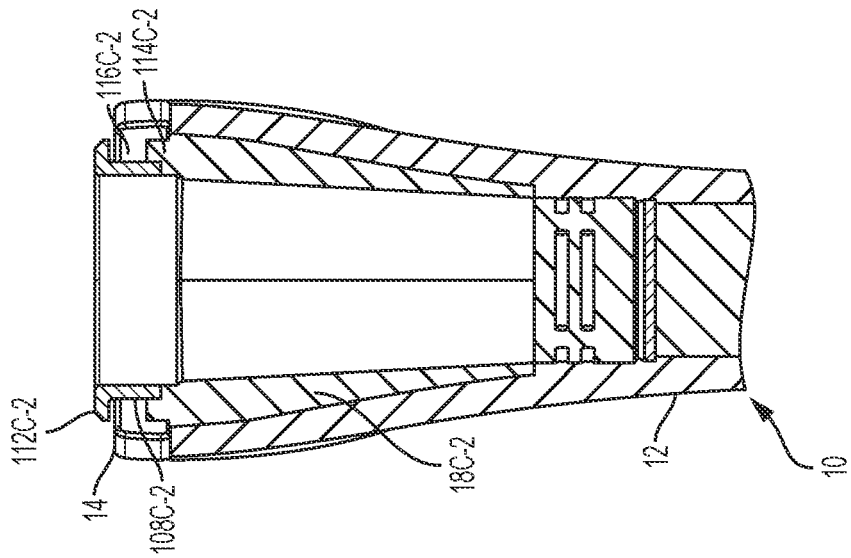
FIG. 27 is a section taken generally along line 27-27 of FIG. 25.
Figure 26:
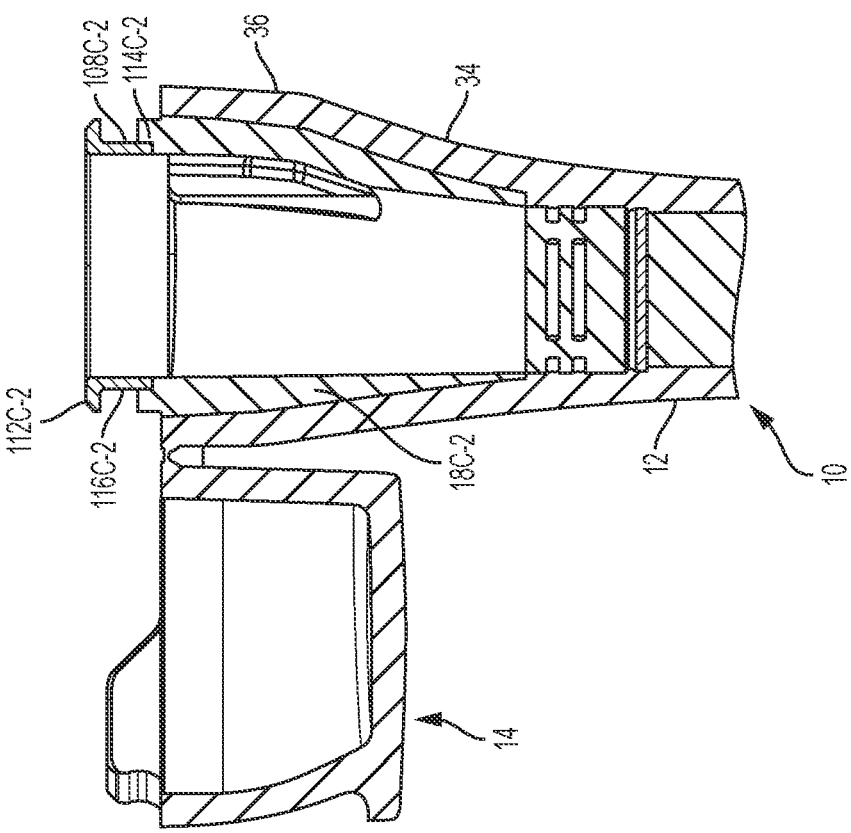
FIG. 26 is a section taken generally along line 26-26 of FIG. 25.
Figure 28:
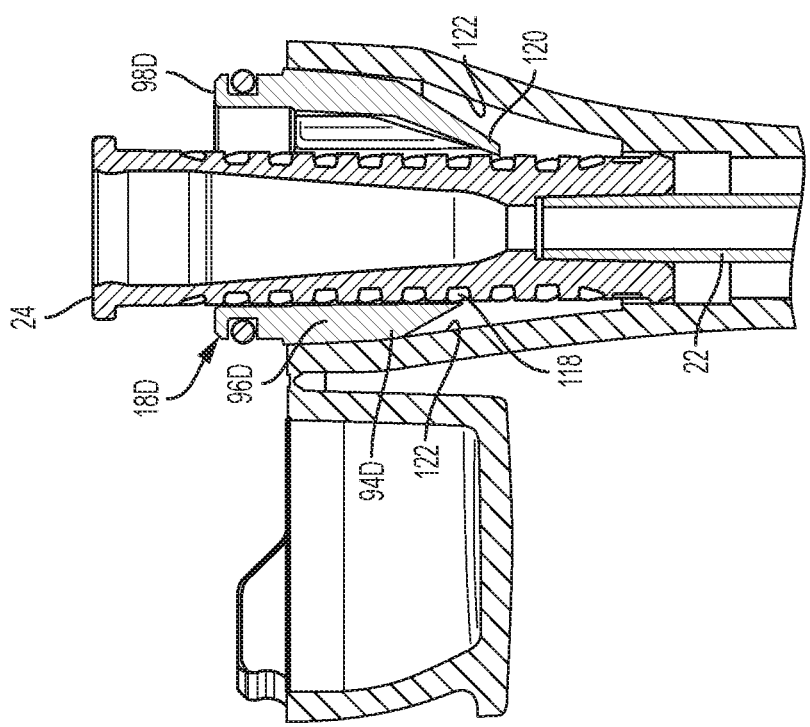
FIG. 28 is a vertical section similar to FIG. 17 but with the cap shown in the open position and with an alternate embodiment of the case insert.
Figure 29:
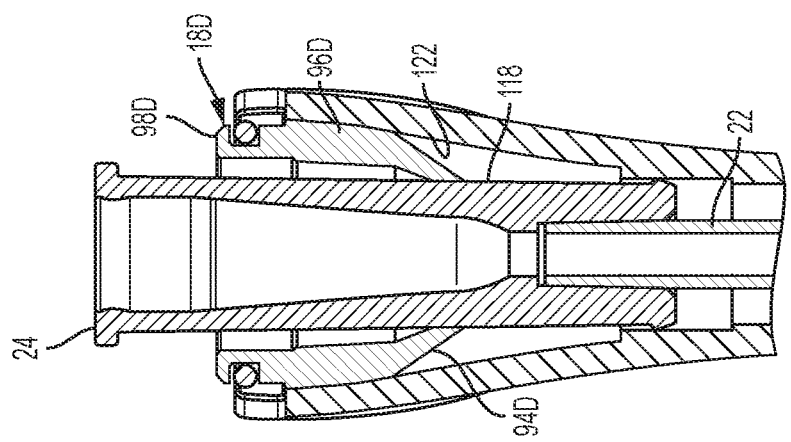
FIG. 29 is a vertical section taken along line 29-29 of FIG. 1 but with the cap shown in the open position and with the case insert of FIG. 28.
Figure 31:
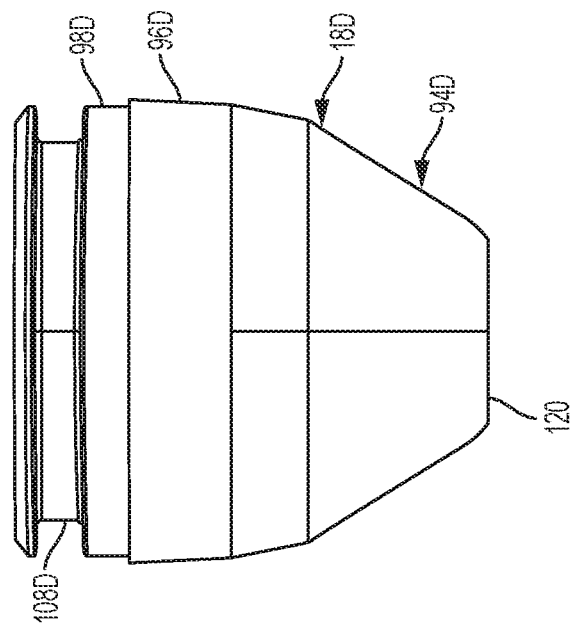
FIG. 31 is a front elevation view of the case insert of FIGS. 28 and 29.
Figure 30:
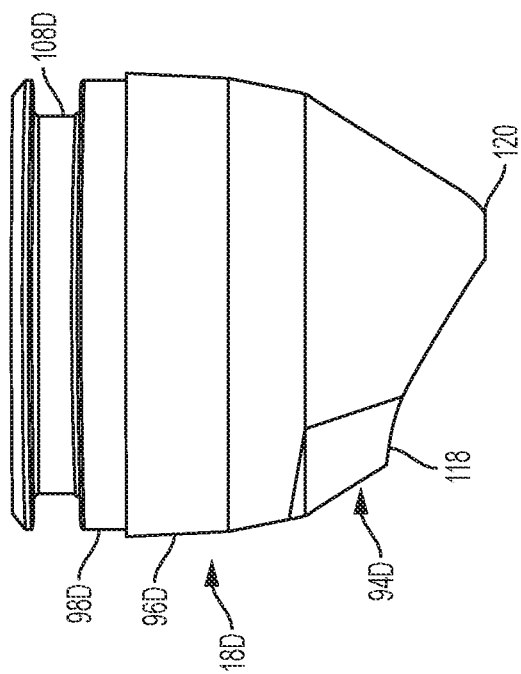
FIG. 30 is a side elevation view of the case insert of FIGS. 28 and 28.

FIGS. 25-27 illustrate a second variation of the case insert 18C. In the embodiment of FIGS. 25-27 a case insert 18C-2 once again differs from case insert 18C only in that the O-ring groove 108C-2 is formed from two separate components. The O-ring groove 108C-2 is defined by upper and lower flanges 112C-2 and 114C-2, respectively. The upper and lower flanges join a root 116C-2 of the groove. In this embodiment the lower flange 114C-2 is integrally formed with the collet 96C-2 of the case insert 18C-2 during a molding operation. But root 116C-2 is not molded with the lower flange 114C-2. Instead, the root 116C-2 is integrally formed with the upper flange 112C-2, with the combination root and upper flange being separate part from the lower flange. This combined root and upper flange is then attached to the lower flange 114C-2 at a later step in the assembly process. Once again, the combined upper flange 112C-2 and root 116C-2 may be attached to the lower flange 114C-2 by ultrasonic welding, or other suitable method.

In both of the case inserts 18C-1 and 18C-2 shown in FIGS. 23-27, the end result is a case insert whose shape is the same as case insert 18C. By forming the O-ring grooves 108C-1 or 108C-2 with two separate components there is no mold parting line on the root surfaces 116C-1 and 116C-2.

FIGS. 28-31 show another alternate embodiment for a case insert 18D. This embodiment is similar to the case insert 18B of FIG. 19 in that it has a collet 96D and a projection 98D, with a groove 108D on the external surface of the projection 98D for receiving a single O-ring 20. As with case insert 18B, the case insert 18D lacks a sleeve. However, case insert 18D does have a truncated transition section 94D. The truncated transition section 94D includes an annular hoop 118 that has an elongated apron 120 on the front side thereof. The apron 120 extends circumferentially about one quarter of the way around the hoop 118 and it merges gradually with the remainder of the hoop. The bottom edges of the hoop 118 and apron 120 form an opening of sufficient diameter to allow the catheter funnel 24 to move easily in and out of the package.

When installed in a case 12 the apron 120 is generally opposite and spaced from the neck 34 of the tubular wall 26 of the case 12. The bottom edges of the hoop 118, including the apron 120 are angled inwardly from the internal surfaces of the case's collar 36 and neck 34. Thus, the hoop 118 is spaced from the case and defines a trap space 122 (FIGS. 28 and 29) between the hoop and the internal surface of the case. The trap space 122 is enlarged in the area of the apron 120. The trap space 122 will trap any loose water in a direct hydration scenario and stop unwanted spillage. That is, in a package using direct hydration there is liquid water in the case for hydrating the catheter. When the catheter is removed, the hydration water could potentially leak out the open case. A hydration liner is one way to prevent this. The case insert 18D provides another way to prevent spillage of hydration water without using a liner. Here the hoop 118 forms the trap space 122 which will collect any hydration water prone to leaking out an opened container and thereby prevent spillage. It will be noted that the amount of hydration water in the case is not sufficient to flood the trap space 122 and spill out through the opening in the center of the case insert 18D.

One of the advantages of using one of the case inserts 18 or 18A to 18D to mount the O-ring 20 where it engages the interior surface of the cap 14 is this arrangement enables the outer contours of the cap 14 and collar 36 to match one another. That is, the exterior shape and outer dimensions of the cap 14 and collar 36 are the same. In the illustrated embodiments the exterior shape of the top land 40 and the bottom land 70 is circular and each land 40 and 70 has the same external diameter. Thus, as the cap closes on the collar the bottom land 70 of the cap's side wall 66 meets the top land 40 of the collar 36 in facing relation. Neither the cap nor the collar overlaps the other and one does not fit inside the other. Instead the case insert's projection 98 fits inside the cap and the cap fits right on top of the collar. This arrangement provides a smooth, continuous contour to the exterior of the package while still sealing against leakage.

Other advantages of the case insert include the fact that the case insert acts as a plug that stops the hydrating fluid from spilling when the case is opened or when the catheter is removed. The case insert combined with the funnel keep the hydrating fluid from spilling into the interior of the cap. Thus, the case insert maintains the hydrating fluid where it belongs, namely, next to the coating on the catheter. The case insert could also be elongated downwardly to include a gel lubrication area. There is also the potential to add a wiping mechanism to the bottom of the case insert so as to remove any excess gel on the catheter.

Further benefits of the case insert include the case insert acting as a seal aid. Due to its material stiffness and design, it gives extra robustness when subject to large external forces compared to the traditional flip cap design in which there is no projection extending above the open end of the case. This affords greater ease of use in terms of the opening and closing force required while ensuring a sterile flip open and close seal is achievable. Also, the case insert and O-ring allow for multiple opening and closing sequences in which a vapor and liquid seal is achieved upon each closing.

An additional benefit of the case insert is the case insert can be used as a funnel gripper. The case insert keeps the funnel in a position that ensures it will not interact with the cap when the cap is being opened or closed. The case insert allows the protrusion of the funnel above the case when the cap is opened, thereby presenting the funnel prominently to the user for gripping. The case insert also gives the latch mechanism more rigidity. Finally, the case insert assists the latch mechanism in resisting lateral forces. Due to its relative stiffness, the case insert aids in maintaining a seal with the closed cap even when the cap is subjected to lateral forces.

It can be seen that the catheter package of FIGS. 1-22 addresses the issues noted above. The shell 62 of the cap 14 surrounds an upstanding funnel 24 when the cap is closed. The neck 34 of the case's tubular wall 26 provides an enlarged diameter for the collar 36 which in turn offsets the vertical axes of the tubular wall 26 and the collar 36. This permits the catheter funnel 24 to be located closer to the hinge 42 than to the detent 48, thereby providing clearance for the cap beyond the funnel during opening and closing movements. At the same time, the case insert 18 provides a mounting location for the O-ring that allows the O-ring to break and make a seal with the interior of the cap multiple times. Finally, the vertical components of the latches 72, 74 interengage with those of the detent 48 to resist lateral loads on the cap.

A further alternate package for medical devices such as intermittent urinary catheters is shown generally at 210 in FIGS. 32-36. The upper portion of such a package is shown here. The major components of the package 210 are a case 212 and a cap 214. The cap is hinged to the case and is selectably movable by a user between a closed position and an open position. FIGS. 32-36 show the cap in the open position.

Details of the case 212 will now be described. The case includes a hollow tube 216 which terminates at an end wall (not shown) that closes the bottom of the tube. The tube may have either a cylindrical or rectangular cross-sectional shape or the cross-section could be otherwise. The tube defines a central axis A (FIG. 36). As can be seen in FIGS. 33 and 36 the upper end of the tube 216 has an internal rib 218 that protrudes inwardly from the inside surface of the tube 216. Rib 218 supports the catheter funnel that will be described below in connection with FIGS. 48-49. Just above the rib 218 there is an internal ledge 220. The ledge is not uniform around the internal diameter of the tube 216 as the ledge has a somewhat greater radial extent on one side of the tube, the right side as seen in FIG. 36. This provides a structure from which the tube flares outwardly somewhat to increase the diameter of the tube at a neck portion 222. The neck portion 222 joins a cylindrical ferrule 224. The ferrule defines a central axis B (FIG. 36) and terminates at an open end which defines a rim 226. It will be noted that axis A of the tube 216 is laterally offset from the axis B of the ferrule 224. That is, axis A is closer to the cap hinge than axis B is. This is advantageous because it places an installed catheter, and in particular the catheter's upstanding funnel, closer to the hinge and farther away from the lug (described below) of the cap. This placement of the catheter makes it less likely that the funnel will interfere with the lug and skirt of the cap as it closes around the top of the funnel. In some respects the ferrule can be considered part of the upper end of the tube 216. On the exterior of the rim 226 there is a small bead 228 (FIG. 36) extending radially outwardly from the ferrule wall. The exterior of the ferrule 224 also carries a tongue 230 extending radially outwardly from the ferrule wall on the side of the ferrule opposite from the cap 214.

A collar 232 surrounds the exterior of the ferrule 224. However, the collar is not concentric with the ferrule and the collar is not exactly cylindrical either. Rather, the collar has a band portion 234 that adjoins the exterior surface of the ferrule. The band portion includes a shoulder 236. The shoulder has an enlarged top land. The shoulder 236 is somewhat below and axially spaced from the tongue 230. The shoulder and tongue have approximately the same circumferential extent. Thus, the shoulder 236 and tongue 230 define a pocket 238 between them. A pad 240 is formed below the shoulder 236 and extends below the band 234 onto the neck 222 of the tube 216.

As the band 234 encircles the ferrule 224 moving circumferentially away from the shoulder 236 the band gradually separates from the exterior surface of the ferrule to form a separate stand-off wall 242. The stand-off wall, while generally curving around the ferrule 224, is non-cylindrical, thereby enabling the stand-off wall to define a space or gap 244 (FIGS. 33 and 36) between itself and the exterior surface of the ferrule 224. The stand-off wall 242 includes two scalloped portions 246A, 246B, each of which merges with one of a pair of ears 248A, 248B, respectively. Between the ears the stand-off wall 242 has a curved panel 250. The panel has a reduced height compared to the ears 248A, 248B. With the foregoing description of the collar 232, it can be seen that the ferrule 224 is generally that portion of the tube 216 above the neck 222 and surrounded by the collar 232.

The top edge of the panel 250 joins one end of a hinge 252, the other end of which connects to the cap 214. The hinge 252 as shown in a living hinge, but other hinge arrangements could be used.

Details of the cap 214 will now be described. The cap 214 includes a generally cup-shaped external shell 254 having a top wall 256 joined to a generally cylindrical side wall 258. The top wall and side wall may merge on one side of the cap to form a lip 259 that makes it easy for a user to engage the cap with a finger or thumb. The hinge 252 is attached to the side wall 258. A depending skirt 260 extends from the bottom edge of the side wall. The skirt includes curved edges 262A, 262B which mate with the scalloped portions 246A, 246B, respectively, of the collar when the cap is closed. This presents a smooth, but interlocking external surface on the top of the package when the cap is closed.

The interior of the skirt also has a lug 264 spaced inwardly from a flange 266 which is on the edge of the skirt. Together the lug 264 and flange 266 define a groove 267 between them. This groove receives the tongue 230 on the ferrule 224 when the cap 214 is closed on the ferrule. The flange 266 and/or the tongue 230 flex to permit the tongue and flange to move past one another during closing or opening. Upon closing the flange 266 ends up in the pocket 238 next to the shoulder 236. This snap fit closure retains the cap 214 closed until such time as a user wishes to open the cap by pushing the cap upwardly adjacent the pad 240.

The interior of the cap is lined or partially lined with a liner 268 made of relatively soft material compared to that of the cap and case. The soft liner promotes a tight seal between the cap 214 and the ferrule 224. It will be noted the liner may include a sprue portion 270 through the top wall 256 of the cap that assists in fixing the liner in place. The open end of the liner is cylindrical so that it can fit snugly around the external surface of the ferrule 224 adjacent to the rim 226 and immediately therebelow. The bead 228 on the rim impinges on the internal surface of the liner 268 to further assist in making a tight seal when the cap is closed. This seal is capable of retaining any hydration mechanism in the case. It will be noted that since the stand-off wall 242, and particularly its curved panel 250, allows all of the hinge connections to be remote from the ferrule 224, neither the hinge 252 nor anything else will interfere with the liner 268 contacting the ferrule's outer surface adjacent the rim 226 when the cap is closed. The skirt 260 of the cap in the closed position engages the top edge of the collar 232, with the liner 268 fitting around the external diameter of the ferrule.

It will also be noted that when the cap is closed a portion of the cap liner 268 will reside in the gap 244 between the ferrule 224 and the stand-off wall 242. This construction of a female cap surrounding a male ferrule when the cap is closed affords a moisture tight seal between the cap and ferrule. At the same time the cap and ferrule construction leaves the opening at the rim 226 of the ferrule 224 unobstructed so that the funnel of an installed catheter can extend beyond the top of the case. This extension of the funnel of an installed catheter beyond the case is desirable from the standpoint of making it easy for a user to grab the funnel and extract the catheter from the case. It also makes it easier to return a used catheter to the package because the end of the funnel is always going to be exposed for a user's fingers to grab and hold. It can be seen that the female cap defines an enclosure which when closed surrounds the extending funnel portion and also permits sealing against the outside surface of the ferrule 224.

A further alternate embodiment of a package according to the present disclosure is shown generally at 272 in FIGS. 37-41. This package 272 in similar to that of FIGS. 32-36 in that it has a case 274 and a cap 276 hinged to the case. The cap is movable by a user between a closed position, shown in FIGS. 37 and 39, and an open position. The cap is shown partially open in FIGS. 38 and 41, where the funnel portion 277 of a catheter can be seen. The case 274 includes a tube 278 having a closed end 280. The tube as shown in this embodiment has a four-sided construction of generally rectangular cross section, although the cross section could be cylindrical or otherwise. The top of the tube 278 has a neck 282 portion that merges with a shoulder 284. The neck and shoulder create an enlargement near the top of the tube. The top land of the shoulder may have a sterile seal made of TPE or silicone for engagement with the bottom rim of the cap. The shoulder has a notch 286 formed on one side thereof. On the side of the tube opposite the notch 286 there is a hinge 288 attached to the shoulder 284.

Figure 40:
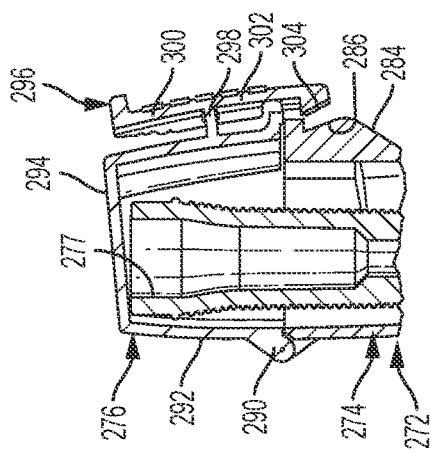
FIG. 40 is a section similar to FIG. 39 but with the operating lever moved to a release position.
Figure 39:
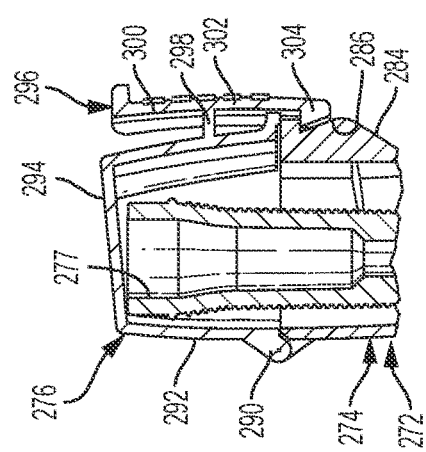
FIG. 39 is a section, on an enlarged scale, taken generally along line 39-39 of FIG. 37, with the cap shown in a closed position and the operating lever in a locked condition.
Figure 41:
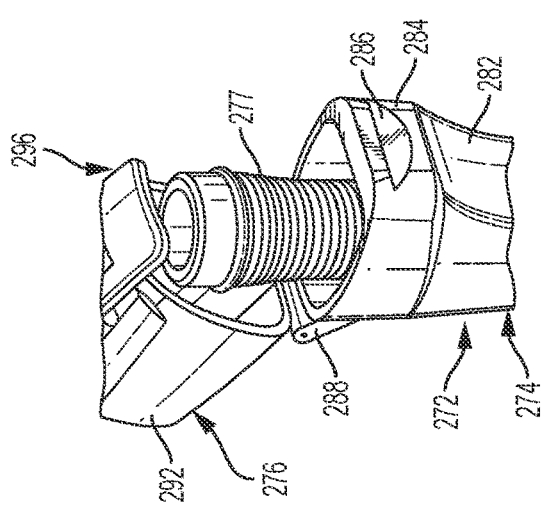
FIG. 41 is a perspective view similar to FIG. 38 but on an enlarged scale showing just the upper end portion of the package.
Figure 38:
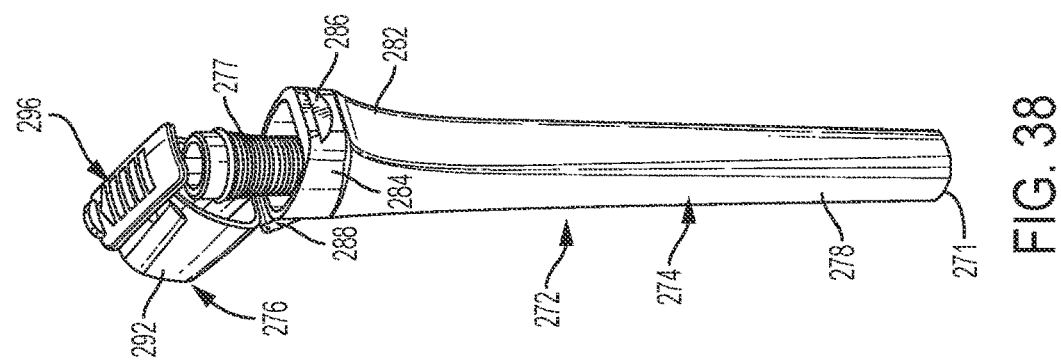
FIG. 38 is a perspective of the package of FIG. 37 but with the cap shown in a partially open position to expose a catheter within the package.
Figure 37:
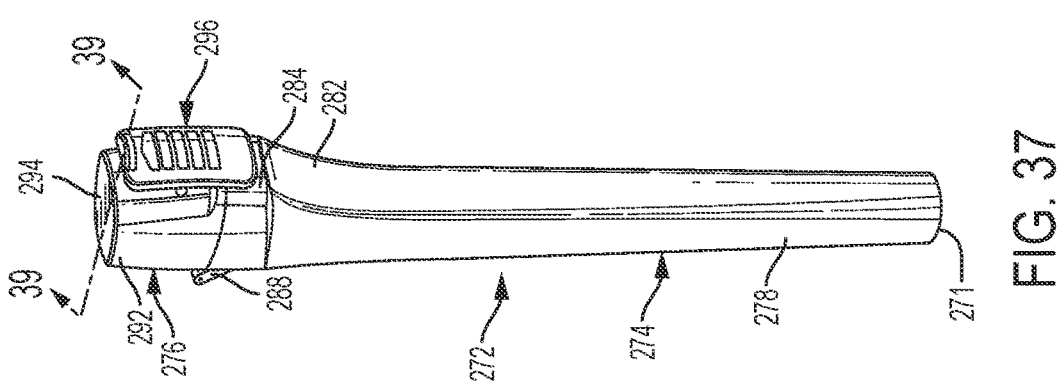
FIG. 37 is a perspective of an entire package according to a second alternate embodiment of the present disclosure, showing the cap in a closed position.

The cap 276 includes its own hinge element 290 (FIGS. 39 and 40) that may be pinned to the hinge 288 on the shoulder 284. The hinge element 290 is attached to a side wall 292 of the cap 276. The top of the cap is closed by a top wall 294. Mounted on the cap opposite the hinge element 290 there is a finger-sized, flexible operating lever 296 attached to the side wall. The lever has a fulcrum 298 (FIGS. 39 and 40) attached to the cap. The lever includes both an opening mechanism 300 above the fulcrum 298 and a locking mechanism 302 below the fulcrum. The locking mechanism includes a hook 304 that is engageable with the notch 286 as seen in FIG. 39. The cap is opened by depressing the opening mechanism 300. When the opening mechanism of the operating lever is depressed, the lever 296 pivots about the fulcrum 298 and thereby disengages the hook 304 from the notch 286 by pulling the hook away from the notch due to the intrinsic stiffness and elasticity of the plastic. This is best seen in FIG. 40. The cap can then be tilted back about the hinges 288, 290, as seen in FIG. 41. Actuation of the locking mechanism 302 will also break a tamper evident feature, such as a piece of an adhesive label (not shown), placed between the locking mechanism 302 on the cap and the case 274.

Turning now to FIGS. 42-45, a hydration liner is shown generally at 306. The hydration liner is sized to fit within either case 212 of FIGS. 32-36 or case 274 of FIGS. 37-41. The liner 306 rests in the tube of the case with the catheter's tube portion (but not the funnel portion) within the liner. The liner defines a space between the liner's exterior surface and the case's interior surface within which a hydration mechanism, such as liquid water may reside. This permits hydration of the surface treatment on the catheter tubing.

The liner 306 may be a relatively rigid plastic such as LDPE or HDPE or other relevant materials. The liner has a generally hollow tube 308. At its upper end there is a seat portion 310 of slightly increased outside diameter compared to the remainder of the tube 308. The seat portion 310 is sized to engage the internal wall of the package case, as will be further explained below. A pair of interference ribs 312 may be formed on the external surface of the seat 310. At the top edge there is a seal 314. In addition to the ribs 312, the external surface of the seat 310 has at its top edge a crab claw seal 314. While the ribs 312 provide stability of the liner 306 while engaged with the internal wall of the package case, the crab claw seal 314 provides a moisture-tight seal against the interior wall of the package case. The walls of the liner tube 308 have formed therein one or more passages or windows 316. The windows will be covered with a patch (not shown) of liquid impermeable/vapor permeable material such as, but not limited to, calcium carbonate. The patches will allow passage of water vapor (for hydration of the catheter) but will block passage of liquid water droplets. The patch might be heat sealed around the perimeter of the window.

FIGS. 46 and 47 illustrate another embodiment of a hydration liner that is shown generally at 306a. Similar to hydration liner 306, hydration liner 306a is sized to fit within either of the cases shown in FIGS. 32-36 and FIGS. 37-41 or any other suitable case. The liner 306a rests in the tube of the case with the catheter's tube portion positioned within the liner. The upper seat portion 310a may have a substantially smooth surface that is sized to engage the internal wall of the package case, such as by a friction fit. The upper seat portion may be held in place by fiction fit, heat sealing, adhesive and/or any other suitable manner of attachment. In one embodiment, the substantially smooth surface of the seat portion 310a may, optionally, include a detent or recess that engages, for example, a protruding lip that may be formed on the interior surface of the tube, such as the lip 326 shown in FIG. 49. The friction fit, heat sealing and/or adhesive between the internal wall of the package and the seat portion 310a may provide a moisture-tight seal or the seat portion 310a may include a seal such as the crab claw seal 314 described above. Similar to liner tube 306, the walls of the liner tube 308a may have formed therein one or more passages or windows 316a that may be covered with a liquid impermeable/vapor permeable material.

The liner tubes disclosed herein may have one or more mechanisms or features that assist in aligning the liner tube during the manufacturing process. For example, when the one or more windows 316, 316a are covered with a liquid impermeable/vapor permeable material, the alignment features and mechanisms may be used to orientate or align the liner tube during a process for attaching the liquid impermeable/vapor permeable material to the liner tube. In one embodiment, the alignment features assist in aligning and holding the liner tuber during a heat sealing process for attaching a liquid impermeable/vapor permeable calcium carbonate material to the liner tube. Such aligning mechanisms and features may also be used to transfer and orient the liner tube along a production line. Furthermore, the case may also include alignment features, which may correspond to the alignment features of the liner tube, that assist in aligning the liner tube and case relative to one another during assembly of the package so that the liner tube is in a desired orientation relative to the case. In one example, the alignment features may include one or more protrusions 313a located at the closed end 311a of the liner tube 308a. Additionally, the alignment features of the liner tube 308a may include flat surfaces located on the sides of liner tube 308a that, optionally, may be tapered. In the illustrated embodiment, liner tube 308a includes a flat, tapered surface 315a. In other examples, the liner tube 308a may include a plurality of flat surfaces. For instance, the liner tube 308a may include flat, tapered surfaces 315a on opposed sides of the tube. Furthermore, the seat 310a of the liner tube 308a may include alignment features that include notches or cutouts 317a. It will be understood that the liner tubes may include one or more of above described alignment features.

FIGS. 48 and 49 illustrate the package 210 of FIGS. 32-36 in an assembly including a hydration liner 306 and a catheter 318 installed in the case 212. The catheter has a funnel 320 and tubing 322 press fit into the bottom of the funnel at a central bore in the funnel. The funnel has a flange 324 (FIG. 49) extending generally radially outwardly on its external surface near the bottom of the funnel. This flange 324 interacts with the internal rib 218 on the internal surface of the case 212 to assist in retaining the catheter 318 in the tube 216. When the catheter is installed in the tube 216 the bottom of the funnel 320 rests on the top land of the hydration liner's seal portion 310. Retention of the seal portion 310 in the tube 216 is aided by the interference ribs 312 surrounding an inwardly protruding lip 326 which is formed on the interior surface of the tube 216.

As shown in FIGS. 48 and 49 and explained above, upon opening of the package 210, the distal end 321 of the funnel 320 projects above the rim 226 and extends or projects out of the opening of the package so that the funnel 320 may be accessed and grasped by the user to remove the catheter 318 from the package. As also discussed above, the catheter 318 is retained within the package by, for example, an interaction between the internal rib 218 of case 212 and flange 324 of the funnel 320, until the user applies sufficient force to remove the catheter from the package. For example, axial movement of the catheter to move the flange 324 past the rib 218. One of the benefits of this retention feature is that the engagement between the catheter 318 and the case 212 resists inadvertent removal of the catheter 318 so that the catheter 318 remains within the opened package 210 until the user actively removes the catheter 318 for use. In other words, the retention feature prevents the catheter 318 from inadvertently falling out of the package 210. For conventional package assemblies wherein the catheter may inadvertently fall out of the package, the catheter is at risk of coming into contact with surfaces that may contaminate the catheter which can result in increasing the risk of infection. Thus, retaining the catheter 318 within the opened package 210 until it is ready for use can assist in reducing the risk of undesired contamination. This is particularly useful for individuals with limited dexterity and for those who have the habit of commencing the catheterization procedure by opening the package and then proceeding with the other steps of the catheterization procedure.

Referring to FIGS. 50-53, there are some catheterization procedures that require the use of a urine collection bag 330 and/or the user prefers to use a urine collection bag 330. In catheterization procedures that use a urine collection bag 330, each of the features of the catheter extending beyond the rim 226 of the opening of the package 210 and the catheter retention feature may provide benefits to the user.

Figure 52:
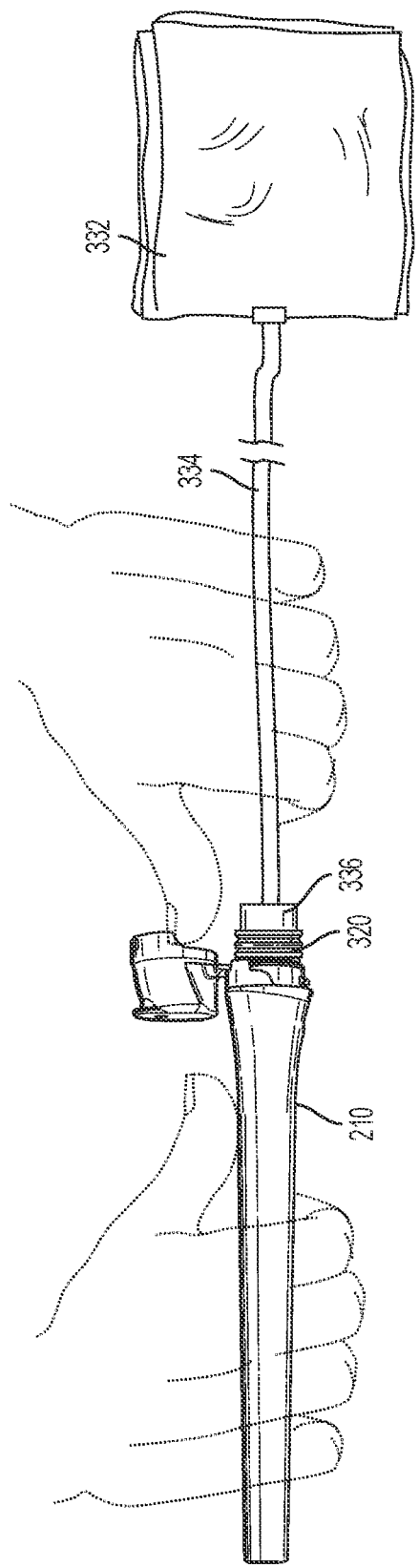
FIG. 52 is a perspective view showing the urine collection bag attached to the funnel of the catheter.

Turning first to the retaining feature, which retains the catheter 318 within the package 210 until the user applies sufficient force to the catheter 318 to remove it from the package 210. Referring to FIG. 50, for illustrative purposes, there is shown a typical urine collection bag 330 that includes a urine collection reservoir 332, such as a plastic bag, a tube 334 for the passage of urine into the collection reservoir 332 and a connector 336 that connects the tube 334 to the funnel 320 of the catheter. In the illustrated embodiment, the connector 336 may include a tapered end portion 338 which is sized to be fitted within the opening of the funnel 320 and be retained within the funnel 320 by a friction fit. Referring to FIGS. 50 and 52, to connect the urine collection bag 330 to the funnel 320, the connector 336 is inserted into the funnel 320 and force is applied to securely fit the connector within the funnel.

In conventional packages already known in the field, the user first removes the catheter from the package and then attaches the urine collection bag to the funnel by grasping the funnel. While connecting the collection bag to the funnel, the user tries to avoid contact with the catheter tube, so as to avoid contamination thereof. This may be difficult for users with limited dexterity and may lead to an increased risk of contamination.

Turning back to FIGS. 50-53, because the catheter 318 is securely retained within the package 210 and the user does not have to be concerned with the catheter 318 inadvertently falling out of the package, the user may grasp the outside of the package 210 (as opposed to only grasping the funnel) to connect the urine collection bag 330 without having to first remove the catheter from the package. The ability to be able to grip the outside of the package 210 provides a larger gripping surface for the user for the user to manipulate the catheter 318 and also reduces the risk of contamination because the catheter 318 remains protected within the package 210 during connection of the connector 336 and the funnel 320. Furthermore, as shown in FIG. 51, after opening of the catheter package 210, the package 210 may be held in virtually any orientation without the concern of the catheter 318 falling out of the package 210. This can be beneficial to users with limited dexterity, especially those that would need to hold the package 210 upside down or with the opening in a downward orientation in order to connect the urine collection bag 330 to the catheter funnel 320.

Figure 53:
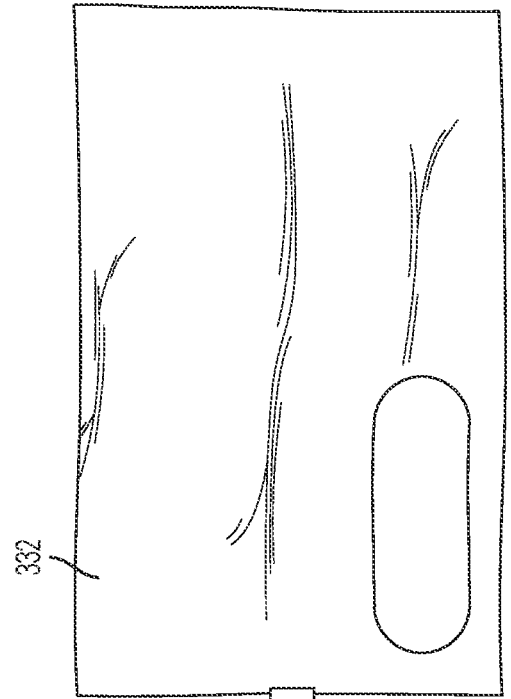
FIG. 53 is a perspective view of the catheter being removed from the package assembly.

Regarding the distal end of the funnel 320 extending above the rim 223 and out of the opening of the package 210, this feature allows the user to see the insertion of the connector 336 into the funnel 320 and visually inspect the connection. Additionally, after the connection has been made, the user may grasp the distal portion of the funnel 320 extending from the opening of the package 210 to remove the catheter 318 from the package 210, as shown in FIG. 53. It will be understood that this ability to connect a collection bag to a funnel while the catheter is still in the package applies to each of the various embodiments of packages shown in this disclosure.

Figure 54:
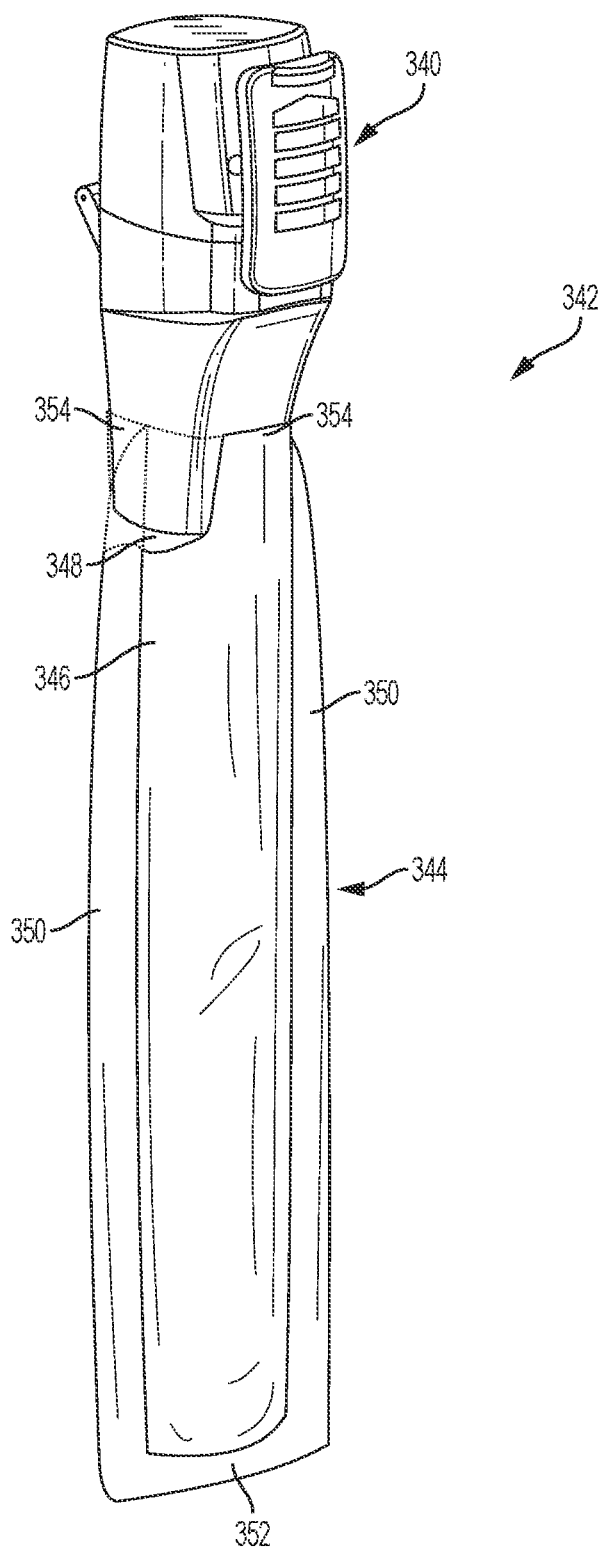
FIG. 54 is a perspective view of another embodiment of a package assembly of the present disclosure.

FIG. 54 illustrates another embodiment of the present disclosure wherein the top 340 of the package 342 has any of the features discussed above, but the bottom 344 of the package 342, which forms or defines the hollow tube that houses the catheter tube, is made from a flexible material. For example, the bottom 344 of the package 342 may be made from one or more flexible polymeric and/or metal foil sheets. The sheet may be a laminate that includes both polymeric and metal layers. In the illustrated embodiment, the bottom 344 of the package 342 may be formed from a front sheet 346 and a back sheet 348 wherein the sheets 346 and 348 are sealed together along the side edges 350 and bottom edge 352. The top edges 354 of the sheets 346 and 348 may be attached to the top 340 of the package 342, by for example, adhesive or welding.

It will be noted that the case 212 and the cap 214 are formed as a single component. This affords the advantage that assembly of multiple parts of the package is not required. Installation of a catheter is all that is needed to complete the product package assembly.

This product is helpful as it addresses issues that many intermittent catheter users are experiencing, especially around the areas of hygiene after use, ease of removal of the catheter and the opening of the product. In these criteria the package of the present disclosure is superior to currently available products, especially in discreet female intermittent catheters. For example, a typical intermittent catheter user is a multiple sclerosis sufferer. Multiple sclerosis sufferers have varying levels of dexterity and grip strength which can also vary from day to day in some patients. Having an easy to open package is reassuring that they will always able to void their bladder confidently.

The hygienic re-capture of the catheter into its packaging is also an advantageous feature of the packaging that other catheters do not fully address; with the flip cap concept of the present disclosure the catheter can be safely captured after use without fears of spills. Our catheter funnel, unlike many prior art funnels, is also able to be used with drainage or collection bags made by a variety of manufacturers. The collection bag could be attached by a user to an upstanding funnel while the catheter is still in the case. The collection bag may have a fitting that goes inside the funnel. The collection bag could then be detached from the funnel after the used catheter is replaced in the case.

Among the advantages of the present disclosure are: intuitiveness to open; ease of opening; ease of removal of the catheter from the case; ease of closing of the case after use; discretion and clean to carry after use; and hygienic use.

Figure 55:
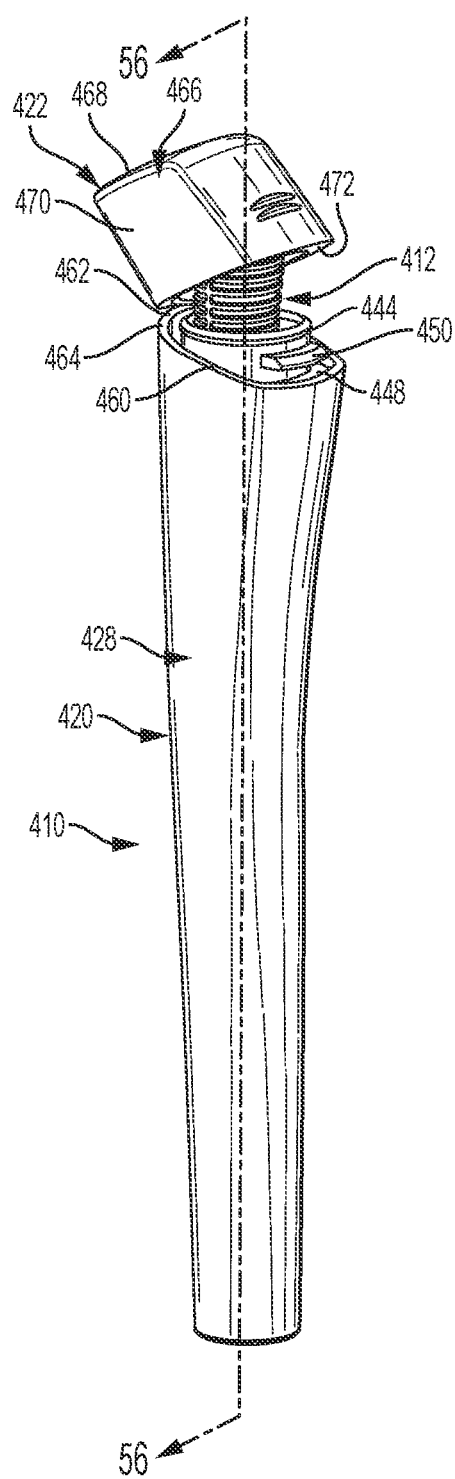
FIG. 55 is a perspective view of a further alternate embodiment of the disclosure, showing a catheter package with a flip cap in a partially open position to expose a catheter funnel in the package.
Figure 56:
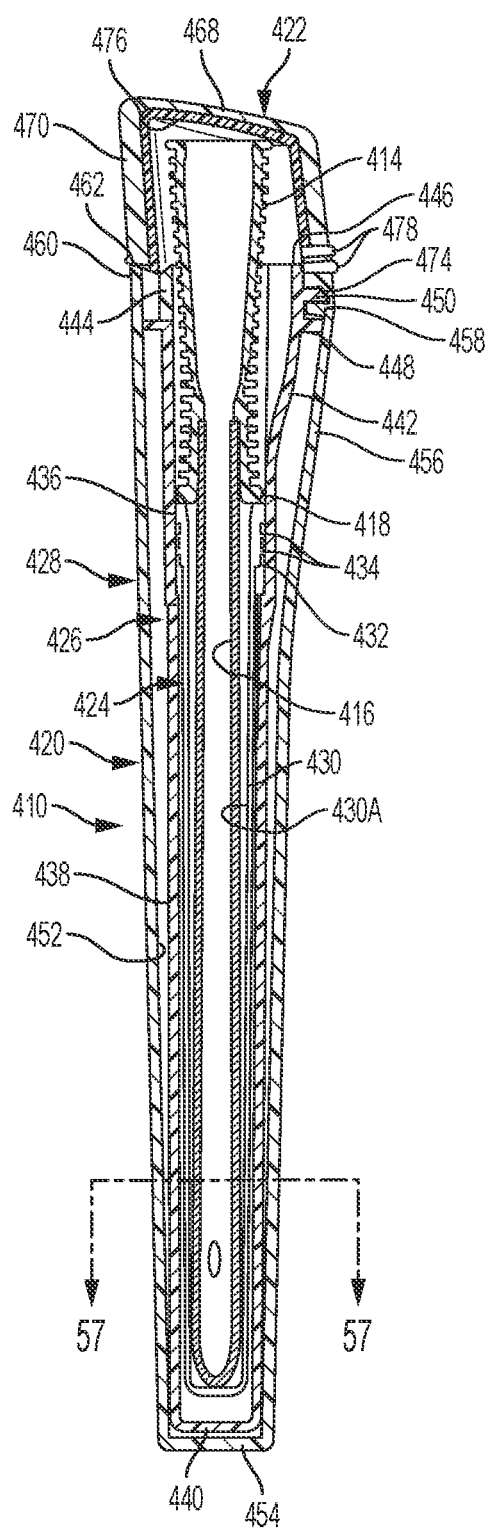
FIG. 56 is a longitudinal section taken along line 56-56 of FIG. 55 but with the cap moved to a closed position.
Figure 57:
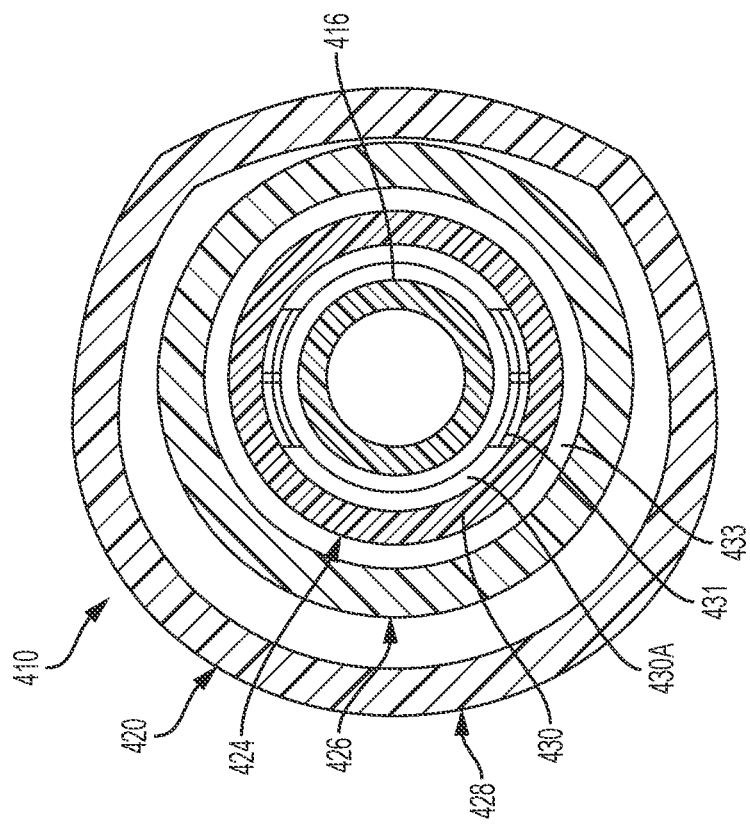
FIG. 57 is a section taken along line 57-57 of FIG. 56.

An additional embodiment of a package for a urinary catheter is shown generally at 410 in FIGS. 55-57. The catheter itself is shown generally at 412 and is best seen in FIG. 56. The catheter has a ribbed funnel 414 and tubing 416 press fit into the bottom of the funnel 414 at a central bore in the funnel. The funnel has a flange 418 extending generally radially outwardly on its external surface near the bottom of the funnel. This flange 418 interacts with the internal surface of the case to assist in retaining the catheter 412 in the package 410. When the catheter is installed in the package the bottom of the funnel 414 rests on the top land of the hydration liner's seat portion 432.

The package 410 includes a container 420 and a cap 422. The cap 422 in this embodiment is a flip cap that is connected to the container by a hinge and is selectably movable by a user between a closed position, shown in FIG. 56, and an open position. FIG. 55 shows the cap 422 in a partially open position. When the cap 422 is fully open a user has access to the open end of the container 420 for removal or replacement of the catheter 412.

The container 420 in this embodiment is a three-part structure including a hydration liner 424, a case 426, and a sleeve 428. Each of these three parts is basically an elongated, hollow tube, closed at the bottom end and open at the top end, with the open top end being selectably openable and closable by the cap 422. The hydration liner 424 fits within the case 426 which in turn fits within the sleeve 428, as best seen in FIGS. 56 and 57.

Details of the hydration liner 424 will now be described. The hydration liner 424 may be a relatively rigid plastic such as LDPE or HDPE or other suitable material. The liner has a generally hollow tube 430 which is closed at the bottom. The liner tube 430 may have a slightly conical shape. The conical shape makes an internal surface of the liner tube wall below the section line visible at 430A in FIG. 57. The walls of the hydration liner's tube 430 also have formed therein one or more passages or windows 431 (FIG. 57). The windows will be covered with a patch (not shown) of liquid-impermeable but vapor-permeable material such as, but not limited to, calcium carbonate. The patches will allow passage of water vapor for hydration of the catheter but will block passage of liquid water droplets. The patches may be heat sealed around the perimeter of the window. Thus, the liner 424 defines a space 433 between the liner's exterior surface and the case's interior surface within which a hydration mechanism, such as liquid water may reside. This permits hydration of the surface treatment on the catheter tubing 416.

At its upper end the exterior of the liner's tube 430 has a seat portion 432 of slightly increased outside diameter compared to the remainder of the tube 430. The seat portion 432 is open at its top such that it can receive the catheter tubing 416. The seat portion 432 has radially-extending interference ribs 434 formed on the external surface thereof. In addition to the ribs 434, the external surface of the seat portion 432 has at its top edge a seal 436. The ribs 434 and seal 436 are sized to engage the internal wall of the case 426. While the ribs 434 engage the internal wall of the case 426 to provide stability, the seal 436 provides a moisture-tight seal against the interior wall of the case 426. This maintains the hydration mechanism, e.g., liquid water, in the space 433 between the liner's exterior surface and the case's interior surface. It will be understood that in an alternate configuration the radially-extending ribs 434 could be formed on the internal wall of the case instead of on the seat portion 432 of the hydration liner 424. Forming the ribs on the case may make it easier to protect the ribs after manufacture of the hydration liner and prior to assembly of the package.

Turning now to the details of the case 426, it includes a hollow tube 438 the bottom of which terminates at an end wall 440 that closes the bottom of the tube 438. The hollow tube 438 may have either a cylindrical or rectangular cross-sectional shape or the cross-section could be otherwise. The upper end of the case 426 flares outwardly somewhat to increase the diameter of the tube at a neck portion 442. The neck portion 442 joins a cylindrical ferrule 444 at the top of the hollow tube 438. The ferrule 444 terminates at an open end which defines a rim 446. On the exterior of the ferrule 444 there is a flange 448 extending radially outwardly from the ferrule wall. This flange 448 interacts with the sleeve 428 as will be explained below. The exterior of the ferrule 444 also carries a tongue 450 extending radially outwardly from the ferrule wall on the side of the ferrule opposite from a hinge for the cap 422.

The sleeve 428 has a shape reminiscent of that of the case 426 except that the sleeve is somewhat larger than the case such that the case can be received inside the sleeve. As such the sleeve 428 has a hollow tube 452 having a lower, closed end wall 454. Toward the top of the tube 452 the sleeve 428 flares outwardly on the right side as seen in FIG. 56 to form a neck portion 456 that encompasses the neck 442 of the case 426. On the right side of FIG. 56 the neck portion 456 terminates just above the flange 448 as at junction 458. Thus, the flange 448 is recessed slightly from the end of the sleeve at 458. However, extending circumferentially around the sleeve from the junction 458, the upper end of the sleeve extends axially beyond the flange 448 to an increasing degree. This forms a collar 460 on the open end of the sleeve 428 that, in a side elevation view, slopes diagonally upwardly from a low point at junction 458 to a high point at the diametrically opposite side of the collar at 462. In other words, the top land 464 of the sleeve 428 extends diagonally to the vertical axis of the sleeve. The top land 464 has an outer contour or outer perimeter as would be best seen in a top plan view of the container with the cap removed.

Details of the cap 422 will now be described. The cap 422 as shown is generally a two-part structure that includes a generally cup-shaped external shell 466 and a liner 476 attached to the interior of the shell 466. The shell has a top wall 468 joined to a side wall 470. The side wall terminates at a generally downwardly facing bottom land 472. A hinge (not shown) is attached to the side wall 470 and to the case 426. The interior of the shell's side wall 470 also has a groove 474 formed therein. This groove 474 receives the tongue 450 on the ferrule 444 when the cap 422 is closed on the ferrule. The tongue 450 flexes to permit the tongue to move into and out of engagement with the groove 474 during closing or opening. Upon closing the tongue 450 ends up in the groove 474. This snap fit closure retains the cap 422 closed until such time as a user wishes to open the cap by pushing the cap upwardly.

The interior of the cap is lined or partially lined with the liner 476 which is made of relatively soft material compared to that of the shell 466 and case 426. The soft liner 476 promotes a tight seal between the cap 422 and the ferrule 444. This seal is dynamic in the sense that it can be repeatedly made and broken whenever the user closes or opens the cap 422, respectively. It will be noted the liner 476 may include sprue portions 478 through the side wall 470 of the cap 422. The sprue portions 478 assist in fixing the liner 476 in place and provide a good gripping surface on the exterior of the cap. The open end of the liner is cylindrical so that it can fit snugly around the external surface of the ferrule 444 adjacent to the rim 446 and immediately therebelow. This seal is capable of retaining any hydration mechanism in the case. The bottom land 472 of the side wall 470 of the cap 422 when in the closed position engages the top land 464 of the sleeve's collar 460. The bottom land has an outer contour that is the same as the outer contour of the top land 464 of the sleeve's collar 460. That is, the outer perimeter of a bottom plan view of the bottom land 472 substantially matches the outer perimeter of a top plan view of the top land 464 of the sleeve 428. This provides a smooth mating of the exterior surfaces of the sleeve 428 and cap 422, thereby creating a pleasing aesthetic appearance to the exterior of the closed package.

Figure 58:
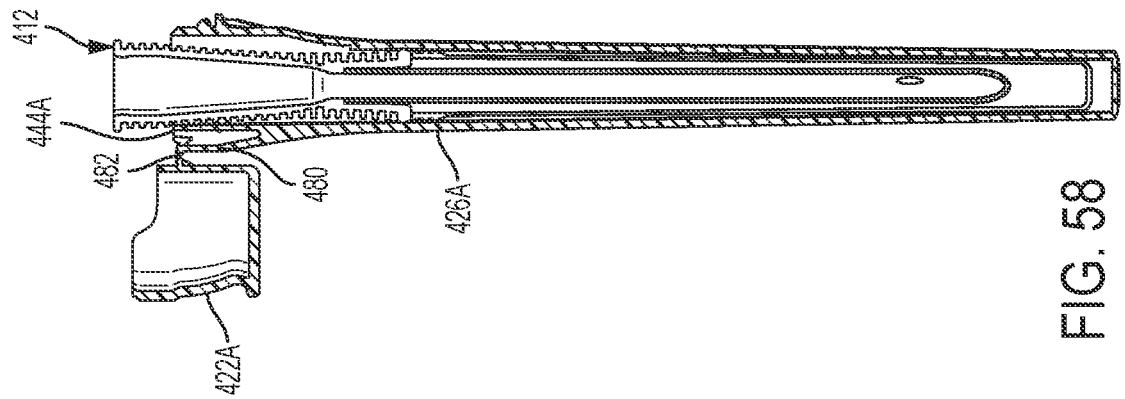
FIG. 58 is a section similar to FIG. 56, showing an alternate arrangement for a hinge connecting a case and a flip cap.

FIG. 58 illustrates an alternate embodiment for hinging the cap to the case. In this embodiment the case 426A includes a stand-off wall 480 that is separate from the exterior surface of the ferrule 444A. The stand-off wall 480, while generally curving around the ferrule 444A, is non-cylindrical, thereby enabling the stand-off wall to define a space or gap between itself and the exterior surface of the ferrule 444A. The top edge of the stand-off wall 480 joins one end of a hinge 482, the other end of which connects to the cap 422A. The hinge 482 as shown in a living hinge, but other hinge arrangements could be used. It will be understood that a sleeve (not shown but similar to sleeve 428) would surround the case 426A and mate with the underside of the cap 422A.

Figure 59:
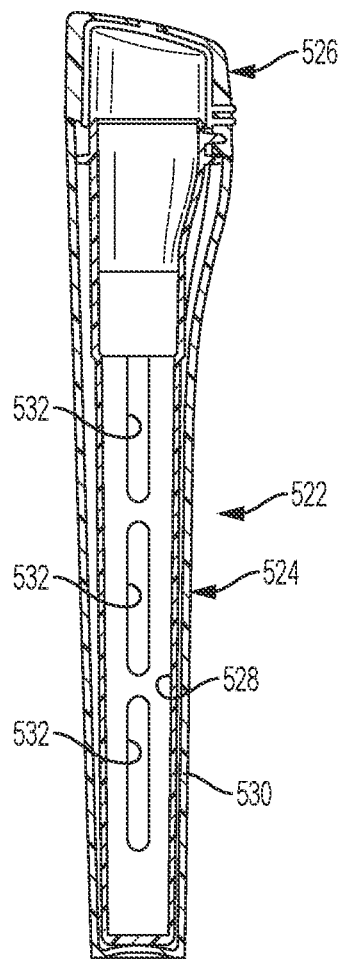
FIG. 59 is a longitudinal section through a package of a further alternate embodiment of the disclosure wherein the container is a two-part structure and no catheter is shown in the package.

A further alternate embodiment of the package of the present disclosure is illustrated generally at 522 in FIG. 59. This is a flip cap version of a package similar to that of the FIGS. 55-58 embodiment in that it has a container 524 and a flip type cap 526. However, the container 524 of FIG. 59 is a two-part structure instead of the three-part structure previously shown. The container 524 has a case 528 and a sleeve 530 surrounding the case, but there is no hydration liner as in the previous embodiments. Instead, the case 528 has windows 532 each covered with a patch (not shown) of liquid-impermeable but vapor-permeable material such as, but not limited to, calcium carbonate. The patches will allow passage of water vapor for hydration of a catheter inside the case but will block passage of liquid water droplets. Thus, the case 528 functions like the hydration liner 424 of the prior embodiments. The case 528 defines a space 534 between the case's exterior surface and the sleeve's interior surface within which a hydration mechanism, such as liquid water may reside. This permits hydration of the surface treatment on the catheter tubing 416. While a flip type cap 526 is shown in this embodiment with a two-part container, it will be understood that a twist cap could also be used.

Figure 60:
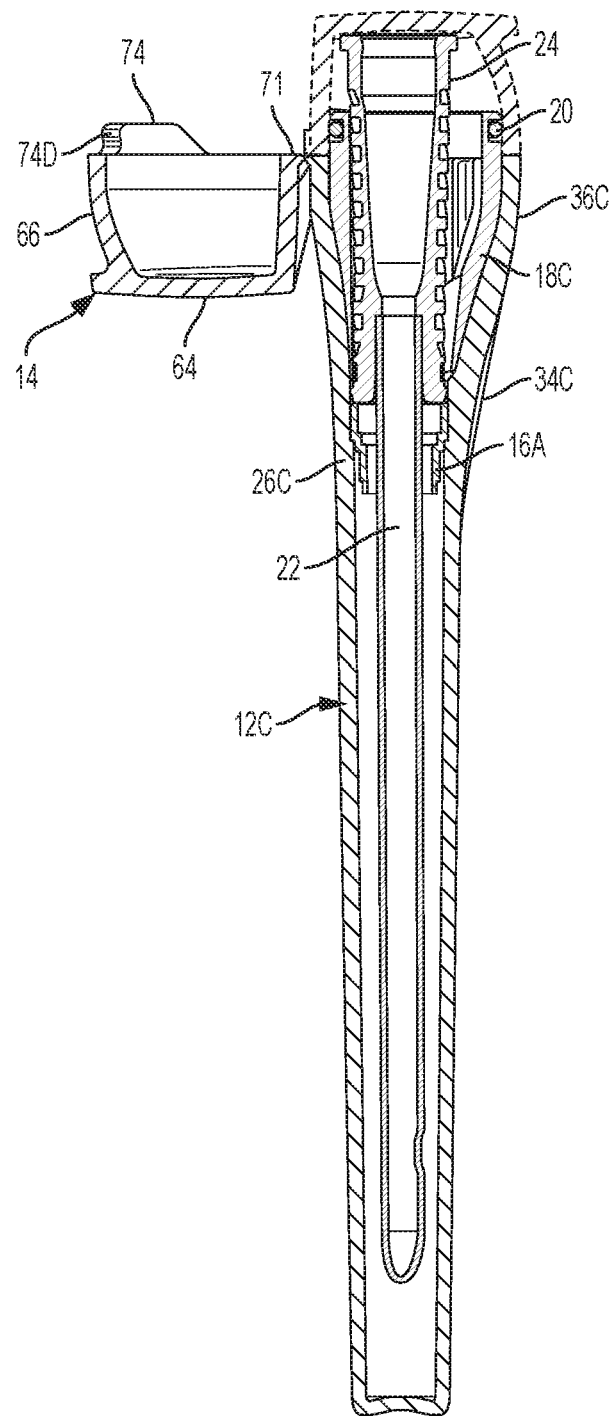
FIG. 60 is a view similar to FIG. 21 showing a further alternate embodiment of a liner.

An alternate version of a liner is shown at 16A in FIG. 60. The liner 16A is similar to liner 16 except that the length of the hollow tube is truncated when compared to the hollow tube 78 of FIG. 21. This truncated version of the liner may be used where direct hydration of the catheter tubing with liquid water is utilized. The upper portion of the seat of the liner 16A will seal against the interior surface of the neck 34C. The catheter tubing will seal against the bottom of the funnel. After removal of the catheter if the case is laid on its side the liner 16A will prevent leakage of hydration water out the open top of the case. This is because the inside diameter of liner 16A is small enough to prevent drainage of the small amount of water used for hydration. That is, with the package on its side, there is not enough hydration water to flood the lowermost wall of a horizontal disposed tube to a depth that would leak out through the center of the liner 16A. Thus, the liner 16A serves as a plug to retain hydration water even when the catheter is not in the package.

Figure 61:
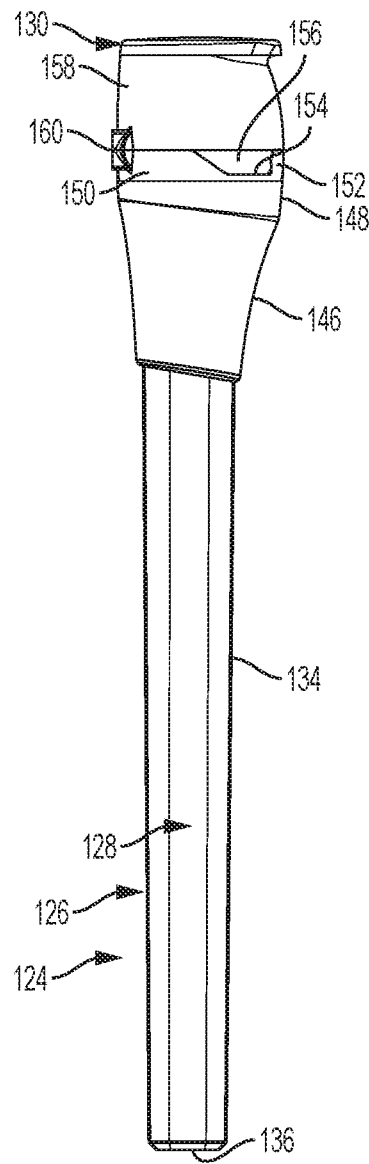
FIG. 61 is a left side elevation view of yet another alternate embodiment of the disclosure wherein the flip cap is separate from the case.
Figure 62:
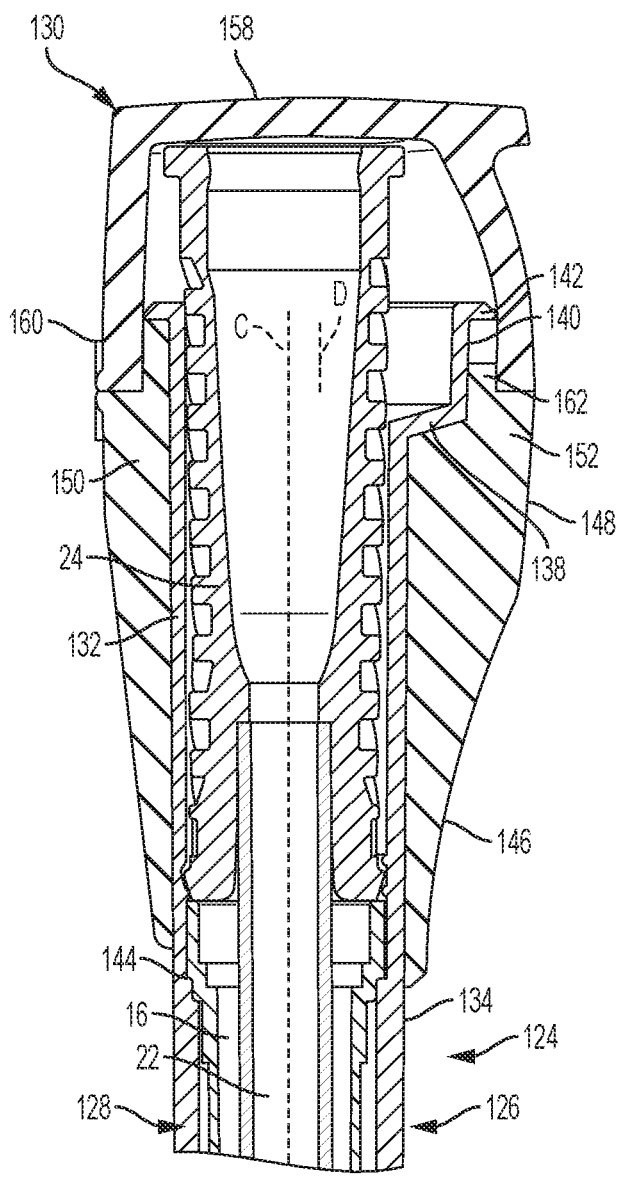
FIG. 62 is a longitudinal section through an assembly of the embodiment of the package shown in FIG. 61.

FIGS. 61 and 62 illustrate yet another embodiment of the present disclosure. This package 124 has a cap and hinge that are essentially similar to those of FIGS. 1-31. Also, package 124 includes a latch mechanism for the cap that includes the interengageable detent, slots and latches as in FIGS. 1-31. But package 124 differs from the previous embodiments in that it has a two-part case 126 comprising a stem section 128 and a flip cap section 130. The upper portion 132 of the stem section 128 extends through and fits tightly within an opening in the flip cap section 130. The vertical axis of the opening in the flip cap section is shown at axis C. The lower portion 134 of the stem section 128 is exposed as it extends below the flip cap section 130. The stem section and flip cap section are fixed to one another by a suitable technique such as welding, adhesive or a snap fit.

The lower portion 134 of the stem section is seen in FIG. 61. Similar to the case 12, the lower portion 134 has a hollow, tubular wall terminating at an end wall 136. The hollow tubular wall of the lower portion 134 may have a generally rectangular cross section as in tubular wall 26. However, in the vicinity of the bottom of the flip cap section 130 the tubular wall of the lower portion 134 gradually merges to a circular cross section such that the upper portion 132 of the stem section 128 has a circular cross section that fits snugly inside the opening through the flip cap section 130, as seen in FIG. 62. Thus, the vertical axis of the lower portion 134 and most of the upper portion 132 coincides with axis C. The circular cross section of the upper portion 132 ceases at the top end of the stem section at a bowed out portion 138 that extends toward the front of the case 126. The underside of the bowed out portion 138 engages a ledge formed on the interior of the flip cap section to limit relative axial movement between the flip cap section and the stem section. The external axial surface of the bowed out portion 138 defines a root 140 of an O-ring groove. The bowed out portion terminates at a radial, upper flange 142 of an O-ring groove. The internal surface of the stem section may have one or more notches as at 144 for locating a hydration liner 16 or a funnel 24.

Looking now at the flip cap section 130, it is noticeably similar to the upper portion of the case 12 in that it includes a body portion have a neck 146 that merges with a generally cylindrical collar 148. The collar and neck define an internal opening therethrough that receives the stem section as described above. The collar 148 terminates at a shoulder 150 and a detent 152. Between them the shoulder and detent define a pair of slots, one of which is seen at 154 in FIG. 61, each of which receives a latch, one of which is seen at 156, on the bottom of a cap 158. The cap is connected to the collar 148 by a hinge 160. With the exception that these flip cap components are not integral with the tubular wall of the stem section 128, the foregoing components are essentially the same as the corresponding components of FIGS. 1-31 and they operate in the same manner as described above.

The flip cap section 130 also includes a cylindrical, axial projection 162, which, as seen in FIG. 62, is indented slightly from the outside diameter of the collar 148. The amount of the indentation is sufficient to receive the wall thickness of the cap 158. The projection 162 defines a vertical axis D. It will be noted that axis D is laterally offset from axis C. This affords the same advantage in terms of clearance between the cap and funnel as described above in connection with axes A and B of FIG. 36. The top land of the projection 162 defines a lower flange of an O-ring groove. Thus, an O-ring groove is defined by the upper flange 142, the root 140 and the lower flange of projection 162. The O-ring groove receives an O-ring (not shown here but the same as O-ring 20) that seals against the internal surface of the cap 158 when the cap is closed and thus prevents any leakage from the package 124. It can be seen that since the upper and lower flanges 142, 162 of the O-ring groove are formed on different parts, there will be no mold parting line on the root 140 of the O-ring groove.

It should be understood that various changes and modifications to the presently preferred embodiments described herein will be apparent to those skilled in the art. Such changes and modification can be made without departing from the spirit and scope of the invention disclosed herein. For example, while the outside or exterior contours of the collar and cap are circular, it could be otherwise so long as each piece has the same contour at the location where they meet one another when the cap is closed. Also, while the case insert is shown mounted in the case, it will be understood that the location of the insert could be switched to place it in the cap. The projection of the insert would then extend axially beyond the bottom land of the cap. The projection would again carry an O-ring to seal against the interior surface of the collar. Thus, the use of the term "case insert" herein does not require that the insert be located in the case. In a similar vein, while the embodiments shown have the latches on the cap and the slots for receiving the latches on the case, the positions of these parts could be reversed such that the latches are on the case and the receiving slots is on the cap. Also, while two latches are shown, a different number could be present.

The invention claimed is:
1. A catheter assembly, comprising:
a package comprising:
  a case having a hollow tube including a closed end and opposed open end;
  a cap;
  a hinge having one end connected to the cap and a second end connected to the open end of the hollow tube, the hinge permitting selectable movement of the cap between an open position, wherein access is provided to the open end of the hollow tube, and a closed position, wherein the cap prevents access to the open end of the hollow tube; and
  a seal connected to at least one of the cap and case, the seal being engageable with the other of the cap and case when the cap is in the closed position to form a seal between the cap and case that can be repeatedly made and broken whenever a user closes or opens the cap, respectively;
a hydrophilic catheter including a catheter tube with a distal end and a proximal end, the distal end including a funnel and a hydrophilic coating on a surface of the catheter tube; and
a hydrating medium.

2. The catheter assembly of claim 1, wherein the case includes a projection at the open end of the hollow tube, the projection having a cylindrical exterior, and the cap includes a shell having a cylindrical interior that receives the projection therein when the cap is in the closed position.

3. The catheter assembly of claim 2, wherein the seal is connected to the exterior of the projection and where the seal is engageable with the interior of the shell when the cap is in the closed position.

4. The catheter assembly of claim 2, wherein the seal is connected to the interior of the shell and where the seal is engageable with the exterior of the projection when the cap is in the closed position.

5. The catheter assembly of claim 3, wherein the seal includes an o-ring and wherein the projection includes a groove to receive the o-ring.

6. The catheter assembly of claim 1, wherein the open end of the hollow tube extends to a collar which terminates at a top land to define an open end of the collar, the top land having an external shape and dimension;

the cap having a side wall which defines an interior of the cap and terminates at a bottom land, the bottom land having an external shape and dimension which matches that of the top land; and
and wherein the top land and the bottom land engage one another in facing relation.

7. The catheter assembly of claim 1, wherein the case further comprises at least one latch formed on one of the case and cap; and at least one first slot formed in the other of the case and cap, the latch and slot being engageable with one another when the cap is closed.

8. The catheter assembly of claim 7, wherein the latch has at least one undercut which defines a tab.

9. The catheter assembly of claim 8, wherein the slot defines at least one ear, the tab and ear being disposed so as to flex past one another during an opening or closing movement of the cap.

10. The catheter assembly of claim 7, further comprising a second latch and each latch having an undercut which defines a pair of tabs.

11. The catheter assembly of claim 10, further comprising a second slot which together with the first slot defines a detent having a pair of ears, the tabs and ears being disposed so as to flex past one another during an opening or closing movement of the cap.

12. The catheter assembly of claim 11, wherein the detent is T-shaped.

13. The catheter assembly of claim 1, wherein the cap further comprises a side wall and a top wall which define an interior of the cap.

14. The catheter assembly of claim 13, wherein the cap further comprises a skirt attached to the side wall.

15. The catheter assembly of claim 14, wherein the case includes a collar with a stand-off wall.

16. The catheter assembly of claim 15, wherein the stand-off wall includes at least one scalloped portion and the skirt has at least one curved portion which mates with the scalloped portion when the cap is in the closed position.

17. The catheter assembly of claim 1, wherein the hollow tube of the case includes a neck portion of increased diameter compared to the rest of the hollow tube.

18. The catheter assembly of claim 1, wherein the cap has a hollow shell and the hollow tube of the case defines a case cavity, the hollow shell of the cap defines a cap cavity and, when the cap is in the closed position a longitudinal axis of the tube intersects the cap cavity such that the cap cavity provides an extension of the case cavity.

19. The catheter assembly of claim 1, wherein the funnel is releasably engaged with an interior surface of the case.

20. The catheter assembly of claim 19 wherein the funnel includes a flange that is releasably engaged with a rib on the interior surface of the case.

* * * * *